(12) United States Patent
Inan

(10) Patent No.: US 7,741,075 B2
(45) Date of Patent: Jun. 22, 2010

(54) PICHIA PASTORIS PIR1 SECRETION SIGNAL PEPTIDE FOR RECOMBINANT PROTEIN EXPRESSION AND PICHIA PASTORIS PIR1 AND PIR2 ANCHOR DOMAIN PEPTIDES FOR RECOMBINANT SURFACE DISPLAY

(75) Inventor: Mehmet Inan, Bothell, WA (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 12/476,830

(22) Filed: Jun. 2, 2009

(65) Prior Publication Data

US 2009/0305347 A1    Dec. 10, 2009

Related U.S. Application Data

(60) Provisional application No. 61/131,230, filed on Jun. 6, 2008.

(51) Int. Cl.
*C12P 21/06* (2006.01)
*C12N 5/00* (2006.01)
*C12N 15/00* (2006.01)
*C07H 21/04* (2006.01)

(52) U.S. Cl. ............... 435/69.1; 435/252.3; 435/254.1; 435/325; 435/320.1; 536/23.1

(58) Field of Classification Search ...................... None
See application file for complete search history.

(56) References Cited

U.S. PATENT DOCUMENTS

| | | | |
|---|---|---|---|
| 6,107,057 | A | 8/2000 | Crawford et al. |
| 7,125,973 | B2 | 10/2006 | Lok |
| 2004/0146976 | A1 | 7/2004 | Wittrup et al. |

OTHER PUBLICATIONS

Tanino et al., "Development of Yeast Cells Displaying Candida Antarctica Lipase B and Their Application to Ester Synthesis Reaction", Appl. Microbiol Biotechnol, 2007, pp. 1319-1325, vol. 75, Springer.
Zhu et al., "The Surface Display of Haemolysin from *Vibrio harveyi* on Yeast Cells and Their Potential Applications as Live Vaccine in Marine Fish", ScienceDirect Vaccine, 2006, pp. 6046-6052, vol. 24, Elsevier.
Boder et al., "Yeast Surface Display for Screening Combinatorial Polypeptide Libraries", Nature Biotechnology, Jun. 1997, pp. 553-557, vol. 15, 1997 Nature Publishing Group.
Chao et al., "Isolating and Engineering Human Antibodies Using Yeast Surface Display", Nature Protocols, 2006, pp. 755-768 and Erratum, vol. 1, No. 2.
Cochran et al., "Domain-Level Antibody Epitope Mapping Through Yeast Surface Display of Epidermal Growth Factor Receptor Fragments", Journal of Immunological Methods, 2004 pp. 147-158, vol. 287.
Feldhaus et al., "Flow-Cytometric Isolation of Human Antibodies from a Nonimmune *Saccharomyces cerevisiae* Surface Display Library", http://www.nature.com/naturebiotechnology, Feb. 2003, pp. 163-170, vol. 21 2003 Nature Publishing Group.

Kondo et al., "Yeast Cell-Surface Display-Applications of Molecular Display", Appl. Microbiol Biotechnol, 2004, pp. 28-40, vol. 64.
Murai et al., "Construction of a Starch-Utilizing Yeast by Cell Surface Engineering", Applied and Environmental Microbiology, Apr. 1997, pp. 1362-1366, vol. 63 No. 4.
Shimma et al., "Constructions of a Library of Human Glycosyltransferases Immobilized in the Cell Wall of *Saccharomyces cerevisiae*", Applied and Environmental Microbiology, Nov. 2006, pp. 7003-7012, vol. 72, No. 11.
Shusta et al., "Directed Evolution of a Stable Scaffold for T-Cell Receptor Engineering", Research Articles—Nature Biotechnology, Jul. 2000, pp. 754-759, vol. 18.
Cregg et al., "Recent Advances in the Expression of Foreign Genes in *Pichia pastoris*", Bio/Technology, Aug. 1993, pp. 905-910, vol. 11, 1993 Nature Publishing Group.
Tanino et al., "Construction of a *Pichia pastoris* Cell-Surface Display System using Flo1p Anchor System", Biotechnol Prog. 2006, pp. 989-993, Flolp, vol. 22.
Furukawa et al., "Development of Novel Yeast Cell Surface Display System for Homo-oligomeric Protein by Coexpression of Native and Anchored Subunits", Biotechnol Prog., 2006, pp. 994-997 vol. 22.
Tshopp et al., "High-Level Secretion of Glycosylated Invertase in the Methylotrophic Yeast, *Pichia pastoris*" Bio/Technology, Dec. 1987, pp. 1305-1308, vol. 5 1987 Nature Publishing Group.
Ilgen et al., "Production of Recombinant Proteins: Novel Microbial and Eukaryotic Expression Systems", Ger Gellissen, Ed., Year unknown, pp. 152-153, Wiley-Vch Verlag GmbH and Co. KGaA.
Vedvick et al., "High-Level Secretion of Biologically Active Aprotinin from the Yeast *Pichia pastoris*", J.Ind Microbiol., 1991, pp. 197-201, vol. 7 Elsevier.
Clare et al., "Production of Mouse Epidermal Growth Factor in Yeast: High-Level Secretion Using *Pichia pastoris* Strains Containing Multiple Gene Copies", Gene, 1991, pp. 205-212, vol. 105 Elsevier.
Wang et al., "Construction of a Novel *Pichia pastoris* Cell-Surface Display System Based on the Cell Wall Protein Pir1", Curr. Microbiol., 2008, pp. 352-357, vol. 56.
Mergler et al., "Development of a Bisphenol A-Adsorbing Yeast by Surface Display of the Kluyveromyces Yellow Enzyme on *Pichia pastoris*", Appl. Microbiol. Biotechnol, 2004, pp. 418-421, GP1, vol. 63 Springer.
Ecker et al., "Pir Proteins of *Saccharomyces cerevisiae* Are Attached to B-1, 3-Glucan by a New Protein-Carbohydrate Linkage", Journal of Biological Chemistry, Apr. 28, 2006, pp. 11523-11529, vol. 281 No. 17.

*Primary Examiner*—Nashaat T Nashed
(74) *Attorney, Agent, or Firm*—Thompson Coburn LLP; Charles P. Romano

(57) ABSTRACT

The present invention is directed to recombinant nucleic acid constructs comprising nucleic acid sequences encoding a *Pichia pastoris* PIR secretion signal peptide for secretion or an anchor domain peptide for surface display of a heterologous polypeptide. The present invention is further directed to methods for obtaining a heterologous polypeptide secreted into the culture medium or displayed on the cell surface. The present invention is also directed to transformed cells containing the recombinant nucleic acid constructs.

9 Claims, 22 Drawing Sheets

Figure 1A. Amino Acid Sequence Alignment of PIR Proteins

```
                                 1                                                  50
SEQ ID NO:  2 (PpPIR1)     (1) --MYRNLIIATALTCGAYSAYVP------SEPWSTLTPDASLESALKDYSQT
SEQ ID NO:  4 (PpPIR2)     (1) MKLAALSTIALTILPVALAGYAP------PDDWSTLTAKGVYPGAFSSYSNT
SEQ ID NO: 19 (ScPIR1)     (1) -MQYKKSLVASALVATSLAAYAP------KDPWSTLTPSATYKGGITDYSST
SEQ ID NO: 22 (ScPIR2)     (1) -MQYKKTLVASALAATTLAAYAP------SEPWSTLTPTATYSGGVTDYAST
SEQ ID NO: 25 (ScPIR3)     (1) -MQYKKPLVVSALAATSLAAYAP------KDPWSTLTPSATYKGGITDYSSS
SEQ ID NO: 28 (ScPIR4)     (1) -MQFKNVALAASVAALSATASAEGYTPGEPWSTLTPTGSISCGAAEYTT
SEQ ID NO: 31 (ScPIR5)     (1) -MHYKKAFLASLLSSIALTAYAP------PEPWATLTPSSKMDGGTTEYRTS
               Consensus        MQYKK LVASALAA ALAAYAP      EPWSTLTPSATY GGITDYSST 51                                                 100
SEQ ID NO:  2 (PpPIR1)    (45) FGIAIKSLDAD------------KIKR------------------------
SEQ ID NO:  4 (PpPIR2)    (47) FGIIVEPLTSS-----------------------------------------
SEQ ID NO: 19 (ScPIR1)    (46) FGIAVEPIATT------------ASSKAKR----------------------
SEQ ID NO: 22 (ScPIR2)    (46) FGIAVQPISTTSSASSAATTASSKAKRAASQIGDGQVQAATTTASVSTKS
SEQ ID NO: 25 (ScPIR3)    (46) FGIAIEAVATSAS----------SVASSKAKR--------------------
SEQ ID NO: 28 (ScPIR4)    (50) FGIAVQAITSS------------KAKR-------------------------
SEQ ID NO: 31 (ScPIR5)    (46) FGLAVIPFTVT------------ESKVKR-----------------------
               Consensus  (51) FGIAV PITTS             SKAKR 101                                                150
SEQ ID NO:  2 (PpPIR1)    (60) --EAVSQIGDGQIQAATITTSSEPK---------------------------
SEQ ID NO:  4 (PpPIR2)    (58) ---VILTPATT-----------------------------------------
SEQ ID NO: 19 (ScPIR1)    (64) -AAAISQIGDGQIQATTKTTAAAVSQIGDGQIQATTKTK-------------
SEQ ID NO: 22 (ScPIR2)    (96) TAAAVSQIGDGQIQATTKTTAAAVSQIGDGQIQATTKTTSAKTTAAAVSQ
SEQ ID NO: 25 (ScPIR3)    (68) -----AASQIGDGQVQAATTAAVSK---------------------------
SEQ ID NO: 28 (ScPIR4)    (65) ----------------------------------------------------
SEQ ID NO: 31 (ScPIR5)    (63) ----------------------------------------KST---------
               Consensus (101)       AVSQIGDGQIQA  T T  A
```

Figure 1B. Amino Acid Sequence Alignment of PIR Proteins

```
                                   151                                                           200
SEQ ID NO:  2 (PpPIR1)       (82)  ------------------------------VTAQVVSQIGDGQIQATTSTSSKSKETAQVVSQI
SEQ ID NO:  4 (PpPIR2)       (66)  ------------------------------THVVSQIDDGQIQIQHTN--TAYVGTAHQVVSQI
SEQ ID NO: 19 (ScPIR1)      (102)  ------------------------------AAAVSQIGDGQIQATTKTTS--AKTTAAAVSQI
SEQ ID NO: 22 (ScPIR2)      (146)  ISDGQIQATTTTLAPKSTAAAVSQIGDGQVQATTTLA-PKSTAAAVSQI
SEQ ID NO: 25 (ScPIR3)       (92)  ------------------------------AAAVSQITDGQVQA--------AKSTAAAVSQI
SEQ ID NO: 28 (ScPIR4)       (65)  ----------------------------------------------------------------
SEQ ID NO: 31 (ScPIR5)       (63)  ------------------------------------------NV----------------ISQI
                  Consensus (151)                                A  VSQI DGQIQAT    A   KSTA   VSQI 201                                                           250
SEQ ID NO:  2 (PpPIR1)      (116)  GDGQIQATTSTSSKSKETAQVVSQIGDGQIQATTSTSSKSKETAQVVSQI
SEQ ID NO:  4 (PpPIR2)       (96)  QDGQIQATS---AVPLPTELASQIADGQIQATTPAG----APATPASQI
SEQ ID NO: 19 (ScPIR1)      (133)  GDGQIQATT-----KTAAAVSQIGDGQVQATT--------KTTAAAVSQI
SEQ ID NO: 22 (ScPIR2)      (195)  GDGQVQATT-----KTTAAAVSQIGDGQVQATT--------KTTAAAVSQI
SEQ ID NO: 25 (ScPIR3)      (117)  TDGQVQAA-----------KSTAAAVSQITDGQVQAA----KSTAAAVSQI
SEQ ID NO: 28 (ScPIR4)       (65)  ---------------------DVISQIGDGQVQATS-----AATAQA
SEQ ID NO: 31 (ScPIR5)       (69)  NDGQVQVTT------QKLPHPVSQIGDGQIQVTTQKVP--PVVSHIVSQI
                  Consensus (201)  GDGQIQATT       K   A  VSQIGDGQIQATT       K  TAAAVSQI 251                                                           300
SEQ ID NO:  2 (PpPIR1)      (166)  GDGQIQATTSTSSKSKETAQVVSQIGDGQIQATTSTSSEVKQTTGVVSQI
SEQ ID NO:  4 (PpPIR2)      (139)  QDGQVQATS---SADAHPTAHSQAEDIGAHSLSSTG----LIPGTLTTV
SEQ ID NO: 19 (ScPIR1)      (171)  GDGQIQATT-----KTTAAAVSQIGDGQIQATTN---------TTVAPVSQI
SEQ ID NO: 22 (ScPIR2)      (233)  GDGQVQATT-----KTTAAAVSQIGDGQVQATTK---------TTAAAVSQI
SEQ ID NO: 25 (ScPIR3)      (153)  TDGQVQAA-----------KSTAAASQISDGQVQATT------STKAAASQI
SEQ ID NO: 28 (ScPIR4)       (86)  TDSOAQATT----------TATPTSSEKISSSASKTSTN---------
SEQ ID NO: 31 (ScPIR5)      (111)  GDGQLQITTAKNVVTKSTIAVPSKTVTATATSTAT------AVS---QI
                  Consensus (251)  GDGQVQATT         KSTAAA  SQI DGQIQATT           T A  VSQI
```

Figure 1C. Amino Acid Sequence Alignment of PIR Proteins

```
                                 301                                              350
SEQ ID NO: 2  (PpPIR1)  (216)    GDGQIQATTATTSVASQIGDGQVQ----ESKPTDTSEDKGTSDLVSCLTDS
SEQ ID NO: 4  (PpPIR2)  (181)    LTSTGSDTTLTLVTVTETEVVTYTPEVTVTVNRNAAKVKRDNIESACLTPQ
SEQ ID NO: 19 (ScPIR1)  (209)    TDGQIQATTLTSATIIPS---------PAPAPITNGTDPVTAETCKSSG
SEQ ID NO: 22 (ScPIR2)  (271)    TDGQVQATTKTTQAASQVSDGQVQATTATSASAAATSTDPVDAVSCKTSG
SEQ ID NO: 25 (ScPIR3)  (189)    TDGQIQASKTTSGASQVSDG-------QVQATAEVKDANDPVDVVSCNNNS
SEQ ID NO: 28 (ScPIR4)  (115)    --------------------------ATSSSCATPSLRKDSSCKNSG
SEQ ID NO: 31 (ScPIR5)  (151)    HDGQVQVTISSASSSSVLSKS------KLEPTKKPNNEKVIKVQACKSSG
              Consensus  (301)    DGQIQATT TS  A                            T  A   V    SCKTSG 351                                              400
SEQ ID NO: 2  (PpPIR1)  (263)    SLALVLEKGVLTDAQGRIGAIVANRQFQFDGPPPQAGTIYAGGWSITDDA
SEQ ID NO: 4  (PpPIR2)  (231)    ALGLTLKDSVLLDLQGRVGSIVANRQFQFDGPPPQAGTIYAVGWSITPNG
SEQ ID NO: 19 (ScPIR1)  (249)    TLEMNLKGGILTDGKKGRIGSIVANRQFQFDGPPPQAGAIYAAGWSITPEG
SEQ ID NO: 22 (ScPIR2)  (321)    TLEMNLKGGILTDGKGKGRIGSIVANRQFQFDGPPPQAGAIYAAGWSITPDG
SEQ ID NO: 25 (ScPIR3)  (233)    TLSMSLSKGILTDRKGRIGSIVANRQFQFDGPPPQAGAIYAAGWSITPEG
SEQ ID NO: 28 (ScPIR4)  (135)    TLELTLKDGVLTDAKGRIGSIVANRQFQFDGPPPQAGAIYAAGWSITEDG
SEQ ID NO: 31 (ScPIR5)  (195)    TLAITLQGGVLIDSSGRIGSIVANRQFQFDGPPPQAGAIYAGGWSITKHG
              Consensus  (351)    TL LTLK  GVLTDAKGRIGSIVANRQFQFDGPPPQAGAIYAAGWSITPDG 401                                              444
SEQ ID NO: 2  (PpPIR1)  (313)    KLALGNSTTFYQCLSGTFYNLYDEKIGEQCEPVELDIVDLIEC-
SEQ ID NO: 4  (PpPIR2)  (281)    YLALGDSEVFYQCLSGSFYNLYDQHIAEQCEAVHLKAVDLISC-
SEQ ID NO: 19 (ScPIR1)  (299)    NLAIGDQDTFYQCLSGNFYNLYDEHIGTQCNAVHLQAIDLLNC-
SEQ ID NO: 22 (ScPIR2)  (371)    NLAIGDNDVFYQCLSGTFYNLYDEHIGSQCTPVHLEAIDLIDC-
SEQ ID NO: 25 (ScPIR3)  (283)    NLALGDQDTFYQCLSGDFYNLYDKHIGSQCHEVYLQAIDLIDC-
SEQ ID NO: 28 (ScPIR4)  (185)    YLALGDSDVFYQCLSGNFYNLYDQNVAEQCSAIHLEAVSLVDC-
SEQ ID NO: 31 (ScPIR5)  (245)    TLAIGDNDVFYQCLSGTFYNLYDQSIGGQCNPVHLQTVGLVDC-
              Consensus  (401)    LALGDNDVFYQCLSGTFYNLYD HIG  QC   VHL  AVDLIDC
```

Figure 2.    Amino Acid Sequence Alignment of PIR Secretion Signal Peptides

```
                                  1                                                 50
SEQ ID NO: 15  (PpPIR1SS)   (1) -MYRNLITATALTCGAYSA----YVPSEPWSTLTPDASLESALKDYSQTF
SEQ ID NO: 17  (PpPIR2SS)   (1) ---MKLAALSTIALTILPVALAGYAPPDDWSTLTAKGVYPGAFSSYSNTF
SEQ ID NO: 20  (ScPIR1SS)   (1) MQYKKSLIVASALVATSLAA----YAPKDPWSTLTPSATYKGGITDYSSTF
SEQ ID NO: 26  (ScPIR3SS)   (1) MQYKKPLVVSALAATSLAA-----YAPKDPWSTLTPSATYKGGITDYSSSF
SEQ ID NO: 23  (ScPIR2SS)   (1) MQYKKTLVASALAATTLAA-----YAPSEPWSTLTPTATYSGGVTDYASTF
SEQ ID NO: 32  (ScPIR5SS)   (1) MHYKKAFLASLLSSIALTA-----YAPPEPWATLTPSSKMDGGTTEYRTSF
SEQ ID NO: 29  (ScPIR4SS)   (1) MQFKNVALAASVAALSATASAEGYTPGEPWSTLTPTGSISCGAAEYTTTF
               Consensus       MQYKK LVASALAATSLAA    YAP EPWSTLTPSATY GGITDYSSTF 51                     76
SEQ ID NO: 15  (PpPIR1SS)  (46) GIAIKSLDADKIKR------------
SEQ ID NO: 17  (PpPIR2SS)  (48) GIIVEPLTSSVILTPATTTHVV----
SEQ ID NO: 20  (ScPIR1SS)  (47) GIAVEPIATTASSKAKR---------
SEQ ID NO: 26  (ScPIR3SS)  (47) GIAIEAVATSASSVASSKAKR-----
SEQ ID NO: 23  (ScPIR2SS)  (47) GIAVQPISTSSASSAATTASSKAKR
SEQ ID NO: 32  (ScPIR5SS)  (47) GLAVIPFTVTESKVKR----------
SEQ ID NO: 29  (ScPIR4SS)  (51) GIAVQAITSSKAKR------------
               Consensus   (51) GIAV PITTS S
```

Figure 3A. Amino Acid Sequence Alignment of PIR Anchor Domain Peptides

```
                                1                                               50
SEQ ID NO: 16 (PpPIR1AD)   (1) ------------------------------------EAVSQIGDGQIQAATITSSEPK----
SEQ ID NO: 18 (PpPIR2AD)   (1) ----------------------------------------------------------------
SEQ ID NO: 30 (ScPIR4AD)   (1) ----------------------------------------------------------------
SEQ ID NO: 33 (ScPIR5AD)   (1) ----------------------------------------------------------------
SEQ ID NO: 27 (ScPIR3AD)   (1) ---------------------------------------------AASQIGDGQVQAATTTAAVSK-
SEQ ID NO: 21 (ScPIR1AD)   (1) ----------------------------------------AAAISQIGDGQIQATTKTTAAAVSQI
SEQ ID NO: 24 (ScPIR2AD)   (1) AASQIGDGQVQAATTTASVSTKSTAAAVSQIGDGQIQATTKTTAAAVSQI
                 Consensus  (1)                                      A SQIGDGQIQA  T  T  A 51                                              100
SEQ ID NO: 16 (PpPIR1AD)  (23) ---------------------------------VT---AQVVSQIGD
SEQ ID NO: 18 (PpPIR2AD)   (1) ------------------------------------HVVSQIDD
SEQ ID NO: 30 (ScPIR4AD)   (1) ----------------------------------------------
SEQ ID NO: 33 (ScPIR5AD)   (1) ----------------------------------------------
SEQ ID NO: 27 (ScPIR3AD)  (22) ----KST-----------------------------A----AAVSQITD
SEQ ID NO: 21 (ScPIR1AD)  (27) GDGQIQATTKTK--------------------------A---AAVSQIGD
SEQ ID NO: 24 (ScPIR2AD)  (51) GDGQIQATTKTTSAKTTAAAVSQISDGQIQATTTLAPKSTAAAVSQIGD
                 Consensus (51)                                       VSQI D 101                                             150
SEQ ID NO: 16 (PpPIR1AD)  (34) GQIQATTSTSSKSKETAQVVSQIGDGQIQATTSTSSKSKETAQVVSQIGD
SEQ ID NO: 18 (PpPIR2AD)   (9) GQIQHTN--TAYVGTAHQVVSQIGDGQIQATAS---AVPLPTELASQIAD
SEQ ID NO: 30 (ScPIR4AD)   (1) ------------------NVISQINDGQVQVTT------QKLPHPVSQIGD
SEQ ID NO: 33 (ScPIR5AD)   (1) --------------------------------------------------
SEQ ID NO: 27 (ScPIR3AD)  (34) GQVQA-------AKSTAAAVSQITDGQVQAA------KSTAAAVSQITD
SEQ ID NO: 21 (ScPIR1AD)  (48) GQIQATTKTTS-AKTTAAAVSQIGDGQIQATT------KTKAAAVSQIGD
SEQ ID NO: 24 (ScPIR2AD) (101) GQVQATTTTLA-PKSTAAAVSQIGDGQVQATT------KTTAAAVSQIGD
                 Consensus(101) GQIQAT   A   KSTA   VSQIGDGQIQATT      K   A   VSQIGD
```

Figure 3B. Amino Acid Sequence Alignment of PIR Anchor Domain Peptides

```
                               151                                                         200
SEQ ID NO: 16 (PpPIR1AD)  (84) GQIQATTSTSSKSKETAQVSQIGDGQIQATTSTSSKSKETAQVVSQIGD
SEQ ID NO: 18 (PpPIR2AD)  (54) GQIQATTPAG----APATPASQIQDGQVQATSS-----ADAHPTAHSQAED
SEQ ID NO: 30 (ScPIR4AD)   (1) ---------------------DVISQIGDGQVQATS-----------AATAQATD
SEQ ID NO: 33 (ScPIR5AD)  (28) GQIQVTTQKVP--PVVSHIVSQIGDGQLQITTAKNVVTKSTIAVPSKTVT
SEQ ID NO: 27 (ScPIR3AD)  (70) GQVQAA-------KSTAAAVSQITDGQVQAA-------KSTAAAASQISD
SEQ ID NO: 21 (ScPIR1AD)  (91) GQIQATT------KTTAAAVSQIGDGQIQATT------KTTAAVSQIGD
SEQ ID NO: 24 (ScPIR2AD) (144) GQVQATT------KTTAAAVSQIGDGQVQATT------KTTAAAVSQIGD
              Consensus  (151) GQIQATT       K TA  VSQIGDGQVQATT       KSTAAA SQI D 201                                                         250
SEQ ID NO: 16 (PpPIR1AD) (134) GQIQATTSTSSSEVKQTTGVVSQIGDGQIQATTATTSVASQIGDGQVQES-
SEQ ID NO: 18 (PpPIR2AD)  (96) IGAHSLSSTG----LIPGTLTTVLTSTGSDTTLTLVTVETEVTYTPEVT
SEQ ID NO: 30 (ScPIR4AD)  (24) SQAQATTT--------AT-PTSSEKISSSASKTSTNATSS---------
SEQ ID NO: 33 (ScPIR5AD)  (76) ATATSTAT--------AVS-QIHDGQVQVTISSASSSSVLS-------KS
SEQ ID NO: 27 (ScPIR3AD) (106) GQVQATT---------STKAAASQITDGQIQASKTTSGASQVSDG-----Q-
SEQ ID NO: 21 (ScPIR1AD) (129) GQIQATTN--------TTVAPVSQITDGQIQATTLTSATIIPS------P-
SEQ ID NO: 24 (ScPIR2AD) (182) GQVQATTK--------TTAAAVSQITDGQVQATTKTTQAASQVSDGQVQATT
              Consensus  (201) GQIQATTS          T A VSQITDGQIQATT TTSTAS 251                                                         300
SEQ ID NO: 16 (PpPIR1AD) (183) --KPTDTSEDKGTSDLVSCLTDSLIAVLEKGVLTDAQGRIGAIVANRQF
SEQ ID NO: 18 (PpPIR2AD) (142) VTVNRNAAKVKRDNIESACLTPQALGLTLKDSVLLDLQGRVGSIVANRQF
SEQ ID NO: 30 (ScPIR4AD)  (55) ---SCATPS-----LKDSSCKNSGTLELTLKDGVLTDAKGRIGSIVANRQF
SEQ ID NO: 33 (ScPIR5AD) (110) KLEPTKKPNNEKVIKVQACKSSGTLAITLQGGVLIDSSGRIGSIVANRQF
SEQ ID NO: 27 (ScPIR3AD) (143) VQATAEVKDANDPVDVSCNNNSTLSMSLSKGILTDRKGRIGSIVANRQF
SEQ ID NO: 21 (ScPIR1AD) (165) --APAPITNGTDPVTAETCKSSGTLEMNLKGGILTDGKGRIGSIVANRQF
SEQ ID NO: 24 (ScPIR2AD) (226) ATSASAAATSTDPVDAVSCKTSGTLEMNLKGGILTDGKGRIGSIVANRQF
              Consensus  (251)     V     SCKTSGTL LTLK  GVLTDAKGRIGSIVANRQF
```

Figure 3C. Amino Acid Sequence Alignment of PIR Anchor Domain Peptides

```
                               301                                              350
SEQ ID NO: 16 (PpPIR1AD) (231) QFDGPPPQAGTIYAGGWSITDDAKLALGNSTTFYQCLSGTFYNLYDEKIG
SEQ ID NO: 18 (PpPIR2AD) (192) QFDGPPPQAGTIYAGWSITPNGYLALGDSEVFYQCLSGSFYNLYDQHIA
SEQ ID NO: 30 (ScPIR4AD)  (98) QFDGPPPQAGAIYAAGWSITEDGYLALGDSDVFYQCLSGNFYNLYDQNVA
SEQ ID NO: 33 (ScPIR5AD) (160) QFDGPPPQAGAIYAGGWSITKHGTLAIGDNDVFYQCLSGTFYNLYDQSIG
SEQ ID NO: 27 (ScPIR3AD) (193) QFDGPPPQAGAIYAAGWSITPEGNLALGDQDTFYQCLSGDFYNLYDKHIG
SEQ ID NO: 21 (ScPIR1AD) (213) QFDGPPPQAGAIYAAGWSITPEGNLAIGDQDTFYQCLSGNFYNLYDEHIG
SEQ ID NO: 24 (ScPIR2AD) (276) QFDGPPPQAGAIYAAGWSITPDGNLAIGDNDVFYQCLSGTFYNLYDEHIG
             Consensus   (301) QFDGPPPQAGAIYAAGWSITPDG LALGDNDVFYQCLSGTFYNLYD HIG 351           367
SEQ ID NO: 16 (PpPIR1AD) (281) EQCEPVELDIVDLIEC-
SEQ ID NO: 18 (PpPIR2AD) (242) EQCEAVHLKAVDLISC-
SEQ ID NO: 30 (ScPIR4AD) (148) EQCSAIHLEAVSLVDC-
SEQ ID NO: 33 (ScPIR5AD) (210) GQCNPVHLQTVGLVDC-
SEQ ID NO: 27 (ScPIR3AD) (243) SQCHEVYLQAIDLIDC-
SEQ ID NO: 21 (ScPIR1AD) (263) TQCNAVHLQAIDLLNC-
SEQ ID NO: 24 (ScPIR2AD) (326) SQCTPVHLEAIDLIDC-
             Consensus   (351) QC  VHL AVDLIDC-
```

Figure 4. Diagram of the AOX – PpPIR1 secretion sequence – EGFP Construct
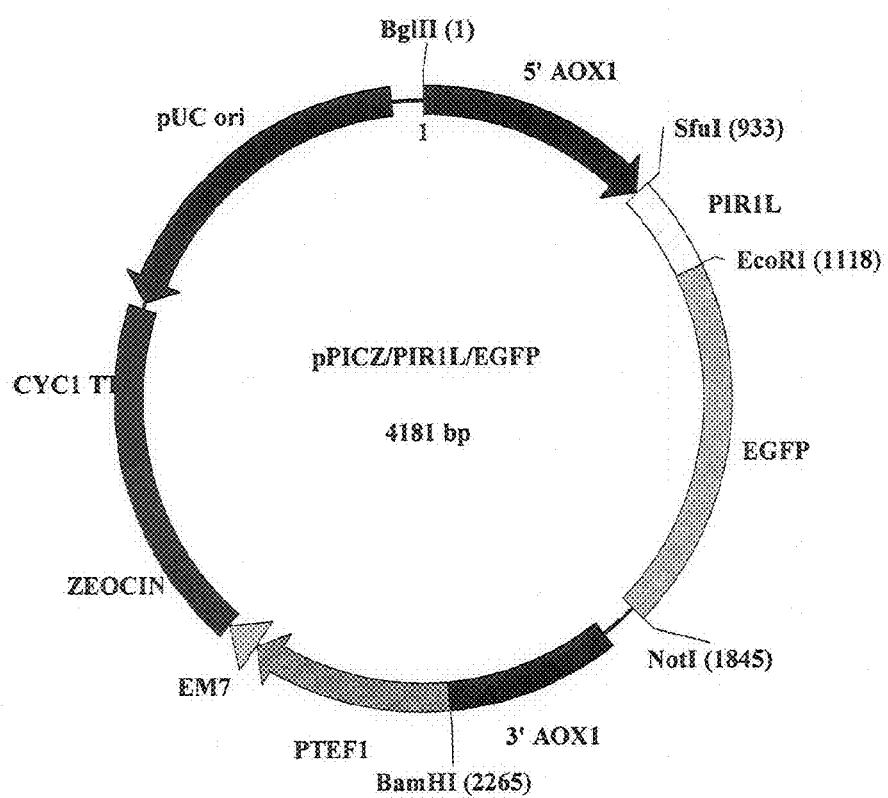

Figure 5. Diagram of the GAP – PpPIR1 secretion sequence – EGFP Construct
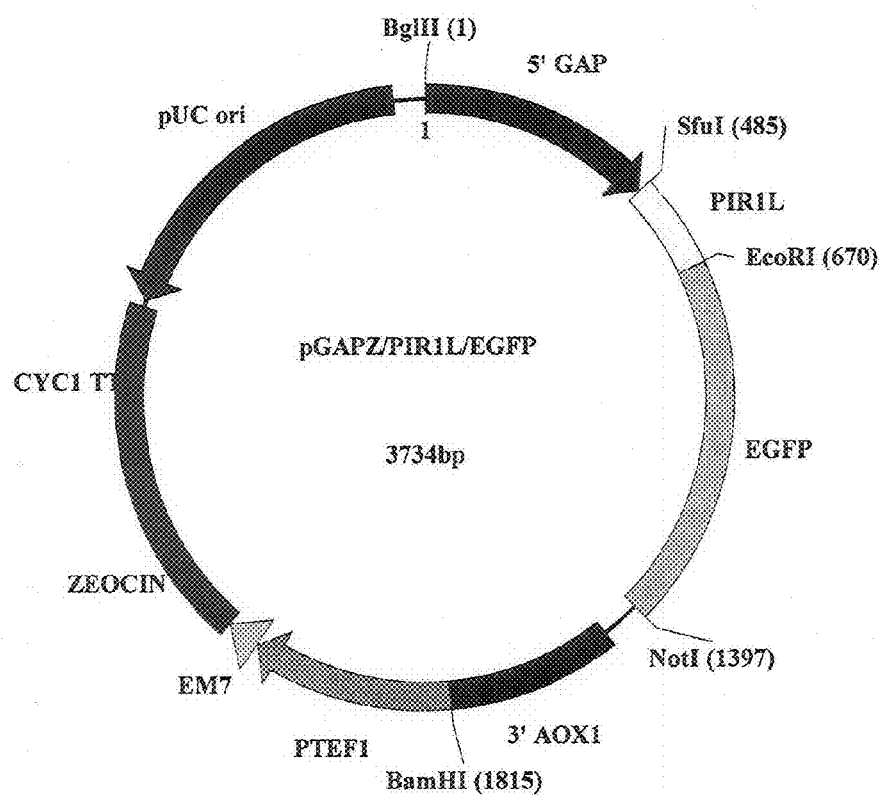

Figure 6. Diagram of the AOX – PpPIR1 anchor domain peptide – EGFP Construct
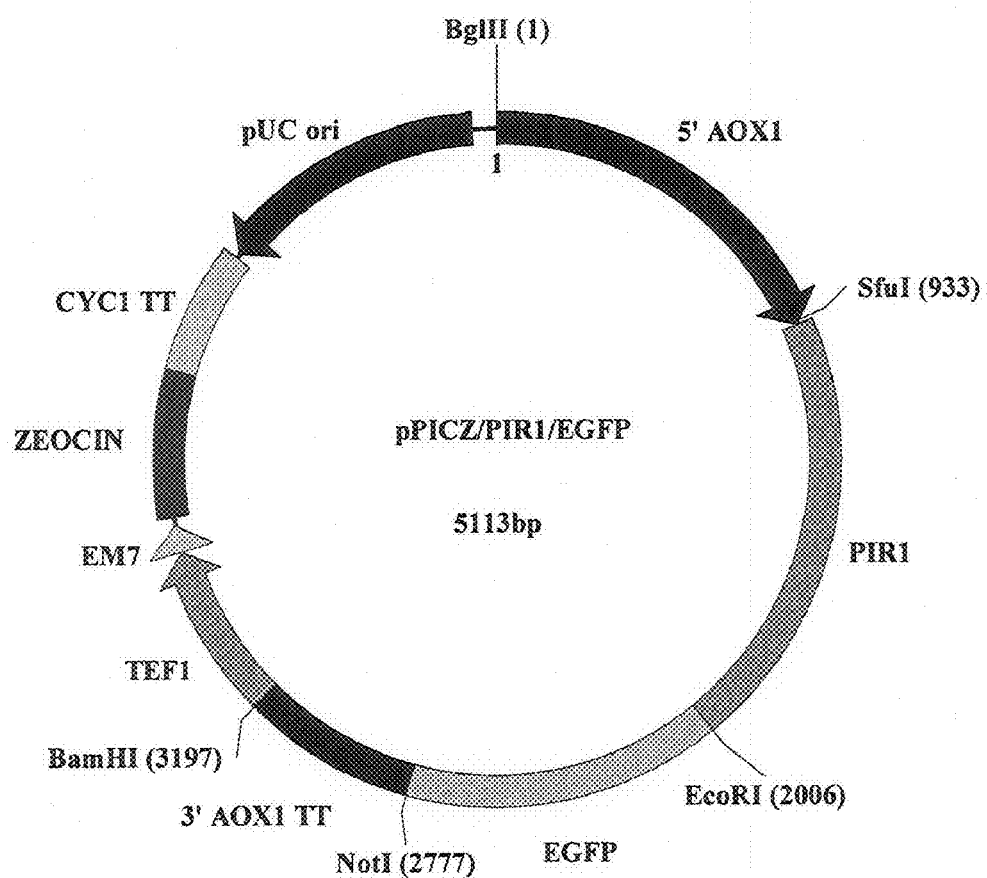

Figure 7. Diagram of the GAP – PpPIR1 anchor domain peptide – EGFP Construct
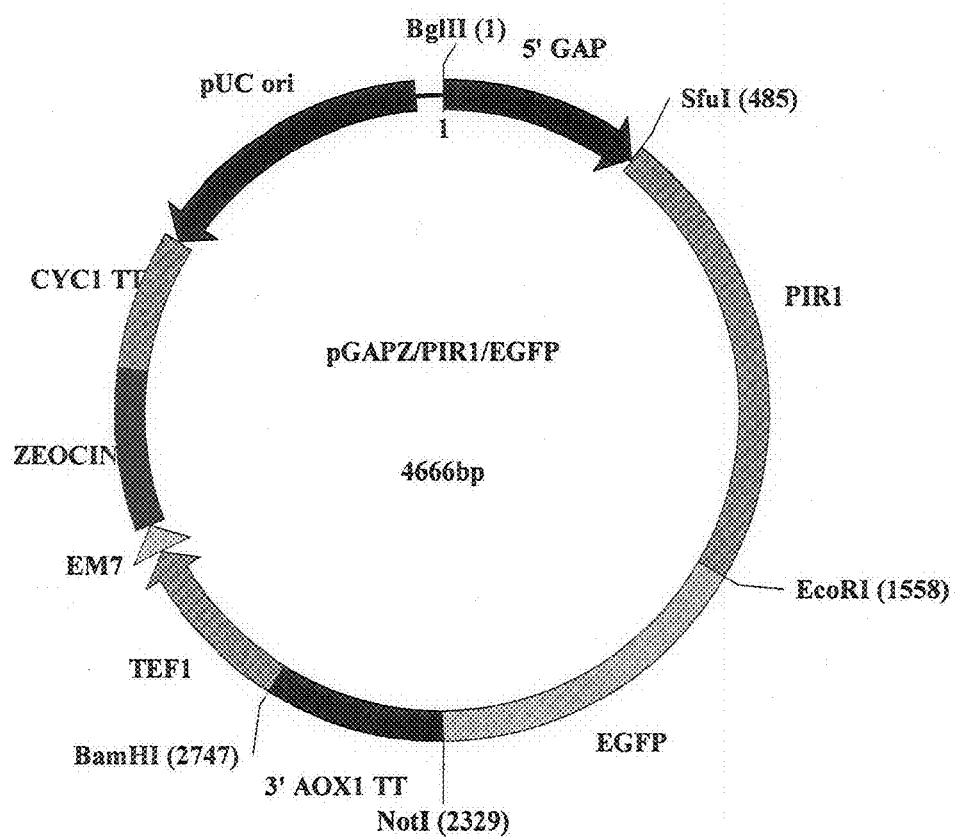

Figure 8. Diagram of the AOX – PpPIR2 anchor domain peptide – EGFP Construct
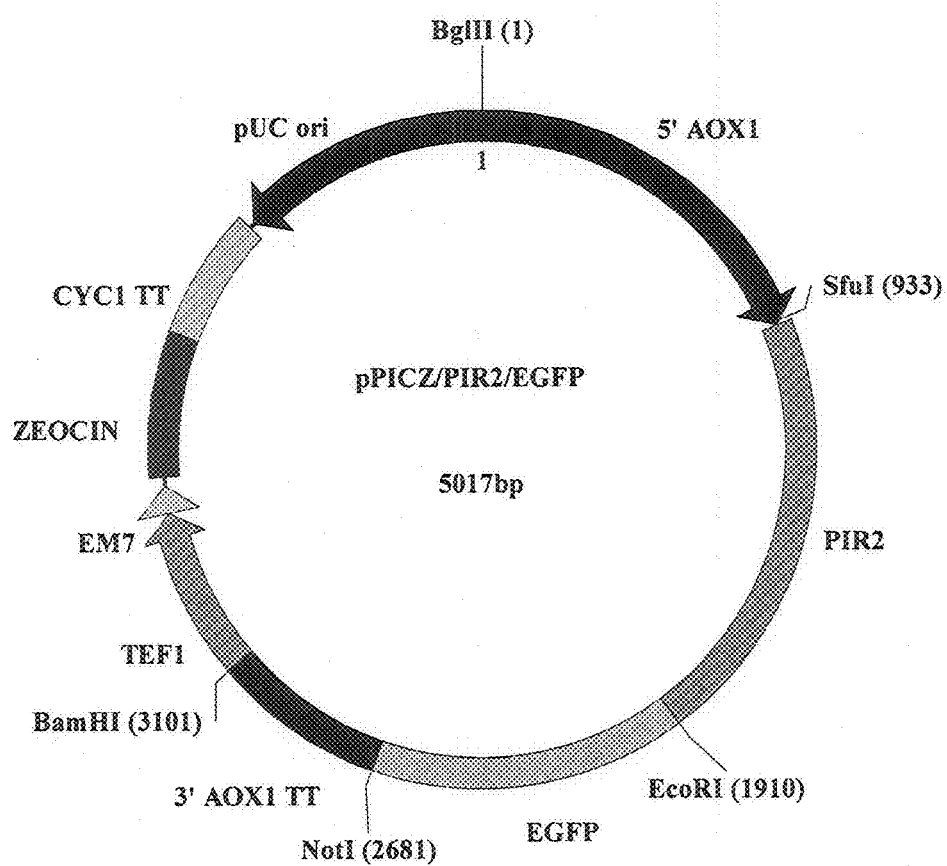

Figure 9. Diagram of the GAP – PpPIR2 anchor domain peptide – EGFP Construct
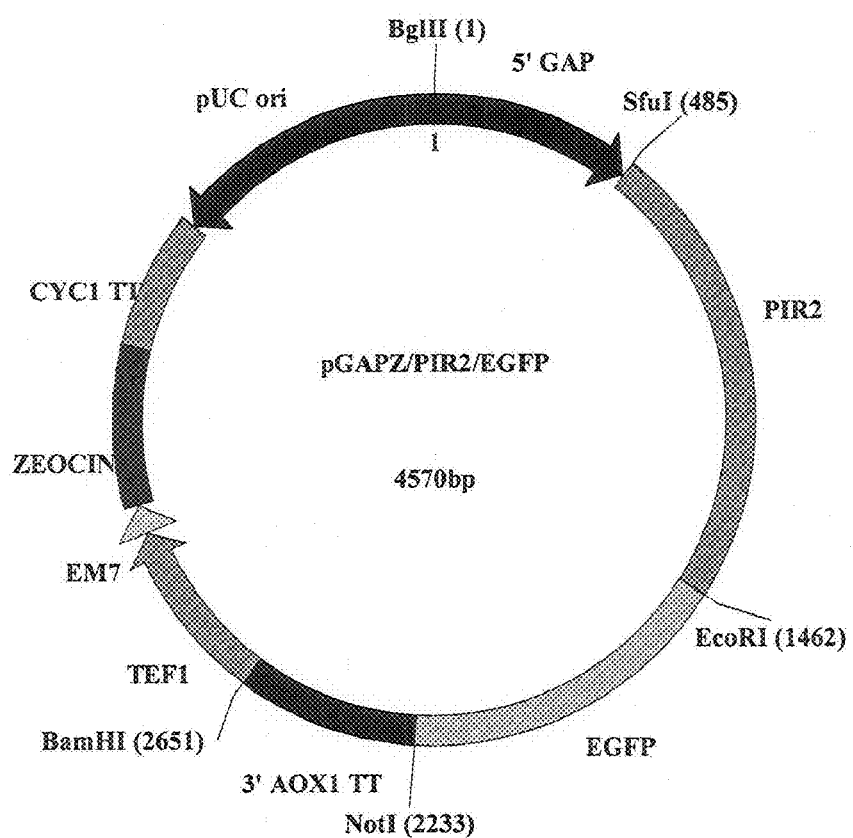

Figure 10. SDS-PAGE analysis of EGFP Expression in Yeast transformed with the AOX1 – PpPIR1 Secretion Signal Peptide – EGFP construct
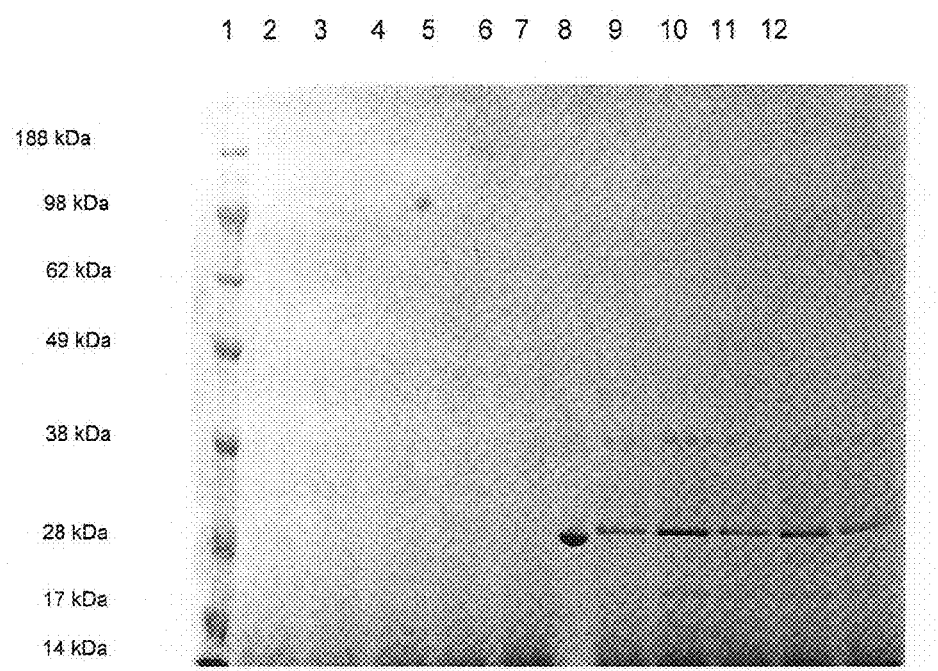

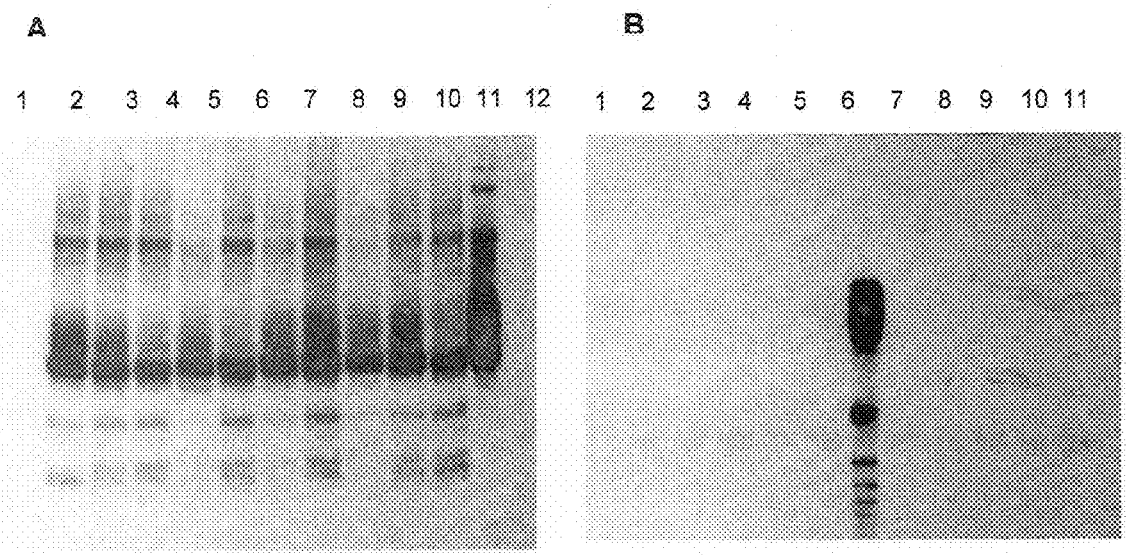
Figure 11. Western analysis of EGFP Expression in Yeast transformed with the AOX1 – PpPIR1 Secretion Signal Peptide – EGFP construct Figure 12. EGFP Surface Display in Yeast transformed with the AOX1 – full length PpPIR1 – EGFP construct
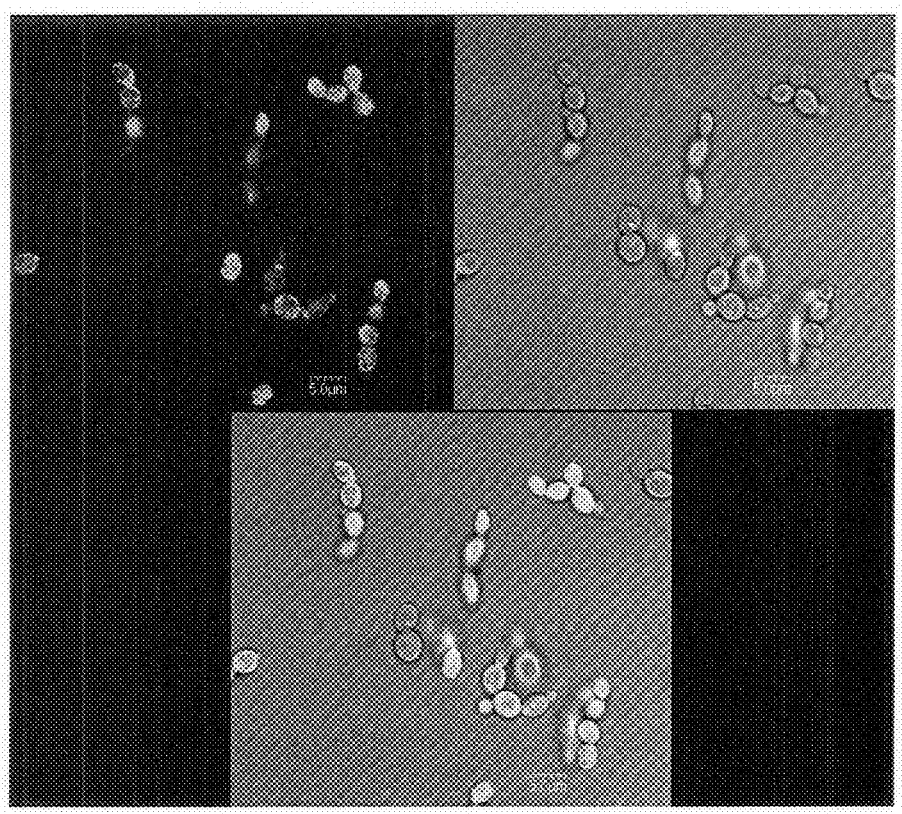

Figure 13. EGFP Surface Display in Yeast transformed with the AOX1 – full length PpPIR1 – EGFP construct
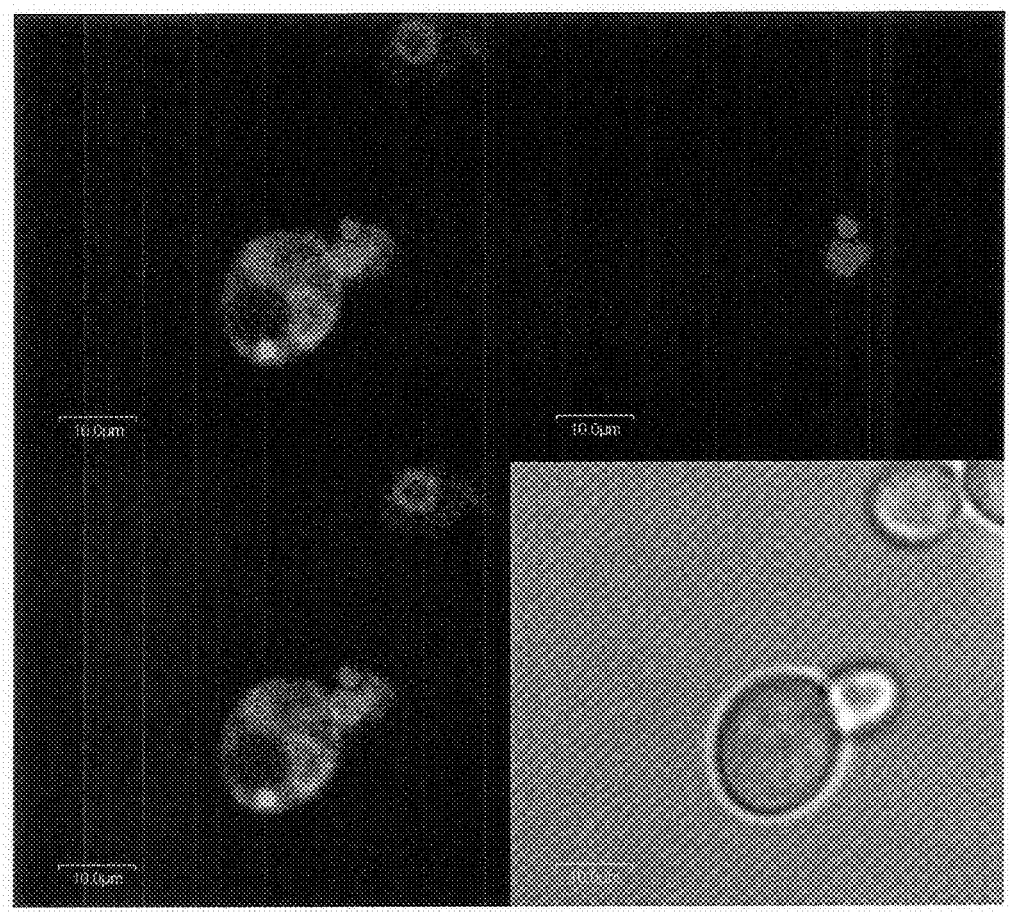

Figure 14. EGFP Surface Display in Yeast transformed with the AOX1 – full length PpPIR2 – EGFP construct
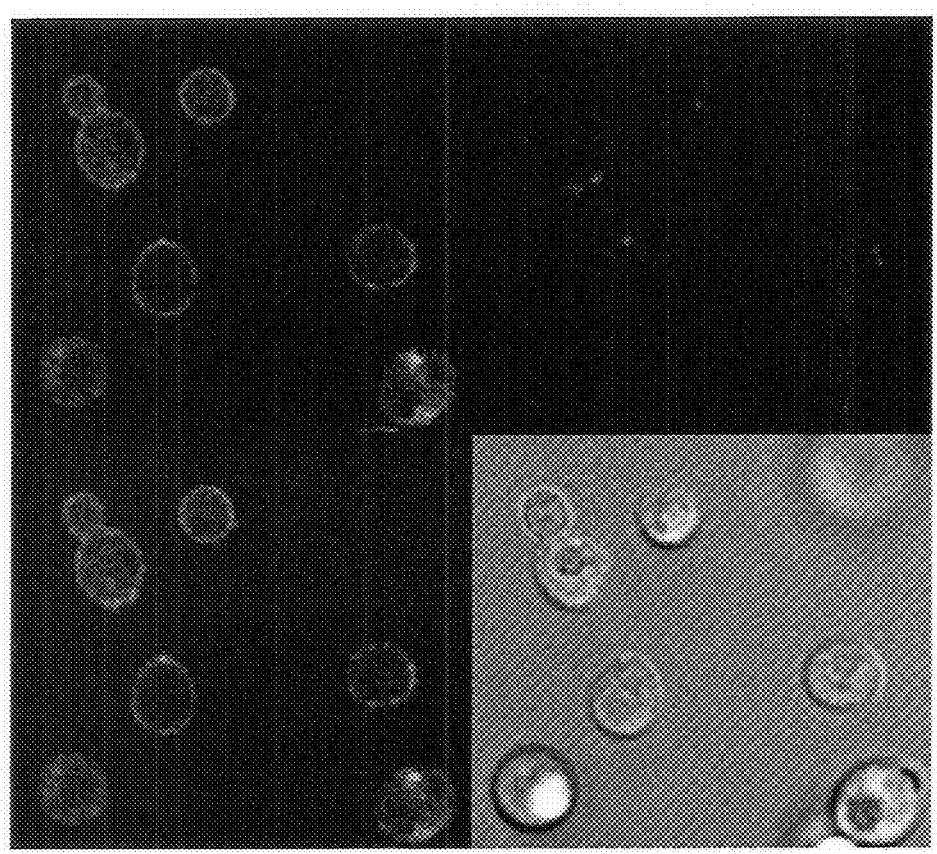

Figure 15. EGFP Surface Display in Yeast transformed with the GAP – full length PpPIR1 – EGFP construct
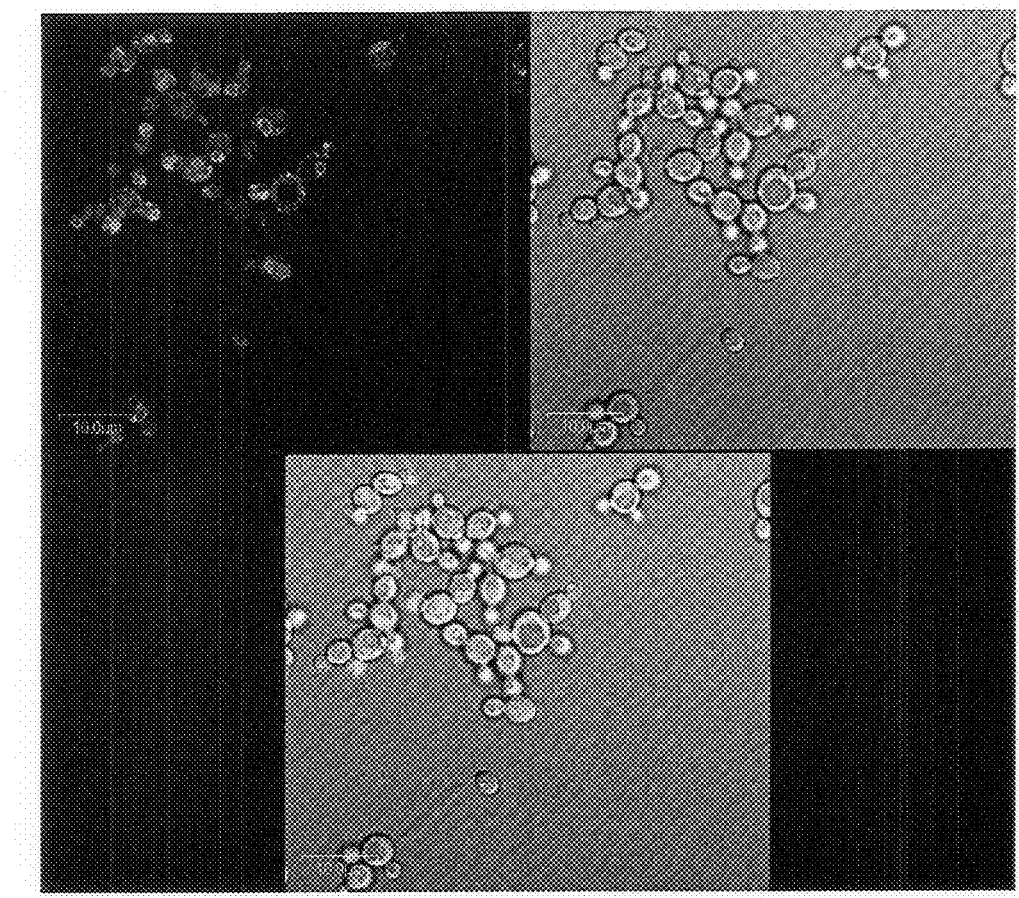

Figure 16. EGFP Display in Yeast transformed with the GAP – full length PpPIR2 – EGFP construct
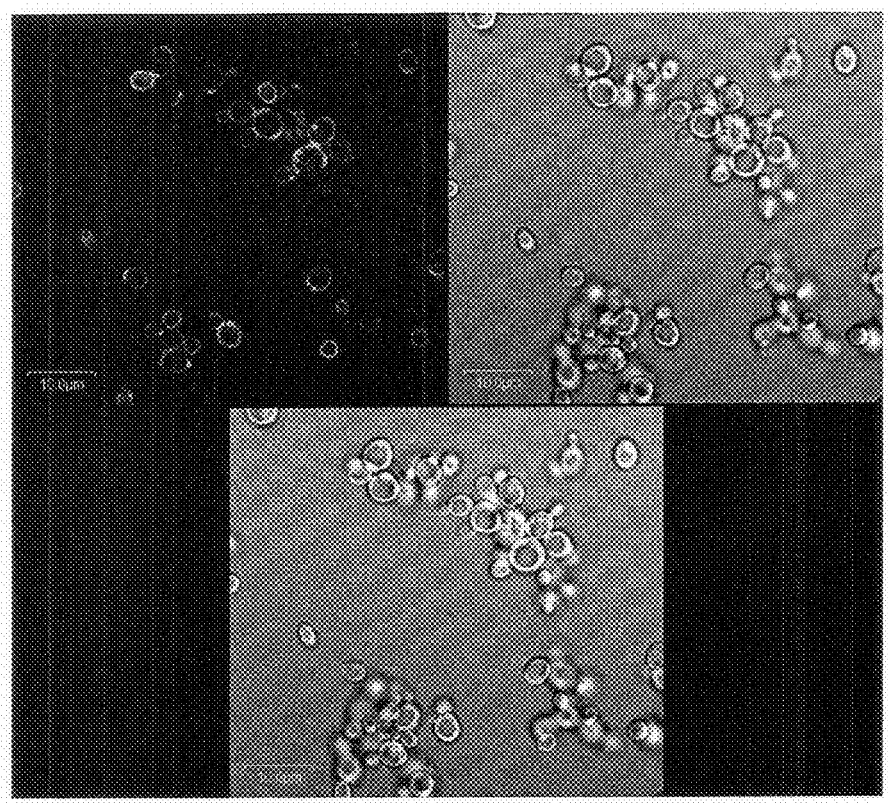

Figure 17. Diagram of the AOX1 – putative PpPIR2 secretion signal peptide – EGFP Construct
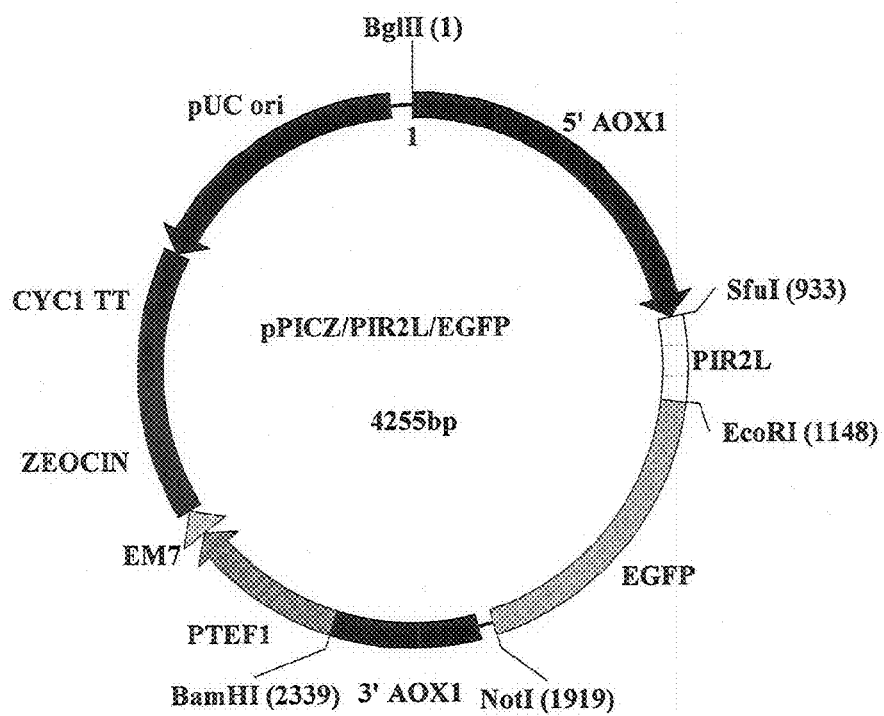

Figure 18. Diagram of the GAP – putative PpPIR2 secretion signal peptide – EGFP Construct
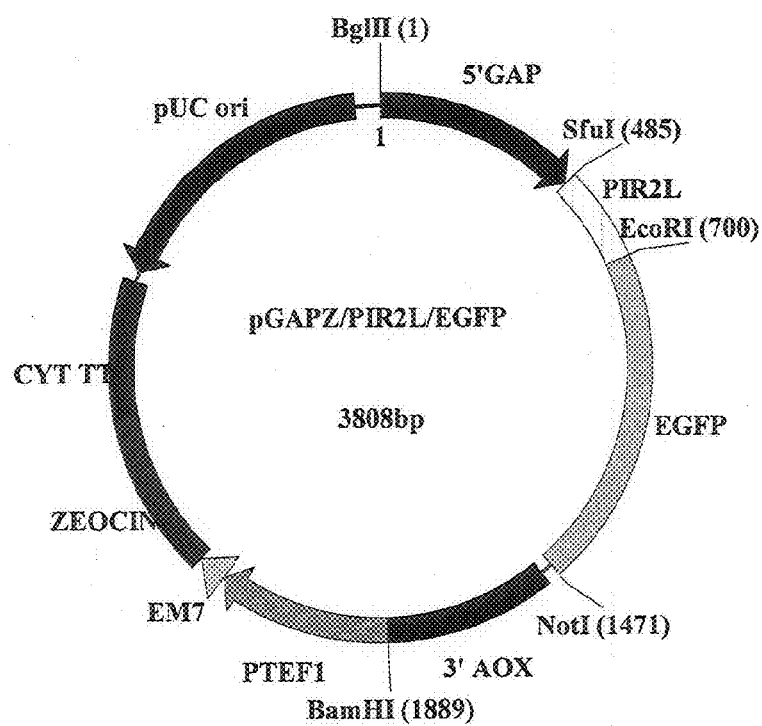

SEQUENCE LISTING

<160> NUMBER OF SEQ ID NOS: 37

<210> SEQ ID NO 1
<211> LENGTH: 1068
<212> TYPE: DNA
<213> ORGANISM: Pichia pastoris

<400> SEQUENCE: 1

```
atgtacagga acttaataat tgctactgcc cttacttgcg gtgcatacag tgcctacgtg      60
ccttccgaac catggagcac actgacacct gatgctagcc ttgaaagtgc cctcaaagat     120
tactcacaaa cttttggaat agctattaag tccttagatg ccgacaagat taagagagag     180
gctgtttccc agattggaga tggacagatt caggcggcta caatcacctc atctgaaccg     240
aaagtaactg cccaagtagt ttcccaaata ggggacggcc aaattcaagc cacgacctcc     300
acttcatcaa atcgaaaga accgctcaa gttgtttccc aaataggtga cggtcaaatt      360
caagccacga cctccacttc atcaaaatcg aagaaaccg ctcaagttgt ttcccaaata     420
ggtgacggtc aaattcaagc cacgacctcc acttcatcaa atcgaaaga accgctcaa      480
gttgtttccc aaataggtga cggtcaaatt caagccacga cctccacttc atcaaaatcg     540
aagaaaccg ctcaagttgt ttcccaaata ggtgacggtc aaattcaagc tacgacctcc      600
acttcatcgg aagtaaaaca aactacagga gttgtctccc aaataggaga tggccagatc     660
caagccacta cagccactac atctgtcgct tctcagattg agacggcca agtgcaggag      720
tcaaaaccaa cggacacatc agaggataaa gggacttctg atttagtgtc ttgccttact     780
gattcttctc ttgctttggt tcttgaaaag ggtgtgctga cagacgctca gggtagaatt     840
ggtgcgattg tggccaatag gcaatttcaa tttgatggac cgccacccca agctggcacc     900
atatatgcag aggatggtc gattacagac gatgctaagc tggcccttgg taacagtaca     960
accttctatc aatgtctttc gggtaccttc tacaatctct atgacgaaaa aattggcgaa    1020
cagtgtgaac cagtcgagtt ggacattgta gacctcatag agtgttaa                1068
```

<210> SEQ ID NO 2
<211> LENGTH: 355
<212> TYPE: PRT
<213> ORGANISM: Pichia pastoris

<400> SEQUENCE: 2

```
Met Tyr Arg Asn Leu Ile Ile Ala Thr Ala Leu Thr Cys Gly Ala Tyr
  1               5                  10                  15

Ser Ala Tyr Val Pro Ser Glu Pro Trp Ser Thr Leu Thr Pro Asp Ala
                 20                  25                  30

Ser Leu Glu Ser Ala Leu Lys Asp Tyr Ser Gln Thr Phe Gly Ile Ala
             35                  40                  45

Ile Lys Ser Leu Asp Ala Asp Lys Ile Lys Arg Glu Ala Val Ser Gln
         50                  55                  60

Ile Gly Asp Gly Gln Ile Gln Ala Ala Thr Ile Thr Ser Ser Glu Pro
 65                  70                  75                  80

Lys Val Thr Ala Gln Val Val Ser Gln Ile Gly Asp Gly Gln Ile Gln
                 85                  90                  95

Ala Thr Thr Ser Thr Ser Ser Lys Ser Lys Glu Thr Ala Gln Val Val
            100                 105                 110

Ser Gln Ile Gly Asp Gly Gln Ile Gln Ala Thr Thr Ser Thr Ser Ser
            115                 120                 125
```

```
Lys Ser Lys Glu Thr Ala Gln Val Val Ser Gln Ile Gly Asp Gly Gln
    130                 135                 140
Ile Gln Ala Thr Thr Ser Thr Ser Ser Lys Ser Lys Glu Thr Ala Gln
145                 150                 155                 160
Val Val Ser Gln Ile Gly Asp Gly Gln Ile Gln Ala Thr Thr Ser Thr
                165                 170                 175
Ser Ser Lys Ser Lys Glu Thr Ala Gln Val Val Ser Gln Ile Gly Asp
            180                 185                 190
Gly Gln Ile Gln Ala Thr Thr Ser Thr Ser Ser Glu Val Lys Gln Thr
        195                 200                 205
Thr Gly Val Val Ser Gln Ile Gly Asp Gly Gln Ile Gln Ala Thr Thr
    210                 215                 220
Ala Thr Thr Ser Val Ala Ser Gln Ile Gly Asp Gly Gln Val Gln Glu
225                 230                 235                 240
Ser Lys Pro Thr Asp Thr Ser Glu Asp Lys Gly Thr Ser Asp Leu Val
                245                 250                 255
Ser Cys Leu Thr Asp Ser Ser Leu Ala Leu Val Leu Glu Lys Gly Val
            260                 265                 270
Leu Thr Asp Ala Gln Gly Arg Ile Gly Ala Ile Val Ala Asn Arg Gln
        275                 280                 285
Phe Gln Phe Asp Gly Pro Pro Gln Ala Gly Thr Ile Tyr Ala Gly
    290                 295                 300
Gly Trp Ser Ile Thr Asp Asp Ala Lys Leu Ala Leu Gly Asn Ser Thr
305                 310                 315                 320
Thr Phe Tyr Gln Cys Leu Ser Gly Thr Phe Tyr Asn Leu Tyr Asp Glu
                325                 330                 335
Lys Ile Gly Glu Gln Cys Glu Pro Val Glu Leu Asp Ile Val Asp Leu
            340                 345                 350
Ile Glu Cys
        355

<210> SEQ ID NO 3
<211> LENGTH: 972
<212> TYPE: DNA
<213> ORGANISM: Pichia pastoris

<400> SEQUENCE: 3
atgaagctcg ctgcactctc cactattgca ttaactattt tacccgttgc cttggctggc    60
tatgctccac ccgatgattg gtcgacccct actgccaaag gagtgtaccc aggtgccttc   120
tcatcctatt ctaatacatt cggtataata gttgaacctt tgacgagctc agtgattta   180 actcctgcta ctacgactca tgttgtttca cagattgatg acggtcaaat tcagcacact   240
aatacagcct atgtaggtac agctcaccaa gttgtgtctc agattggtga cgggcagatt   300
caggctacgg cttctgctgt cccattgcct actgagcttg cttctcaaat tgctgatgga   360
caaatccaag caactactcc tgctggagct cccgccactc cagcttctca gatacaagac   420
ggtcaggttc aagctacttc ttcggctgat gctcacccta ctgcacactc acaagctgaa   480
gacattgggg cccattcttt aagcagcact ggtttgattc ctggtacatt gactactgtc   540
ttgacttcaa ctggaagtga caccacactg acccttgtaa ctgtcgagac tgaagttgtc   600
acttacacac agaagttac agttactgtg aatcggaatg ctgccaaagt gaagagggat   660
aacattgaat ctgcttgctt aaccccacag gcccttggcc taaccctaaa ggattctgtt   720
ttattagatc tccaaggcag agtcggctcc atcgtcgcca atagacaatt ccaattcgat   780
```

-continued

```
ggacctcctc cgcaagccgg tactatttat gctgttggtt ggtccattac gcctaatgga    840
tatctggcat taggtgactc agaagtcttc tatcaatgcc tgtctggttc gttttacaat    900
ctatatgatc agcacattgc tgagcagtgt gaagctgtcc acttgaaggc tgttgatctc    960
atttcatgtt ag                                                        972
```

<210> SEQ ID NO 4
<211> LENGTH: 323
<212> TYPE: PRT
<213> ORGANISM: Pichia pastoris

<400> SEQUENCE: 4

```
Met Lys Leu Ala Ala Leu Ser Thr Ile Ala Leu Thr Ile Leu Pro Val
1               5                   10                  15

Ala Leu Ala Gly Tyr Ala Pro Pro Asp Asp Trp Ser Thr Leu Thr Ala
            20                  25                  30

Lys Gly Val Tyr Pro Gly Ala Phe Ser Ser Tyr Ser Asn Thr Phe Gly
        35                  40                  45

Ile Ile Val Glu Pro Leu Thr Ser Ser Val Ile Leu Thr Pro Ala Thr
    50                  55                  60

Thr Thr His Val Val Ser Gln Ile Asp Asp Gly Gln Ile Gln His Thr
65                  70                  75                  80

Asn Thr Ala Tyr Val Gly Thr Ala His Gln Val Val Ser Gln Ile Gly
                85                  90                  95

Asp Gly Gln Ile Gln Ala Thr Ala Ser Ala Val Pro Leu Pro Thr Glu
            100                 105                 110

Leu Ala Ser Gln Ile Ala Asp Gly Gln Ile Gln Ala Thr Thr Pro Ala
        115                 120                 125

Gly Ala Pro Ala Thr Pro Ala Ser Gln Ile Gln Asp Gly Gln Val Gln
    130                 135                 140

Ala Thr Ser Ser Ala Asp Ala His Pro Thr Ala His Ser Gln Ala Glu
145                 150                 155                 160

Asp Ile Gly Ala His Ser Leu Ser Ser Thr Gly Leu Ile Pro Gly Thr
                165                 170                 175

Leu Thr Thr Val Leu Thr Ser Thr Gly Ser Asp Thr Thr Leu Thr Leu
            180                 185                 190

Val Thr Val Glu Thr Glu Val Val Thr Tyr Thr Pro Glu Val Thr Val
        195                 200                 205

Thr Val Asn Arg Asn Ala Ala Lys Val Lys Arg Asp Asn Ile Glu Ser
    210                 215                 220

Ala Cys Leu Thr Pro Gln Ala Leu Gly Leu Thr Leu Lys Asp Ser Val
225                 230                 235                 240

Leu Leu Asp Leu Gln Gly Arg Val Gly Ser Ile Val Ala Asn Arg Gln
                245                 250                 255

Phe Gln Phe Asp Gly Pro Pro Gln Ala Gly Thr Ile Tyr Ala Val
            260                 265                 270

Gly Trp Ser Ile Thr Pro Asn Gly Tyr Leu Ala Leu Gly Asp Ser Glu
        275                 280                 285

Val Phe Tyr Gln Cys Leu Ser Gly Ser Phe Tyr Asn Leu Tyr Asp Gln
    290                 295                 300

His Ile Ala Glu Gln Cys Glu Ala Val His Leu Lys Ala Val Asp Leu
305                 310                 315                 320

Ile Ser Cys
```

-continued

<210> SEQ ID NO 5
<211> LENGTH: 26
<212> TYPE: DNA
<213> ORGANISM: Artificial Sequence
<220> FEATURE:
<223> OTHER INFORMATION: Synthetic

<400> SEQUENCE: 5
atgtacagga acttaataat tgctac                                26

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
ttaacactct atgaggtcta c                                     21

<210> SEQ ID NO 7
<211> LENGTH: 29
<212> TYPE: DNA
<213> ORGANISM: Artificial Sequence
<220> FEATURE:
<223> OTHER INFORMATION: Synthetic

<400> SEQUENCE: 7
gggaattctc tcttaatctt gtcggcatc                             29

<210> SEQ ID NO 8
<211> LENGTH: 34
<212> TYPE: DNA
<213> ORGANISM: Artificial Sequence
<220> FEATURE:
<223> OTHER INFORMATION: Synthetic

<400> SEQUENCE: 8
tattcgaaac gatgtacagg aacttaataa ttgc                       34

<210> SEQ ID NO 9
<211> LENGTH: 31
<212> TYPE: DNA
<213> ORGANISM: Artificial Sequence
<220> FEATURE:
<223> OTHER INFORMATION: Synthetic

<400> SEQUENCE: 9
aaagaattca cactctatga ggtctacaat g                          31

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
ccatatccag aagtatcaga tg                                    22

<210> SEQ ID NO 11
<211> LENGTH: 19
<212> TYPE: DNA
<213> ORGANISM: Artificial Sequence
<220> FEATURE:
<223> OTHER INFORMATION: Synthetic

<400> SEQUENCE: 11
actgtgattc gccttcagg                                                    19

<210> SEQ ID NO 12
<211> LENGTH: 31
<212> TYPE: DNA
<213> ORGANISM: Artificial Sequence
<220> FEATURE:
<223> OTHER INFORMATION: Synthetic

<400> SEQUENCE: 12
tattcgaaac gatgaagctc gctgcactct c                                      31

<210> SEQ ID NO 13
<211> LENGTH: 28
<212> TYPE: DNA
<213> ORGANISM: Artificial Sequence
<220> FEATURE:
<223> OTHER INFORMATION: Synthetic

<400> SEQUENCE: 13
gggaattcac atgaaatgag atcaacag                                          28

<210> SEQ ID NO 14
<211> LENGTH: 177
<212> TYPE: DNA
<213> ORGANISM: Artificial Sequence
<220> FEATURE:
<223> OTHER INFORMATION: Synthetic

<400> SEQUENCE: 14
atgtacagga acttaataat tgctactgcc cttacttgcg gtgcatacag tgcctacgtg        60
ccttccgaac catggagcac actgacacct gatgctagcc ttgaaagtgc cctcaaagat       120
tactcacaaa cttttggaat agctattaag tccttagatg ccgacaagat taagaga         177

<210> SEQ ID NO 15
<211> LENGTH: 59
<212> TYPE: PRT
<213> ORGANISM: Artificial Sequence
<220> FEATURE:
<223> OTHER INFORMATION: Synthetic

<400> SEQUENCE: 15

Met Tyr Arg Asn Leu Ile Ile Ala Thr Ala Leu Thr Cys Gly Ala Tyr
1               5                   10                  15

Ser Ala Tyr Val Pro Ser Glu Pro Trp Ser Thr Leu Thr Pro Asp Ala
            20                  25                  30

Ser Leu Glu Ser Ala Leu Lys Asp Tyr Ser Gln Thr Phe Gly Ile Ala
        35                  40                  45

Ile Lys Ser Leu Asp Ala Asp Lys Ile Lys Arg
    50                  55

<210> SEQ ID NO 16
<211> LENGTH: 296
<212> TYPE: PRT
<213> ORGANISM: Artificial Sequence
<220> FEATURE:
<223> OTHER INFORMATION: Synthetic

<400> SEQUENCE: 16

Glu Ala Val Ser Gln Ile Gly Asp Gly Gln Ile Gln Ala Ala Thr Ile
1               5                   10                  15

-continued

```
Thr Ser Ser Glu Pro Lys Val Thr Ala Gln Val Ser Gln Ile Gly
             20                  25                  30

Asp Gly Gln Ile Gln Ala Thr Thr Ser Thr Ser Lys Ser Lys Glu
         35                  40                  45

Thr Ala Gln Val Val Ser Gln Ile Gly Asp Gly Gln Ile Gln Ala Thr
 50                  55                  60

Thr Ser Thr Ser Ser Lys Ser Lys Glu Thr Ala Gln Val Val Ser Gln
 65                  70                  75                  80

Ile Gly Asp Gly Gln Ile Gln Ala Thr Thr Ser Thr Ser Ser Lys Ser
                 85                  90                  95

Lys Glu Thr Ala Gln Val Val Ser Gln Ile Gly Asp Gly Gln Ile Gln
            100                 105                 110

Ala Thr Thr Ser Thr Ser Ser Lys Ser Lys Glu Thr Ala Gln Val Val
            115                 120                 125

Ser Gln Ile Gly Asp Gly Gln Ile Gln Ala Thr Thr Ser Thr Ser Ser
        130                 135                 140

Glu Val Lys Gln Thr Thr Gly Val Val Ser Gln Ile Gly Asp Gly Gln
145                 150                 155                 160

Ile Gln Ala Thr Thr Ala Thr Ser Val Ala Ser Gln Ile Gly Asp
                165                 170                 175

Gly Gln Val Gln Glu Ser Lys Pro Thr Asp Thr Ser Glu Asp Lys Gly
            180                 185                 190

Thr Ser Asp Leu Val Ser Cys Leu Thr Asp Ser Ser Leu Ala Leu Val
        195                 200                 205

Leu Glu Lys Gly Val Leu Thr Asp Ala Gln Gly Arg Ile Gly Ala Ile
210                 215                 220

Val Ala Asn Arg Gln Phe Gln Phe Asp Gly Pro Pro Gln Ala Gly
225                 230                 235                 240

Thr Ile Tyr Ala Gly Gly Trp Ser Ile Thr Asp Asp Ala Lys Leu Ala
                245                 250                 255

Leu Gly Asn Ser Thr Thr Phe Tyr Gln Cys Leu Ser Gly Thr Phe Tyr
            260                 265                 270

Asn Leu Tyr Asp Glu Lys Ile Gly Glu Gln Cys Glu Pro Val Glu Leu
        275                 280                 285

Asp Ile Val Asp Leu Ile Glu Cys
        290                 295

<210> SEQ ID NO 17
<211> LENGTH: 69
<212> TYPE: PRT
<213> ORGANISM: Artificial Sequence
<220> FEATURE:
<223> OTHER INFORMATION: Synthetic

<400> SEQUENCE: 17

Met Lys Leu Ala Ala Leu Ser Thr Ile Ala Leu Thr Ile Leu Pro Val
  1               5                  10                  15

Ala Leu Ala Gly Tyr Ala Pro Pro Asp Asp Trp Ser Thr Leu Thr Ala
             20                  25                  30

Lys Gly Val Tyr Pro Gly Ala Phe Ser Ser Tyr Ser Asn Thr Phe Gly
         35                  40                  45

Ile Ile Val Glu Pro Leu Thr Ser Ser Val Ile Leu Thr Pro Ala Thr
 50                  55                  60

Thr Thr His Val Val
 65
```

<210> SEQ ID NO 18
<211> LENGTH: 257
<212> TYPE: PRT
<213> ORGANISM: Artificial Sequence
<220> FEATURE:
<223> OTHER INFORMATION: Synthetic

<400> SEQUENCE: 18

```
His Val Val Ser Gln Ile Asp Asp Gly Gln Ile Gln His Thr Asn Thr
1               5                   10                  15

Ala Tyr Val Gly Thr Ala His Gln Val Ser Gln Ile Gly Asp Gly
            20                  25                  30

Gln Ile Gln Ala Thr Ala Ser Ala Val Pro Leu Pro Thr Glu Leu Ala
        35                  40                  45

Ser Gln Ile Ala Asp Gly Gln Ile Gln Ala Thr Thr Pro Ala Gly Ala
    50                  55                  60

Pro Ala Thr Pro Ala Ser Gln Ile Gln Asp Gly Gln Val Gln Ala Thr
65                  70                  75                  80

Ser Ser Ala Asp Ala His Pro Thr Ala His Ser Gln Ala Glu Asp Ile
                85                  90                  95

Gly Ala His Ser Leu Ser Ser Thr Gly Leu Ile Pro Gly Thr Leu Thr
            100                 105                 110

Thr Val Leu Thr Ser Thr Gly Ser Asp Thr Thr Leu Thr Leu Val Thr
        115                 120                 125

Val Glu Thr Glu Val Val Thr Tyr Thr Pro Glu Val Thr Val Thr Val
    130                 135                 140

Asn Arg Asn Ala Ala Lys Val Lys Arg Asp Asn Ile Glu Ser Ala Cys
145                 150                 155                 160

Leu Thr Pro Gln Ala Leu Gly Leu Thr Leu Lys Asp Ser Val Leu Leu
                165                 170                 175

Asp Leu Gln Gly Arg Val Gly Ser Ile Val Ala Asn Arg Gln Phe Gln
            180                 185                 190

Phe Asp Gly Pro Pro Gln Ala Gly Thr Ile Tyr Ala Val Gly Trp
        195                 200                 205

Ser Ile Thr Pro Asn Gly Tyr Leu Ala Leu Gly Asp Ser Glu Val Phe
    210                 215                 220

Tyr Gln Cys Leu Ser Gly Ser Phe Tyr Asn Leu Tyr Asp Gln His Ile
225                 230                 235                 240

Ala Glu Gln Cys Glu Ala Val His Leu Lys Ala Val Asp Leu Ile Ser
                245                 250                 255

Cys
```

<210> SEQ ID NO 19
<211> LENGTH: 341
<212> TYPE: PRT
<213> ORGANISM: Saccharomyces cerevisiae

<400> SEQUENCE: 19

```
Met Gln Tyr Lys Lys Ser Leu Val Ala Ser Ala Leu Val Ala Thr Ser
1               5                   10                  15

Leu Ala Ala Tyr Ala Pro Lys Asp Pro Trp Ser Thr Leu Thr Pro Ser
            20                  25                  30

Ala Thr Tyr Lys Gly Gly Ile Thr Asp Tyr Ser Ser Thr Phe Gly Ile
        35                  40                  45

Ala Val Glu Pro Ile Ala Thr Thr Ala Ser Ser Lys Ala Lys Arg Ala
```

```
                50                  55                  60
Ala Ala Ile Ser Gln Ile Gly Asp Gly Gln Ile Gln Ala Thr Thr Lys
 65                  70                  75                  80

Thr Thr Ala Ala Ala Val Ser Gln Ile Gly Asp Gly Gln Ile Gln Ala
                 85                  90                  95

Thr Thr Lys Thr Lys Ala Ala Ala Val Ser Gln Ile Gly Asp Gly Gln
            100                 105                 110

Ile Gln Ala Thr Thr Lys Thr Thr Ser Ala Lys Thr Thr Ala Ala Ala
            115                 120                 125

Val Ser Gln Ile Gly Asp Gly Gln Ile Gln Ala Thr Thr Lys Thr Lys
        130                 135                 140

Ala Ala Ala Val Ser Gln Ile Gly Asp Gly Gln Ile Gln Ala Thr Thr
145                 150                 155                 160

Lys Thr Thr Ala Ala Ala Val Ser Gln Ile Gly Asp Gly Gln Ile Gln
                165                 170                 175

Ala Thr Thr Lys Thr Thr Ala Ala Ala Val Ser Gln Ile Gly Asp Gly
            180                 185                 190

Gln Ile Gln Ala Thr Thr Asn Thr Thr Val Ala Pro Val Ser Gln Ile
        195                 200                 205

Thr Asp Gly Gln Ile Gln Ala Thr Thr Leu Thr Ser Ala Thr Ile Ile
    210                 215                 220

Pro Ser Pro Ala Pro Ala Pro Ile Thr Asn Gly Thr Asp Pro Val Thr
225                 230                 235                 240

Ala Glu Thr Cys Lys Ser Ser Gly Thr Leu Glu Met Asn Leu Lys Gly
                245                 250                 255

Gly Ile Leu Thr Asp Gly Lys Gly Arg Ile Gly Ser Ile Val Ala Asn
                260                 265                 270

Arg Gln Phe Gln Phe Asp Gly Pro Pro Gln Ala Gly Ala Ile Tyr
            275                 280                 285

Ala Ala Gly Trp Ser Ile Thr Pro Glu Gly Asn Leu Ala Ile Gly Asp
        290                 295                 300

Gln Asp Thr Phe Tyr Gln Cys Leu Ser Gly Asn Phe Tyr Asn Leu Tyr
305                 310                 315                 320

Asp Glu His Ile Gly Thr Gln Cys Asn Ala Val His Leu Gln Ala Ile
                325                 330                 335

Asp Leu Leu Asn Cys
            340

<210> SEQ ID NO 20
<211> LENGTH: 63
<212> TYPE: PRT
<213> ORGANISM: Artificial Sequence
<220> FEATURE:
<223> OTHER INFORMATION: Synthetic

<400> SEQUENCE: 20

Met Gln Tyr Lys Lys Ser Leu Val Ala Ser Ala Leu Val Ala Thr Ser
 1               5                  10                  15

Leu Ala Ala Tyr Ala Pro Lys Asp Pro Trp Ser Thr Leu Thr Pro Ser
             20                  25                  30

Ala Thr Tyr Lys Gly Gly Ile Thr Asp Tyr Ser Ser Thr Phe Gly Ile
         35                  40                  45

Ala Val Glu Pro Ile Ala Thr Thr Ala Ser Ser Lys Ala Lys Arg
     50                  55                  60
```

-continued

```
<210> SEQ ID NO 21
<211> LENGTH: 278
<212> TYPE: PRT
<213> ORGANISM: Artificial Sequence
<220> FEATURE:
<223> OTHER INFORMATION: Synthetic

<400> SEQUENCE: 21

Ala Ala Ala Ile Ser Gln Ile Gly Asp Gly Gln Ile Gln Ala Thr Thr
1               5                   10                  15

Lys Thr Thr Ala Ala Ala Val Ser Gln Ile Gly Asp Gly Gln Ile Gln
            20                  25                  30

Ala Thr Thr Lys Thr Lys Ala Ala Val Ser Gln Ile Gly Asp Gly
        35                  40                  45

Gln Ile Gln Ala Thr Thr Lys Thr Thr Ser Ala Lys Thr Thr Ala Ala
    50                  55                  60

Ala Val Ser Gln Ile Gly Asp Gly Gln Ile Gln Ala Thr Thr Lys Thr
65                  70                  75                  80

Lys Ala Ala Val Ser Gln Ile Gly Asp Gly Gln Ile Gln Ala Thr
                85                  90                  95

Thr Lys Thr Thr Ala Ala Ala Val Ser Gln Ile Gly Asp Gly Gln Ile
            100                 105                 110

Gln Ala Thr Thr Lys Thr Thr Ala Ala Ala Val Ser Gln Ile Gly Asp
        115                 120                 125

Gly Gln Ile Gln Ala Thr Thr Asn Thr Thr Val Ala Pro Val Ser Gln
130                 135                 140

Ile Thr Asp Gly Gln Ile Gln Ala Thr Thr Leu Thr Ser Ala Thr Ile
145                 150                 155                 160

Ile Pro Ser Pro Ala Pro Ala Pro Ile Thr Asn Gly Thr Asp Pro Val
                165                 170                 175

Thr Ala Glu Thr Cys Lys Ser Ser Gly Thr Leu Glu Met Asn Leu Lys
            180                 185                 190

Gly Gly Ile Leu Thr Asp Gly Lys Gly Arg Ile Gly Ser Ile Val Ala
        195                 200                 205

Asn Arg Gln Phe Gln Phe Asp Gly Pro Pro Gln Ala Gly Ala Ile
    210                 215                 220

Tyr Ala Ala Gly Trp Ser Ile Thr Pro Glu Gly Asn Leu Ala Ile Gly
225                 230                 235                 240

Asp Gln Asp Thr Phe Tyr Gln Cys Leu Ser Gly Asn Phe Tyr Asn Leu
                245                 250                 255

Tyr Asp Glu His Ile Gly Thr Gln Cys Asn Ala Val His Leu Gln Ala
            260                 265                 270

Ile Asp Leu Leu Asn Cys
        275

<210> SEQ ID NO 22
<211> LENGTH: 413
<212> TYPE: PRT
<213> ORGANISM: Saccharomyces cerevisiae

<400> SEQUENCE: 22

Met Gln Tyr Lys Lys Thr Leu Val Ala Ser Ala Leu Ala Ala Thr Thr
1               5                   10                  15

Leu Ala Ala Tyr Ala Pro Ser Glu Pro Trp Ser Thr Leu Thr Pro Thr
            20                  25                  30

Ala Thr Tyr Ser Gly Gly Val Asp Tyr Ala Ser Thr Phe Gly Ile
        35                  40                  45
```

```
Ala Val Gln Pro Ile Ser Thr Thr Ser Ser Ala Ser Ser Ala Ala Thr
 50                  55                  60

Thr Ala Ser Ser Lys Ala Lys Arg Ala Ala Ser Gln Ile Gly Asp Gly
 65                  70                  75                  80

Gln Val Gln Ala Ala Thr Thr Ala Ser Val Ser Thr Lys Ser Thr
                 85                  90                  95

Ala Ala Ala Val Ser Gln Ile Gly Asp Gly Gln Ile Ala Thr Thr
                100                 105                 110

Lys Thr Thr Ala Ala Ala Val Ser Gln Ile Gly Asp Gly Gln Ile Gln
                115                 120                 125

Ala Thr Thr Lys Thr Thr Ser Ala Lys Thr Thr Ala Ala Val Ser
                130                 135                 140

Gln Ile Ser Asp Gly Gln Ile Gln Ala Thr Thr Thr Thr Leu Ala Pro
145                 150                 155                 160

Lys Ser Thr Ala Ala Val Ser Gln Ile Gly Asp Gly Gln Val Gln
                165                 170                 175

Ala Thr Thr Thr Thr Leu Ala Pro Lys Ser Thr Ala Ala Ala Val Ser
                180                 185                 190

Gln Ile Gly Asp Gly Gln Val Gln Ala Thr Thr Lys Thr Thr Ala Ala
                195                 200                 205

Ala Val Ser Gln Ile Gly Asp Gly Gln Val Gln Ala Thr Thr Lys Thr
 210                 215                 220

Thr Ala Ala Ala Val Ser Gln Ile Gly Asp Gly Gln Val Gln Ala Thr
225                 230                 235                 240

Thr Lys Thr Thr Ala Ala Ala Val Ser Gln Ile Gly Asp Gly Gln Val
                245                 250                 255

Gln Ala Thr Thr Lys Thr Thr Ala Ala Ala Val Ser Gln Ile Thr Asp
                260                 265                 270

Gly Gln Val Gln Ala Thr Thr Lys Thr Thr Gln Ala Ala Ser Gln Val
                275                 280                 285

Ser Asp Gly Gln Val Gln Ala Thr Thr Ala Thr Ser Ala Ser Ala Ala
 290                 295                 300

Ala Thr Ser Thr Asp Pro Val Asp Ala Val Ser Cys Lys Thr Ser Gly
305                 310                 315                 320

Thr Leu Glu Met Asn Leu Lys Gly Gly Ile Leu Thr Asp Gly Lys Gly
                325                 330                 335

Arg Ile Gly Ser Ile Val Ala Asn Arg Gln Phe Gln Phe Asp Gly Pro
                340                 345                 350

Pro Pro Gln Ala Gly Ala Ile Tyr Ala Ala Gly Trp Ser Ile Thr Pro
                355                 360                 365

Asp Gly Asn Leu Ala Ile Gly Asp Asn Asp Val Phe Tyr Gln Cys Leu
 370                 375                 380

Ser Gly Thr Phe Tyr Asn Leu Tyr Asp Glu His Ile Gly Ser Gln Cys
385                 390                 395                 400

Thr Pro Val His Leu Glu Ala Ile Asp Leu Ile Asp Cys
                405                 410
```

<210> SEQ ID NO 23
<211> LENGTH: 72
<212> TYPE: PRT
<213> ORGANISM: Artificial Sequence
<220> FEATURE:
<223> OTHER INFORMATION: Synthetic

<400> SEQUENCE: 23

```
Met Gln Tyr Lys Lys Thr Leu Val Ala Ser Ala Leu Ala Ala Thr Thr
1               5                   10                  15

Leu Ala Ala Tyr Ala Pro Ser Glu Pro Trp Ser Thr Leu Thr Pro Thr
                20                  25                  30

Ala Thr Tyr Ser Gly Gly Val Thr Asp Tyr Ala Ser Thr Phe Gly Ile
                35                  40                  45

Ala Val Gln Pro Ile Ser Thr Thr Ser Ser Ala Ser Ala Ala Thr
    50                  55                  60

Thr Ala Ser Ser Lys Ala Lys Arg
65                  70
```

<210> SEQ ID NO 24
<211> LENGTH: 341
<212> TYPE: PRT
<213> ORGANISM: Artificial Sequence
<220> FEATURE:
<223> OTHER INFORMATION: Synthetic

<400> SEQUENCE: 24

```
Ala Ala Ser Gln Ile Gly Asp Gly Gln Val Gln Ala Thr Thr Thr
1               5                   10                  15

Ala Ser Val Ser Thr Lys Ser Thr Ala Ala Val Ser Gln Ile Gly
                20                  25                  30

Asp Gly Gln Ile Gln Ala Thr Thr Lys Thr Thr Ala Ala Val Ser
                35                  40                  45

Gln Ile Gly Asp Gly Gln Ile Gln Ala Thr Thr Lys Thr Thr Ser Ala
    50                  55                  60

Lys Thr Thr Ala Ala Val Ser Gln Ile Ser Asp Gly Gln Ile Gln
65                  70                  75                  80

Ala Thr Thr Thr Thr Leu Ala Pro Lys Ser Thr Ala Ala Val Ser
                85                  90                  95

Gln Ile Gly Asp Gly Val Gln Ala Thr Thr Thr Leu Ala Pro
                100                 105                 110

Lys Ser Thr Ala Ala Val Ser Gln Ile Gly Asp Gly Gln Val Gln
                115                 120                 125

Ala Thr Thr Lys Thr Thr Ala Ala Ala Val Ser Gln Ile Gly Asp Gly
    130                 135                 140

Gln Val Gln Ala Thr Thr Lys Thr Thr Ala Ala Val Ser Gln Ile
145                 150                 155                 160

Gly Asp Gly Gln Val Gln Ala Thr Thr Lys Thr Thr Ala Ala Val
                165                 170                 175

Ser Gln Ile Gly Asp Gly Gln Val Gln Ala Thr Thr Lys Thr Ala
                180                 185                 190

Ala Ala Val Ser Gln Ile Thr Asp Gly Gln Val Gln Ala Thr Thr Lys
    195                 200                 205

Thr Thr Gln Ala Ala Ser Gln Val Ser Asp Gly Gln Val Gln Ala Thr
    210                 215                 220

Thr Ala Thr Ser Ala Ser Ala Ala Thr Ser Thr Asp Pro Val Asp
225                 230                 235                 240

Ala Val Ser Cys Lys Thr Ser Gly Thr Leu Glu Met Asn Leu Lys Gly
                245                 250                 255

Gly Ile Leu Thr Asp Gly Lys Gly Arg Ile Gly Ser Ile Val Ala Asn
                260                 265                 270

Arg Gln Phe Gln Phe Asp Gly Pro Pro Gln Ala Gly Ala Ile Tyr
                275                 280                 285
```

```
Ala Ala Gly Trp Ser Ile Thr Pro Asp Gly Asn Leu Ala Ile Gly Asp
        290                 295                 300

Asn Asp Val Phe Tyr Gln Cys Leu Ser Gly Thr Phe Tyr Asn Leu Tyr
305                 310                 315                 320

Asp Glu His Ile Gly Ser Gln Cys Thr Pro Val His Leu Glu Ala Ile
                325                 330                 335

Asp Leu Ile Asp Cys
            340

<210> SEQ ID NO 25
<211> LENGTH: 325
<212> TYPE: PRT
<213> ORGANISM: Saccharomyces cerevisiae

<400> SEQUENCE: 25

Met Gln Tyr Lys Lys Pro Leu Val Val Ser Ala Leu Ala Ala Thr Ser
1               5                   10                  15

Leu Ala Ala Tyr Ala Pro Lys Asp Pro Trp Ser Thr Leu Thr Pro Ser
                20                  25                  30

Ala Thr Tyr Lys Gly Gly Ile Thr Asp Tyr Ser Ser Ser Phe Gly Ile
            35                  40                  45

Ala Ile Glu Ala Val Ala Thr Ser Ala Ser Ser Val Ala Ser Ser Lys
        50                  55                  60

Ala Lys Arg Ala Ala Ser Gln Ile Gly Asp Gly Gln Val Gln Ala Ala
65                  70                  75                  80

Thr Thr Thr Ala Ala Val Ser Lys Lys Ser Thr Ala Ala Val Ser
                85                  90                  95

Gln Ile Thr Asp Gly Gln Val Gln Ala Ala Lys Ser Thr Ala Ala
                100                 105                 110

Val Ser Gln Ile Thr Asp Gly Gln Val Gln Ala Ala Lys Ser Thr Ala
            115                 120                 125

Ala Ala Val Ser Gln Ile Thr Asp Gly Gln Val Gln Ala Ala Lys Ser
        130                 135                 140

Thr Ala Ala Ala Val Ser Gln Ile Thr Asp Gly Gln Val Gln Ala Ala
145                 150                 155                 160

Lys Ser Thr Ala Ala Ala Ser Gln Ile Ser Asp Gly Gln Val Gln
                165                 170                 175

Ala Thr Thr Ser Thr Lys Ala Ala Ser Gln Ile Thr Asp Gly Gln
            180                 185                 190

Ile Gln Ala Ser Lys Thr Thr Ser Gly Ala Ser Gln Val Ser Asp Gly
        195                 200                 205

Gln Val Gln Ala Thr Ala Glu Val Lys Asp Ala Asn Asp Pro Val Asp
    210                 215                 220

Val Val Ser Cys Asn Asn Asn Ser Thr Leu Ser Met Ser Leu Ser Lys
225                 230                 235                 240

Gly Ile Leu Thr Asp Arg Lys Gly Arg Ile Gly Ser Ile Val Ala Asn
                245                 250                 255

Arg Gln Phe Gln Phe Asp Gly Pro Pro Gln Ala Gly Ala Ile Tyr
            260                 265                 270

Ala Ala Gly Trp Ser Ile Thr Pro Glu Gly Asn Leu Ala Leu Gly Asp
        275                 280                 285

Gln Asp Thr Phe Tyr Gln Cys Leu Ser Gly Asp Phe Tyr Asn Leu Tyr
    290                 295                 300

Asp Lys His Ile Gly Ser Gln Cys His Glu Val Tyr Leu Gln Ala Ile
```

```
                305                 310                 315                 320
Asp Leu Ile Asp Cys
            325

<210> SEQ ID NO 26
<211> LENGTH: 67
<212> TYPE: PRT
<213> ORGANISM: Artificial Sequence
<220> FEATURE:
<223> OTHER INFORMATION: Synthetic

<400> SEQUENCE: 26

Met Gln Tyr Lys Lys Pro Leu Val Val Ser Ala Leu Ala Ala Thr Ser
1               5                   10                  15

Leu Ala Ala Tyr Ala Pro Lys Asp Pro Trp Ser Thr Leu Thr Pro Ser
            20                  25                  30

Ala Thr Tyr Lys Gly Gly Ile Thr Asp Tyr Ser Ser Phe Gly Ile
        35                  40                  45

Ala Ile Glu Ala Val Ala Thr Ser Ala Ser Val Ala Ser Ser Lys
    50                  55                  60

Ala Lys Arg
65

<210> SEQ ID NO 27
<211> LENGTH: 258
<212> TYPE: PRT
<213> ORGANISM: Artificial Sequence
<220> FEATURE:
<223> OTHER INFORMATION: Synthetic

<400> SEQUENCE: 27

Ala Ala Ser Gln Ile Gly Asp Gly Gln Val Gln Ala Ala Thr Thr Thr
1               5                   10                  15

Ala Ala Val Ser Lys Lys Ser Thr Ala Ala Val Ser Gln Ile Thr
            20                  25                  30

Asp Gly Gln Val Gln Ala Ala Lys Ser Thr Ala Ala Ala Val Ser Gln
        35                  40                  45

Ile Thr Asp Gly Gln Val Gln Ala Ala Lys Ser Thr Ala Ala Ala Val
    50                  55                  60

Ser Gln Ile Thr Asp Gly Gln Val Gln Ala Ala Lys Ser Thr Ala Ala
65                  70                  75                  80

Ala Val Ser Gln Ile Thr Asp Gly Gln Val Gln Ala Ala Lys Ser Thr
                85                  90                  95

Ala Ala Ala Ser Gln Ile Ser Asp Gly Gln Val Gln Ala Thr Thr
            100                 105                 110

Ser Thr Lys Ala Ala Ala Ser Gln Ile Thr Asp Gly Gln Ile Gln Ala
        115                 120                 125

Ser Lys Thr Thr Ser Gly Ala Ser Gln Val Ser Asp Gly Gln Val Gln
    130                 135                 140

Ala Thr Ala Glu Val Lys Asp Ala Asn Asp Pro Val Asp Val Ser
145                 150                 155                 160

Cys Asn Asn Asn Ser Thr Leu Ser Met Ser Leu Ser Lys Gly Ile Leu
                165                 170                 175

Thr Asp Arg Lys Gly Arg Ile Gly Ser Ile Val Ala Asn Arg Gln Phe
            180                 185                 190

Gln Phe Asp Gly Pro Pro Gln Ala Gly Ala Ile Tyr Ala Ala Gly
        195                 200                 205
```

```
Trp Ser Ile Thr Pro Glu Gly Asn Leu Ala Leu Gly Asp Gln Asp Thr
    210                 215                 220

Phe Tyr Gln Cys Leu Ser Gly Asp Phe Tyr Asn Leu Tyr Asp Lys His
225                 230                 235                 240

Ile Gly Ser Gln Cys His Glu Val Tyr Leu Gln Ala Ile Asp Leu Ile
                245                 250                 255

Asp Cys

<210> SEQ ID NO 28
<211> LENGTH: 227
<212> TYPE: PRT
<213> ORGANISM: Saccharomyces cerevisiae

<400> SEQUENCE: 28

Met Gln Phe Lys Asn Val Ala Leu Ala Ala Ser Val Ala Ala Leu Ser
1               5                   10                  15

Ala Thr Ala Ser Ala Glu Gly Tyr Thr Pro Gly Glu Pro Trp Ser Thr
                20                  25                  30

Leu Thr Pro Thr Gly Ser Ile Ser Cys Gly Ala Ala Glu Tyr Thr Thr
            35                  40                  45

Thr Phe Gly Ile Ala Val Gln Ala Ile Thr Ser Ser Lys Ala Lys Arg
    50                  55                  60

Asp Val Ile Ser Gln Ile Gly Asp Gly Gln Val Gln Ala Thr Ser Ala
65                  70                  75                  80

Ala Thr Ala Gln Ala Thr Asp Ser Gln Ala Gln Ala Thr Thr Thr Ala
                85                  90                  95

Thr Pro Thr Ser Ser Glu Lys Ile Ser Ser Ala Ser Lys Thr Ser
            100                 105                 110

Thr Asn Ala Thr Ser Ser Ser Cys Ala Thr Pro Ser Leu Lys Asp Ser
    115                 120                 125

Ser Cys Lys Asn Ser Gly Thr Leu Glu Leu Thr Leu Lys Asp Gly Val
130                 135                 140

Leu Thr Asp Ala Lys Gly Arg Ile Gly Ser Ile Val Ala Asn Arg Gln
145                 150                 155                 160

Phe Gln Phe Asp Gly Pro Pro Gln Ala Gly Ala Ile Tyr Ala Ala
                165                 170                 175

Gly Trp Ser Ile Thr Glu Asp Gly Tyr Leu Ala Leu Gly Asp Ser Asp
            180                 185                 190

Val Phe Tyr Gln Cys Leu Ser Gly Asn Phe Tyr Asn Leu Tyr Asp Gln
    195                 200                 205

Asn Val Ala Glu Gln Cys Ser Ala Ile His Leu Glu Ala Val Ser Leu
    210                 215                 220

Val Asp Cys
225

<210> SEQ ID NO 29
<211> LENGTH: 64
<212> TYPE: PRT
<213> ORGANISM: Artificial Sequence
<220> FEATURE:
<223> OTHER INFORMATION: Synthetic

<400> SEQUENCE: 29

Met Gln Phe Lys Asn Val Ala Leu Ala Ala Ser Val Ala Ala Leu Ser
1               5                   10                  15

Ala Thr Ala Ser Ala Glu Gly Tyr Thr Pro Gly Glu Pro Trp Ser Thr
                20                  25                  30
```

```
Leu Thr Pro Thr Gly Ser Ile Ser Cys Gly Ala Ala Glu Tyr Thr Thr
            35                  40                  45

Thr Phe Gly Ile Ala Val Gln Ala Ile Thr Ser Ser Lys Ala Lys Arg
        50                  55                  60
```

<210> SEQ ID NO 30
<211> LENGTH: 163
<212> TYPE: PRT
<213> ORGANISM: Artificial Sequence
<220> FEATURE:
<223> OTHER INFORMATION: Synthetic

<400> SEQUENCE: 30

```
Asp Val Ile Ser Gln Ile Gly Asp Gly Gln Val Gln Ala Thr Ser Ala
1               5                   10                  15

Ala Thr Ala Gln Ala Thr Asp Ser Gln Ala Gln Ala Thr Thr Thr Ala
            20                  25                  30

Thr Pro Thr Ser Ser Glu Lys Ile Ser Ser Ala Ser Lys Thr Ser
            35                  40                  45

Thr Asn Ala Thr Ser Ser Ser Cys Ala Thr Pro Ser Leu Lys Asp Ser
        50                  55                  60

Ser Cys Lys Asn Ser Gly Thr Leu Glu Leu Thr Leu Lys Asp Gly Val
65                  70                  75                  80

Leu Thr Asp Ala Lys Gly Arg Ile Gly Ser Ile Val Ala Asn Arg Gln
                85                  90                  95

Phe Gln Phe Asp Gly Pro Pro Gln Ala Gly Ala Ile Tyr Ala Ala
            100                 105                 110

Gly Trp Ser Ile Thr Glu Asp Gly Tyr Leu Ala Leu Gly Asp Ser Asp
        115                 120                 125

Val Phe Tyr Gln Cys Leu Ser Gly Asn Phe Tyr Asn Leu Tyr Asp Gln
    130                 135                 140

Asn Val Ala Glu Gln Cys Ser Ala Ile His Leu Glu Ala Val Ser Leu
145                 150                 155                 160

Val Asp Cys
```

<210> SEQ ID NO 31
<211> LENGTH: 287
<212> TYPE: PRT
<213> ORGANISM: Saccharomyces cerevisiae

<400> SEQUENCE: 31

```
Met His Tyr Lys Lys Ala Phe Leu Ala Ser Leu Leu Ser Ser Ile Ala
1               5                   10                  15

Leu Thr Ala Tyr Ala Pro Pro Glu Pro Trp Ala Thr Leu Thr Pro Ser
            20                  25                  30

Ser Lys Met Asp Gly Gly Thr Thr Glu Tyr Arg Thr Ser Phe Gly Leu
        35                  40                  45

Ala Val Ile Pro Phe Thr Val Thr Glu Ser Lys Val Lys Arg Asn Val
    50                  55                  60

Ile Ser Gln Ile Asn Asp Gly Gln Val Gln Val Thr Thr Gln Lys Leu
65                  70                  75                  80

Pro His Pro Val Ser Gln Ile Gly Asp Gly Gln Ile Gln Val Thr Thr
                85                  90                  95

Gln Lys Val Pro Pro Val Val Ser His Ile Val Ser Gln Ile Gly Asp
            100                 105                 110

Gly Gln Leu Gln Ile Thr Thr Ala Lys Asn Val Val Thr Lys Ser Thr
```

```
                    115                 120                 125

Ile Ala Val Pro Ser Lys Thr Val Thr Ala Thr Ala Thr Ser Thr Ala
    130                 135                 140

Thr Ala Val Ser Gln Ile His Asp Gly Gln Val Gln Val Thr Ile Ser
145                 150                 155                 160

Ser Ala Ser Ser Ser Ser Val Leu Ser Lys Ser Lys Leu Glu Pro Thr
                165                 170                 175

Lys Lys Pro Asn Asn Glu Lys Val Ile Lys Val Gln Ala Cys Lys Ser
                180                 185                 190

Ser Gly Thr Leu Ala Ile Thr Leu Gln Gly Gly Val Leu Ile Asp Ser
            195                 200                 205

Ser Gly Arg Ile Gly Ser Ile Val Ala Asn Arg Gln Phe Gln Phe Asp
        210                 215                 220

Gly Pro Pro Gln Ala Gly Ala Ile Tyr Ala Gly Gly Trp Ser Ile
225                 230                 235                 240

Thr Lys His Gly Thr Leu Ala Ile Gly Asp Asn Asp Val Phe Tyr Gln
                245                 250                 255

Cys Leu Ser Gly Thr Phe Tyr Asn Leu Tyr Asp Gln Ser Ile Gly Gly
                260                 265                 270

Gln Cys Asn Pro Val His Leu Gln Thr Val Gly Leu Val Asp Cys
            275                 280                 285

<210> SEQ ID NO 32
<211> LENGTH: 62
<212> TYPE: PRT
<213> ORGANISM: Artificial Sequence
<220> FEATURE:
<223> OTHER INFORMATION: Synthetic

<400> SEQUENCE: 32

Met His Tyr Lys Lys Ala Phe Leu Ala Ser Leu Leu Ser Ser Ile Ala
1               5                   10                  15

Leu Thr Ala Tyr Ala Pro Pro Glu Pro Trp Ala Thr Leu Thr Pro Ser
            20                  25                  30

Ser Lys Met Asp Gly Gly Thr Thr Glu Tyr Arg Thr Ser Phe Gly Leu
        35                  40                  45

Ala Val Ile Pro Phe Thr Val Thr Glu Ser Lys Val Lys Arg
    50                  55                  60

<210> SEQ ID NO 33
<211> LENGTH: 225
<212> TYPE: PRT
<213> ORGANISM: Artificial Sequence
<220> FEATURE:
<223> OTHER INFORMATION: Synthetic

<400> SEQUENCE: 33

Asn Val Ile Ser Gln Ile Asn Asp Gly Gln Val Gln Val Thr Thr Gln
1               5                   10                  15

Lys Leu Pro His Pro Val Ser Gln Ile Gly Asp Gly Gln Ile Gln Val
            20                  25                  30

Thr Thr Gln Lys Val Pro Pro Val Ser His Ile Val Ser Gln Ile
        35                  40                  45

Gly Asp Gly Gln Leu Gln Ile Thr Thr Ala Lys Asn Val Val Thr Lys
    50                  55                  60

Ser Thr Ile Ala Val Pro Ser Lys Thr Val Thr Ala Thr Ala Thr Ser
65                  70                  75                  80
```

```
Thr Ala Thr Ala Val Ser Gln Ile His Asp Gly Gln Val Gln Val Thr
                85                  90                  95

Ile Ser Ser Ala Ser Ser Ser Val Leu Ser Lys Ser Lys Leu Glu
            100                 105                 110

Pro Thr Lys Lys Pro Asn Asn Glu Lys Val Ile Lys Val Gln Ala Cys
            115                 120                 125

Lys Ser Ser Gly Thr Leu Ala Ile Thr Leu Gln Gly Gly Val Leu Ile
130                 135                 140

Asp Ser Ser Gly Arg Ile Gly Ser Ile Val Ala Asn Arg Gln Phe Gln
145                 150                 155                 160

Phe Asp Gly Pro Pro Gln Ala Gly Ala Ile Tyr Ala Gly Trp
                165                 170                 175

Ser Ile Thr Lys His Gly Thr Leu Ala Ile Gly Asp Asn Asp Val Phe
                180                 185                 190

Tyr Gln Cys Leu Ser Gly Thr Phe Tyr Asn Leu Tyr Asp Gln Ser Ile
            195                 200                 205

Gly Gly Gln Cys Asn Pro Val His Leu Gln Thr Val Gly Leu Val Asp
    210                 215                 220

Cys
225

<210> SEQ ID NO 34
<211> LENGTH: 29
<212> TYPE: DNA
<213> ORGANISM: Artificial Sequence
<220> FEATURE:
<223> OTHER INFORMATION: Synthetic

<400> SEQUENCE: 34
gagaattcaa caacatgagt cgtagtagc                                    29

<210> SEQ ID NO 35
<211> LENGTH: 11
<212> TYPE: PRT
<213> ORGANISM: Artificial Sequence
<220> FEATURE:
<223> OTHER INFORMATION: Synthetic

<400> SEQUENCE: 35

Ser Gln Ile Gly Asp Gly Gln Val Gln Ala Thr
1               5                   10

<210> SEQ ID NO 36
<211> LENGTH: 27
<212> TYPE: DNA
<213> ORGANISM: Artificial Sequence
<220> FEATURE:
<223> OTHER INFORMATION: Synthetic

<400> SEQUENCE: 36
aaagaattca tggtgagcaa gggcgag                                      27

<210> SEQ ID NO 37
<211> LENGTH: 32
<212> TYPE: DNA
<213> ORGANISM: Artificial Sequence
<220> FEATURE:
<223> OTHER INFORMATION: Synthetic

<400> SEQUENCE: 37
aagcggccgc ttacttgtac agctcgtcca tg                                32
```

PICHIA PASTORIS PIR1 SECRETION SIGNAL PEPTIDE FOR RECOMBINANT PROTEIN EXPRESSION AND PICHIA PASTORIS PIR1 AND PIR2 ANCHOR DOMAIN PEPTIDES FOR RECOMBINANT SURFACE DISPLAY

CROSS-REFERENCE TO RELATED APPLICATIONS

This application claims the benefit of U.S. Provisional Patent Application No. 61/131,230, filed Jun. 6, 2008, and incorporated herein by reference in its entirety.

INCORPORATION OF SEQUENCE LISTING

A paper copy of the Sequence Listing and a computer readable form of the sequence listing provided herein, containing the file named "46589_81848_ST25.txt", which is 46154 KB in size (measured in MS-DOS), and are herein incorporated by reference. This Sequence Listing consists of SEQ ID NOs: 1-34.

BACKGROUND OF THE INVENTION

Rapid advances in recombinant DNA technology has led to the identification and isolation of many novel genes. Consequently, there is a need to express genes in a heterologous cell system to obtain material for structure-function studies, diagnostic reagents, testing, and therapy. Both eukaryotic and prokaryotic systems have been developed for the expression of heterologous genes. Perhaps the best known example of a prokaryotic expression system is *Escherichia coli*. Using prokaryotic systems to express eukaryotic genes, however, may create difficulties such as improper folding and improper post-translational modifications, which may affect a protein's function, activity, or stability. Moreover, the expressed product may be toxic to the prokaryotic cell or be produced in such large quantities that they interfere with cell growth. Thus, to overcome the drawbacks associated with expressing eukaryotic genes in prokaryotic cells, it may be necessary to express these genes in a eukaryotic cell. Expressing eukaryotic genes in eukaryotic cells provides for high levels of expression, proper post-translational modifications, and proper folding of the expression products. Eukaryotic expression systems may be, for example, mammalian, insect, and yeast cells.

Intrinsic difficulties limit intracellular expression. For example, intracellularly expression products must be purified from the host cell. Furthermore, expression products may sometimes be encapsulated be in inclusion bodies. Intracellular proteases may also degrade intracellularly expressed products. Some expressed products are produced in inactive forms possibly due to improper folding when produced intracellularly. The problems associated with intracellular expression may lead to decreased yield and make purification expensive and time consuming. Thus, it is desirable to use an expression system designed to transfer the heterologous protein from the intracellular environment.

Secretion of the heterologous protein provides an alternative to intracellular expression. Sambrook et al. Molecular Cloning 17.31 (1989) provide examples of expression vectors designed for the secretion of heterologous proteins in *E. coli*. Generally, secretion of the expressed product is accomplished by operably linking a nucleotide sequence encoding a secretion signal peptide to a nucleotide sequence encoding the heterologous polypeptide. The secretion signal peptide directs the expressed product through the secretory pathway and into the extracellular medium. Secretion of expression products may allow for proper folding and post-translational modification of the expressed product. Secretion of expression products is also advantageous in that purification of the protein of interest does not require harsh treatment to obtain the protein from within the cell. Thus expression systems providing for secretion of the expressed product into the extracellular medium may avoid problems associated with intracellular expression.

Expression of the heterologous protein on the surface of the host cell is also desirable in certain applications. Surface display is accomplished by operably linking a nucleic acid sequence encoding an anchor domain peptide to a nucleotide sequence encoding a heterologous polypeptide that is subsequently shuttled through the secretory pathway and "displayed" on the cell. The anchor domain peptide may be covalently or noncovalently attached to the cell wall. Surface display of heterologous proteins on the host cell allows for post-translational processing, efficient folding, and activity. Surface display is useful for obtaining specific antibodies, determining enzyme specificity, studying protein-protein interactions, fluorescence-activated cell sorting (FACS), and expression cloning. Both prokaryotic and eukaryotic systems are available for expression on the cell. Using prokaryotic systems for surface display of eukaryotic genes, however, shares similar drawbacks to prokaryotic systems for intracellular and secretion expression of eukaryotic genes. For example, prokaryotic cells do not efficiently express functional eukaryotic proteins and lack the ability to introduce post-translational modifications.

Yeast host cell expression systems are useful for recombinant protein expression. As eukaryotes, yeast provide the advantages of proper folding, post-translational modification, and function, such that heterologous proteins are very similar to native proteins from other eukaryotic sources (e.g., mammals, avians, and plants).

*S. cerevisiae* was the first, and remains one of the most commonly employed yeast expression systems because its genome and physiology have been extensively characterized. *P. pastoris* is a methylotrophic yeast that has also been developed for heterologous protein expression. Heterologous protein expression using *P. pastoris* is advantageous relative to *S. cerevisiae* because it may be cultured at high densities (150 g/L dry cell weight; 500 OD 600 U/mL) where *S. cerevisiae* produces ethanol at toxic levels. *P. pastoris* also provides an advantageous heterologous protein production system for production of human pharmaceuticals because it is inexpensive and the cells readily grow in defined medium that is free of undefined ingredients that may be sources of toxins. Additionally, *P. pastoris* may be cultured in medium with a relatively low pH and methanol, and thus are less likely to become contaminated by other microorganisms.

Because the yeast secrete only a small amount of native protein into its growth medium, yeast expression systems provide a useful alternative to other expression systems. Constructions for secretion of the protein of interest may use the native secretion signal sequence of the protein of interest. In some cases, however, *P. pastoris* has not been able to efficiently utilize the native signal sequence of the protein of interest to direct secretion. See e.g., Tschopp et al. (5 Bio/Technology 1305-1308 (1987)). Researchers have successfully used the native secretion signal sequence of the heterologous protein, the *S. cerevisiae* α-factor pre-pro peptide, and the *P. pastoris* acid phosphatase (PHO1) signal for secretion of expressed heterologous proteins. However, results have been variable. See e.g., Ilgen et al. (Production of Recombinant Proteins: Novel Microbial and Eukaryotic Expression Systems 152-153 (Gerd Gellissen, ed., WILEY- VCH Verlag GmbH & Co. KGaA)); Vedvic et al. (5 J. Ind. Microbiol. 197-201 (1991)); Clare et al. (105 Gene 205-212 (1991)).

Researchers have also successfully developed yeast expression systems for displaying heterologous peptides on the cell surface. Boder and Wittrup, (15 Nature Biotechnol. 533-557 (1997)) disclose a yeast expression system using *S. cerevisiae*. This method uses a *S. cerevisiae*-derived α-agglutinin adhesion receptor, which consists of the Aga1 and Aga2 subunits. Aga1 is anchored to the cell wall via a β-glucan covalent linkage and Aga2 is linked to Aga1 by disulfide bonds. Yeast express a heterologous polypeptide linked to Aga2, which is displayed on the cell surface. Wang et al. (56 Curr. Microbiol. 352-357 (2008); PIR1), Mergler et al. (63 Appl. Microbiol. Biotechnol. 418-421 (2004); GPI), and Tamino et al. (22 Biotechnol. Prog. 989-993 (2006); Flo1p) each disclose using a *S. cerevisiae*-derived anchor domain protein for surface display in *P. pastoris* cells.

With all the purported advantages, heterologous protein expression in yeast is far from optimal. Accordingly, a need still exists for yeast expression systems providing for expression of heterologous proteins wherein the heterologous protein is transferred from the intracellular environment of the host cell to either the growth media or the cell surface.

SUMMARY OF THE INVENTION

The invention generally provides recombinant nucleic acid constructs, isolated nucleic acids, transformed cells, and kits comprising *Pichia pastoris* PIR protein sequences that are useful for expression of heterologous genes in yeast cells. The invention also provides methods for expression of heterologous polypeptides as secreted proteins and methods for expressing heterologous polypeptides on the cell surface using *Pichia pastoris* PIR protein sequences.

In certain embodiments, the invention provides a recombinant nucleic acid construct comprising a nucleic acid sequence encoding a secretion signal peptide, wherein the secretion signal peptide has at least about 70% sequence identity to the amino acid sequence of SEQ ID NO: 15 and wherein the nucleic acid sequence encoding the secretion signal peptide is operably linked to both a heterologous expression control sequence and a heterologous nucleic acid sequence comprising a site for operable insertion of a nucleic acid sequence encoding a polypeptide. The site for operable insertion of a heterologous nucleic acid sequence encoding a polypeptide may further comprises at least one restriction endonuclease recognition sequence. The recombinant nucleic acid construct may be DNA or RNA. The recombinant nucleic acid construct may further comprise a nucleic acid sequence encoding a heterologous polypeptide inserted into the site for operable insertion, wherein the nucleic acid sequence encoding a heterologous polypeptide is operably linked to the nucleic acid encoding the secretion signal peptide. In other aspects, the secretion signal peptide sequence can have at least about 80%, about 90%, about 95%, about 98%, or about 99% sequence identity to the amino acid sequence of SEQ ID NO: 15. The nucleic acid sequence encoding a secretion signal peptide can comprise the nucleic acid sequence of SEQ ID NO: 14. The heterologous expression control sequence is a promoter, wherein the promoter may be an Alcohol Oxidase I promoter, an Alcohol Oxidase II promoter, a GAP promoter, a FLD1 promoter, a YTP1 promoter, and a PEX8 promoter. The recombinant nucleic acid may further comprise a polyadenylation sequence and wherein the promoter, the nucleic acid sequence encoding the secretion signal peptide, the site for operable insertion of a nucleic acid sequence encoding a polypeptide, the nucleic acid sequence encoding a heterologous polypeptide, and the polyadenylation sequence are operably linked.

In certain embodiments, the invention provides an isolated nucleic acid comprising a nucleotide sequence encoding a secretion signal peptide that has at least 70% identity to SEQ ID NO: 14. In other aspects, the sequence that encodes a secretion signal peptide has at least about 80%, about 90%, about 95%, about 98%, or about 99% sequence identity to the nucleotide sequence of SEQ ID NO: 14. The nucleic acid sequence encoding the secretion signal peptide is operably linked to a nucleic acid sequence encoding a heterologous polypeptide.

In certain embodiments, the invention provides a transformed cell comprising a nucleotide sequence encoding a secretion signal peptide that has at least 70% identity to SEQ ID NO: 14 that is operably linked to a nucleic acid sequence encoding a heterologous polypeptide. The transformed cell may be a yeast cell or a bacterial cell. The yeast cell may be a *Pichia* cell, a *Saccharomyces* cell, a *Kluyveromyces* cell, a *Candida* cell, a *Torulopsis* cell, a *Hansenula* cell, or a *Yarrowia* cell.

In certain embodiments, the invention provides a transformed cell comprising a nucleotide sequence encoding a secretion signal peptide that has at least about 70% identity to the amino acid sequence of SEQ ID NO: 15 that is operably linked to a nucleic acid sequence encoding a heterologous polypeptide. In certain aspects, the nucleotide sequence encodes a secretion signal peptide that has at least about 80%, about 90%, about 95%, about 98%, or about 99% sequence identity to the amino acid sequence of SEQ ID NO: 15. The transformed cell may be a yeast cell or a bacterial cell. The yeast cell may be a *Pichia* cell, a *Saccharomyces* cell, a *Kluyveromyces* cell, a *Candida* cell, a *Torulopsis* cell, a *Hansenula* cell, or a *Yarrowia* cell.

In certain embodiments, the invention provides a method for obtaining a heterologous polypeptide comprising culturing a cell transformed with a recombinant nucleic acid construct, the recombinant nucleic acid construct comprising a heterologous expression control sequence, a sequence encoding a secretion signal peptide that has at least about 70% sequence identity to the amino acid sequence of SEQ ID NO: 15, and a sequence encoding a heterologous polypeptide, wherein the heterologous expression control sequence, the sequence encoding a secretion signal peptide, and the sequence encoding a heterologous polypeptide are operably linked and wherein the cell is cultured under conditions permitting expression of the heterologous polypeptide and recovering the heterologous polypeptide from the cell or a culture medium, thereby obtaining the heterologous polypeptide. In other aspects, the sequence encodes a secretion signal peptide that has at least about 80%, about 90%, about 95%, about 98%, or about 99% sequence identity to the amino acid sequence of SEQ ID NO: 15.

In certain embodiments, the invention provides a kit comprising a recombinant nucleic acid construct and instructions for the use thereof, wherein the recombinant nucleic acid construct comprises a nucleic acid sequence encoding a secretion signal peptide that has at least about 70% sequence identity to the amino acid sequence of SEQ ID NO: 15 and wherein the nucleic acid sequence encoding the secretion signal peptide is operably linked to both a heterologous expression control sequence and a heterologous nucleic acid sequence comprising a site for operable insertion of a nucleic acid sequence encoding a polypeptide. In other aspects, the nucleic acid sequence encodes a secretion signal peptide that has at least about 80%, about 90%, about 95%, about 98%, or about 99% sequence identity to the amino acid sequence of SEQ ID NO: 15.

In certain embodiments, the invention provides a recombinant nucleic acid construct comprising a nucleic acid sequence encoding an anchor domain peptide, wherein the anchor domain peptide has at least about 70% sequence identity to the amino acid sequence of SEQ ID NO: 2 and wherein the nucleic acid sequence encoding the anchor domain peptide is operably linked to both a heterologous expression control sequence and a heterologous nucleic acid sequence comprising a site for operable insertion of a nucleic acid sequence encoding a polypeptide. The site for operable insertion of a heterologous nucleic acid sequence encoding a polypeptide may further comprise at least one restriction endonuclease recognition sequence. The recombinant nucleic acid construct may be DNA or RNA. The recombinant nucleic acid construct may further comprise a nucleic acid sequence encoding a heterologous polypeptide inserted into the site for operable insertion, wherein the nucleic acid sequence encoding a heterologous polypeptide is operably linked to the nucleic acid encoding the anchor domain peptide. In certain aspects, the anchor domain peptide sequence has at least about 80%, about 90%, about 95%, about 98% or about 99% sequence identity to the amino acid sequence of SEQ ID NO: 2. In certain aspects, the nucleic acid sequence encoding an anchor domain peptide comprises the nucleic acid sequence of SEQ ID NO: 1. The heterologous expression control sequence is a promoter, wherein the promoter may be an Alcohol Oxidase I promoter, an Alcohol Oxidase II promoter, a GAP promoter, a FLD1 promoter, a YTP1 promoter, and a PEX8 promoter. The recombinant nucleic acid may further comprise a polyadenylation sequence and wherein the promoter, the nucleic acid sequence encoding the secretion signal peptide, the site for operable insertion of a nucleic acid sequence encoding a polypeptide, the nucleic acid sequence encoding a heterologous polypeptide, and the polyadenylation sequence are operably linked.

In certain embodiments, the invention provides a isolated nucleic acid comprising a nucleotide sequence encoding an anchor domain peptide that has at least 70% identity to SEQ ID NO: 1. The nucleic acid sequence encoding the anchor domain peptide may be operably linked to a nucleic acid sequence encoding a heterologous polypeptide.

In certain embodiments, the invention provides a transformed cell comprising a nucleotide sequence encoding an anchor domain peptide that has at least 70% identity to SEQ ID NO: 1 that is operably linked to a nucleic acid sequence encoding a heterologous polypeptide. The transformed cell may be a yeast cell or a bacterial cell. The yeast cell may be a *Pichia* cell, a *Saccharomyces* cell, a *Kluyveromyces* cell, a *Candida* cell, a *Torulopsis* cell, a *Hansenula* cell, or a *Yarrowia* cell.

In certain embodiments, the invention provides a transformed cell comprising a nucleotide sequence encoding an anchor domain peptide that has at least 70% identity to the amino acid sequence of SEQ ID NO: 2 that is operably linked to a nucleic acid sequence encoding a heterologous polypeptide. In certain aspects, the nucleotide sequence encodes an anchor domain peptide that has at least about 80%, about 90%, about 95%, about 98% or about 99% sequence identity to the amino acid sequence of SEQ ID NO: 2. The transformed cell may be a yeast cell or a bacterial cell. The yeast cell may be a *Pichia* cell, a *Saccharomyces* cell, a *Kluyveromyces* cell, a *Candida* cell, a *Torulopsis* cell, a *Hansenula* cell, or a *Yarrowia* cell.

In certain embodiments, the invention provides a method for expressing a heterologous polypeptide on a host cell comprising culturing a cell transformed with a recombinant nucleic acid construct, the recombinant nucleic acid construct comprising a heterologous expression control sequence, a sequence encoding an anchor domain peptide that has at least about 70% sequence identity to the amino acid sequence of SEQ ID NO: 2, and a sequence encoding a heterologous polypeptide, wherein the heterologous expression control sequence, the sequence encoding an anchor domain peptide, and the sequence encoding a heterologous polypeptide are operably linked, and wherein the cell is cultured under conditions permitting expression of the heterologous polypeptide, thereby expressing the heterologous polypeptide on the host cell. In certain aspects, the sequence encodes an anchor domain peptide that has at least about 80%, about 90%, about 95%, about 98% or about 99% sequence identity to the amino acid sequence of SEQ ID NO: 2. The method may further comprise recovering the host cell expressing the heterologous polypeptide. The method may further comprise recovering the heterologous polypeptide from the host cell thereby obtaining the heterologous polypeptide.

In certain embodiments, the invention provides a kit comprising a recombinant nucleic acid construct and instructions for the use thereof, wherein the recombinant nucleic acid construct comprises a nucleic acid sequence encoding an anchor domain peptide that has at least about 70% sequence identity to the amino acid sequence of SEQ ID NO: 2 and wherein said nucleic acid sequence encoding said anchor domain peptide is operably linked to both a heterologous expression control sequence and a heterologous nucleic acid sequence comprising a site for operable insertion of a nucleic acid sequence encoding a polypeptide.

In certain embodiments, the invention provides a recombinant nucleic acid construct comprising a nucleic acid sequence encoding an anchor domain peptide, wherein the anchor domain peptide has at least about 70% sequence identity to the amino acid sequence of SEQ ID NO: 4 and wherein the nucleic acid sequence encoding the anchor domain peptide is operably linked to both a heterologous expression control sequence and a heterologous nucleic acid sequence comprising a site for operable insertion of a nucleic acid sequence encoding a polypeptide. The nucleic acid sequence comprising a site for operable insertion of a heterologous nucleic acid sequence encoding a polypeptide further comprises at least one restriction endonuclease recognition sequence. The recombinant nucleic acid construct is DNA or RNA. The recombinant nucleic acid construct further comprises a nucleic acid sequence encoding a heterologous polypeptide inserted into the site for operable insertion, wherein the nucleic acid sequence encoding a heterologous polypeptide is operably linked to the nucleic acid encoding said secretion signal peptide. In certain aspects, the nucleic sequence encodes an anchor domain peptide that has at least about 80%, about 90%, about 95%, about 98%, or about 99% sequence identity to the amino acid sequence of SEQ ID NO: 4. The nucleic acid sequence encoding the anchor domain peptide comprises the nucleic acid sequence of SEQ ID NO: 3. The heterologous expression control sequence is a promoter, wherein the promoter is an Alcohol Oxidase I promoter, an Alcohol Oxidase II promoter, a GAP promoter, a FLD1 promoter, a YTP1 promoter, and a PEX8 promoter. The recombinant nucleic acid further comprises a polyadenylation sequence and wherein the promoter, the nucleic acid sequence encoding the anchor domain peptide, the site for operable insertion of a nucleic acid sequence encoding a polypeptide, the nucleic acid sequence encoding a heterologous polypeptide, and the polyadenylation sequence are operably linked.

In certain embodiments, the invention provides an isolated nucleic acid comprising a nucleotide sequence encoding an anchor domain peptide that has at least 70% identity to SEQ ID NO: 3. The nucleic acid sequence encoding the anchor domain peptide may be operably linked to a nucleic acid sequence encoding a heterologous polypeptide.

In certain embodiments, the invention provides a transformed cell comprising a nucleotide sequence encoding an anchor domain peptide that has at least 70% identity to SEQ ID NO: 4 that is operably linked to a nucleic acid sequence encoding a heterologous polypeptide. In certain aspects, the nucleotide sequence encodes an anchor domain peptide that has at least about 80%, about 90%, about 95%, about 98% or about 99% sequence identity to the amino acid sequence of SEQ ID NO: 4. The transformed cell may be a yeast cell or a bacterial cell. The yeast cell is a *Pichia* cell, a *Saccharomyces* cell, a *Kluyveromyces* cell, a *Candida* cell, a *Torulopsis* cell, a *Hansenula* cell, or a *Yarrowia* cell.

In certain embodiments, the invention provides a method for expressing a heterologous polypeptide on a host cell comprising culturing a cell transformed with a recombinant nucleic acid construct, the recombinant nucleic acid construct comprising a heterologous expression control sequence, a sequence encoding an anchor domain peptide that has at least about 70% sequence identity to the amino acid sequence of SEQ ID NO: 4, and a sequence encoding a heterologous polypeptide, wherein the heterologous expression control sequence, the sequence encoding an anchor domain peptide, and the sequence encoding a heterologous polypeptide are operably linked, and wherein the cell is cultured under conditions permitting expression of the heterologous polypeptide, thereby expressing the heterologous polypeptide on the host cell. The method may further comprise recovering the host cell expressing the heterologous polypeptide. The method may further comprise recovering the heterologous polypeptide from the host cell thereby obtaining the heterologous polypeptide. In certain aspects, the sequence encodes an anchor domain peptide that has at least about 80%, about 90%, about 95%, about 98%, or about 99% sequence identity to the amino acid sequence of SEQ ID NO: 4.

In certain embodiments, the invention provides a kit comprising a recombinant nucleic acid construct and instructions for the use thereof, wherein the recombinant nucleic acid construct comprises a nucleic acid sequence encoding an anchor domain peptide that has at least about 70% sequence identity to the amino acid sequence of SEQ ID NO: 4 and wherein the nucleic acid sequence encoding the anchor domain peptide is operably linked to both a heterologous expression control sequence and a heterologous nucleic acid sequence comprising a site for operable insertion of a nucleic acid sequence encoding a polypeptide. In certain aspects, the nucleic acid sequence encodes an anchor domain peptide that has at least about 80%, about 90%, about 95%, about 98%, or about 99% sequence identity to the amino acid sequence of SEQ ID NO: 4.

BRIEF DESCRIPTION OF THE DRAWINGS

FIGS. 1A, 1B, and 1C is an alignment of the full-length amino acid sequences for PIR proteins from *Pichia pastoris* and *Saccharomyces cerevisiae*.

FIG. 2 is an amino acid sequence alignment of the PIR protein secretion signal peptides from *P. pastoris* and *S. cerevisiae*.

FIGS. 3A, 3B, and 3C is an amino acid sequence alignment of the PIR protein anchor domain peptides from *P. pastoris* and *S. cerevisiae*.

FIG. 4 is an illustration of the pPICZ/PIR1L/EGFP vector map containing the AOX1 promoter, the PpPIR1 secretion signal sequence, and EGFP gene.

FIG. 5 is an illustration of the pGAPZ/PIR1L/EGFP vector map containing the GAPZ promoter, the PpPIR1 secretion signal sequence, and EGFP gene.

FIG. 6 is an illustration of the pPICZ/PIR1/EGFP vector map containing the AOX1 promoter, the full-length PpPIR1 sequence, and the EGFP gene.

FIG. 7 is an illustration of the pPICZ/PIR1/EGFP vector map containing the GAPZ promoter, the full-length PpPIR1 sequence, and the EGFP gene.

FIG. 8 is an illustration of the pPICZ/PIR2/EGFP vector map containing the AOX1 promoter, the full-length PpPIR2 sequence, and the EGFP gene.

FIG. 9 is an illustration of the pGAPZ/PIR2/EGFP vector map containing the GAPZ promoter, the full-length PpPIR2 sequence, and the EGFP gene.

FIG. 10 is an SDS-PAGE analysis of EGFP expression in *P. pastoris*.

FIG. 11 is a Western blot analysis of EGFP expression in yeast transformed with the GAP-PpPIR1 secretion signal sequence-EGFP construct, the AOX1-PpPIR1 secretion signal sequence-EGFP construct and the AOX1-PpPIR2 secretion signal sequence-EGFP construct.

FIG. 12 is a confocal microscope image showing EGFP on the cell surface of yeast transformed with the AOX1-full-length PpPIR1 sequence-EGFP construct.

FIG. 13 is a confocal microscope image showing EGFP on the cell surface of yeast transformed with the AOX1-full-length PpPIR1 sequence-EGFP construct.

FIG. 14 is a confocal microscope image showing EGFP on the cell surface of yeast transformed with the AOX1-full-length PpPIR2 sequence-EGFP construct.

FIG. 15 is a confocal microscope image showing EGFP on the cell surface of yeast transformed with the GAP-full-length PpPIR1 sequence-EGFP construct.

FIG. 16 is a confocal microscope image showing EGFP on the cell surface of yeast transformed with the GAP-full-length PpPIR2 sequence-EGFP construct.

FIG. 17 is an illustration of the pPICZ/PIR2L/EGFP vector map containing the AOX1 promoter, the putative PpPIR2 secretion signal sequence, and EGFP gene.

FIG. 18 is an illustration of the pGAPZ/PIR2L/EGFP vector map containing the GAP promoter, the putative PpPIR2 secretion signal sequence, and EGFP gene.

DETAILED DESCRIPTION

Definitions

As used herein, "heterologous" means not naturally contiguous. For example, a yeast secretion signal peptide sequence and a human polypeptide sequence are heterologous because the two sequences are not naturally contiguous.

The terms "polypeptide," "peptide" and "protein" are used interchangeably herein to refer to a polymer of amino acid residues of any length.

The term "construct", as used herein, refers to any recombinant polynucleotide molecule. Examples of constructs may be a plasmid, a cosmid, a virus, an autonomously replicating polynucleotide molecule, a phage, or a linear or circular single-stranded or double-stranded DNA or RNA polynucleotide molecule, derived from any source, capable of genomic integration or autonomous replication, comprising a polynucleotide molecule where one or more polynucleotide molecule(s) has been linked in a functionally operative manner, i.e., operably linked.

The phrase "DNA construct", as used herein refers to any DNA molecule in which two or more ordinarily distinct DNA sequences have been covalently linked. Examples of DNA constructs may be, for example, plasmids, cosmids, viruses, BACs (bacterial artificial chromosome), YACs (yeast artificial chromosome), plant minichromosomes, autonomously replicating sequences, phage, or linear or circular single-stranded or double-stranded DNA sequences, derived from any source, that are capable of genomic integration or autonomous replication. DNA constructs may be assembled by a variety of methods such as, for example, recombinant DNA techniques, DNA synthesis techniques, PCR (Polymerase Chain Reaction) techniques, or any combination of techniques.

The phrase "heterologous promoter", as used herein, refers to a promoter that is not operably linked to the structural gene in nature or a promoter derived from the same source as the operably linked structural gene where the promoter's sequence is modified from its original form. For example, an AOX1 promoter derived from *Pichia* is considered a "heterologous promoter" when it is operably linked to a sequence encoding a polypeptide. Additionally, the promoter may be derived from a different organism than the host cell. For example, an GAP promoter derived from *Saccharomyces* may be used in a construct that is expressed in a *Pichia* host cell.

The phrase "operably linked", as used herein, refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter and is linked such that the resulting translation product is in frame with the translational open reading frame that encodes the desired protein. Nucleic acid sequences that can be operably linked may be, for example, sequences that provide gene expression functions (i.e., gene expression elements such as promoters, 5' untranslated regions, introns, protein coding regions, 3' untranslated regions, polyadenylation sites, and/or transcriptional terminators), sequences that provide DNA transfer and/or integration functions, sequences that provide for selective functions (i.e., antibiotic resistance markers, biosynthetic genes), sequences that provide scoreable marker functions (i.e., reporter genes), sequences that facilitate in vitro or in vivo manipulations of the sequences (i.e., polylinker sequences, site specific recombination sequences) and sequences that provide replication functions (i.e., bacterial origins of replication, autonomous replication sequences, centromeric sequences).

"Operable insertion" as used herein refers to the insertion of a sequence into a recombinant nucleic acid construct so that it is operably linked to at least one other sequence in such construct.

The term "expression control sequence", as used herein, refers to nucleic acid sequences that regulate the expression of a nucleic acid sequence to which it is operatively linked. Expression control sequences are sequences that control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); and sequences that enhance protein stability.

The term "transformation", as used herein, refers to a process of introducing a nucleic acid sequence into a cell or organism. "Stable transformation" refers to a transformed nucleic acid that is incorporated into a chromosome or is capable of autonomous replication.

The term "vector", as used herein, refers to any recombinant polynucleotide construct that may be used to introduce heterologous DNA into a host cell.

The phrases "surface display" and/or "cell surface display", as used herein, refer to both covalent and noncovalent linkage of a polypeptide to the extracellular surface of the cell wall.

*P. pastoris* PIR1 and PIR2 Genes

It has been determined herein that *P. pastoris* has PIR1 ("PpPIR1") and PIR2 ("PpPIR2") proteins that are distantly related to the PIR proteins of *S. cerevisiae* (ScPIR1, ScPIR2, ScPIR3, ScPIR4, and ScPIR5). FIG. 1 is an amino acid sequence alignment of the PpPIR1 (SEQ ID NO: 2) and PpPIR2 (SEQ ID NO: 4) amino acid sequences with the amino acid sequences of *S. cerevisiae* PIR1 (SEQ ID NO: 19), PIR2 (SEQ ID NO: 22), PIR3 (SEQ ID NO: 25), PIR4 (SEQ ID NO: 28), and PIR5 (SEQ ID NO: 31). Table 1 shows sequence homology values between the full-length amino acid sequences of *P. pastoris* PIR1 and PIR2 and *S. cerevisiae* PIR1-PIR5.

TABLE 1

Sequence Homology Values Among PIR Proteins (whole sequences)*

|        | PpPIR1 | PpPIR2 | ScPIR4 | ScPIR5 | ScPIR1 | ScPIR2 | ScPIR3 |
|--------|--------|--------|--------|--------|--------|--------|--------|
| PpPIR1 |        | 45     | 50     | 48     | 61     | 63     | 57     |
| PpPIR2 |        |        | 51     | 42     | 48     | 45     | 42     |
| ScPIR4 |        |        |        | 53     | 56     | 60     | 54     |

TABLE 1-continued

Sequence Homology Values Among PIR Proteins (whole sequences)*

| | PpPIR1 | PpPIR2 | ScPIR4 | ScPIR5 | ScPIR1 | ScPIR2 | ScPIR3 |
|---|---|---|---|---|---|---|---|
| ScPIR5 | | | | | 57 | 57 | 50 |
| ScPIR1 | | | | | | 83 | 75 |
| ScPIR2 | | | | | | | 73 |
| ScPIR3 | | | | | | | |

*Values are the percentage of identical residues among all ungapped positions between the pairs using AlignX (Clustal W-based) using blosum62mt2 matrix with gap-opening penalty of 10 and gap-extension penalty of 0.1.

The PpPIR1 and PpPIR2 amino acid sequences are 45% identical to each other. The PpPIR1 protein is 61% identical to PIR1 of *S. cerevisiae*. The PpPIR2 protein is 45% identical to PIR2 of *S. cerevisiae*. The PpPIR1 gene encodes secretion signal located near the N-terminus of the protein. FIG. 2 is an amino acid sequence alignment of the secretion signal peptides of PpPIR1 (SEQ ID NO: 15) with *S. cerevisiae* PIR1 (SEQ ID NO: 20), PIR2 (SEQ ID NO: 23), PIR3 (SEQ ID NO: 26), PIR4 (SEQ ID NO: 29) and PIR5 (SEQ ID NO: 32). The PpPIR1 secretion signal sequence is 39%, 41%, 39%, and 37% identical to the secretion signal sequence of *S. cerevisiae* PIR4, PIR2, PIR1, and PIR3, respectively. See, Table 2. Also included in the alignment is the putative PpPIR2 secretion signal peptide (SEQ ID NO: 17). The PpPIR2 secretion signal sequence lacks the KEX2 cleavage site (i.e., KR) that is present in PpPIR1 and *S. cerevisiae* PIR1, PIR2, PIR3, PIR4, and PIR5. See, FIG. 2. The putative PpPIR2 secretion signal peptide is 30% identical to PpPIR1 secretion signal and 40%, 36%, 38%, 30%, and 33% identical to *S. cerevisiae* PIR1, PIR3, PIR2, PIR5, and PIR4, respectively.

(SEQ ID NO: 33). The PpPIR1 anchor domain peptide sequence contains 6 of the repetitive sequence motifs shared by PIR proteins. The PpPIR1 sequence contains 2 additional sequences related to the repetitive sequences. The PpPIR1 related sequence at amino acid positions 63-73 has one of the conserved amino acids exchanged. The PpPIR1 related sequence at amino acid positions 231-241 has three of the conserved amino acids exchanged. The PpPIR2 anchor domain peptide sequence contains one repetitive sequence motif shared by PIR proteins. The PpPIR2 sequence contains 3 additional sequences related to the repetitive sequences. The PpPIR2 related sequence at amino acid position 70-80 has two of the conserved amino acids exchanged. The PpPIR2 related sequence at amino acid position 115-125 has one of the conserved amino acids exchanged. The PpPIR2 related sequence at amino acid position 136-146 has two of the conserved amino acids exchanged. Although the PpPIR1 and PpPIR2 repetitive sequence domains and related sequences are about 81% to 100% identical to the consensus sequence of

TABLE 2

Sequence Homology Values Among PIR Secretion Signal Sequences*

| | PpPIR1SS | PpPIR2SS | ScPIR1SS | ScPIR3SS | ScPIR2SS | ScPIR5SS | ScPIR4SS |
|---|---|---|---|---|---|---|---|
| PpPIR1SS | | 30 | 39 | 37 | 41 | 32 | 39 |
| PpPIR2SS | | | 40 | 36 | 38 | 30 | 33 |
| ScPIR1SS | | | | 82 | 73 | 48 | 42 |
| ScPIR3SS | | | | | 61 | 45 | 40 |
| ScPIR2SS | | | | | | 48 | 48 |
| ScPIR5SS | | | | | | | 42 |
| ScPIR4SS | | | | | | | |

*Values are the percentage of identical residues among all ungapped positions between the pairs using AlignX (Clustal W-based) using blosum62mt2 matrix with gap-opening penalty of 10 and gap-extension penalty of 0.1.

The PpPIR1 and PpPIR2 genes also encode anchor domain peptides having the repetitive sequence motif (i.e., SQIGDGQVQAT (SEQ ID NO: 35)) shared among the PIR proteins. Without being held to a particular theory, it is believed that the repetitive sequence motif functions to attach the protein to the cell wall. See, Ecker et al. (281 J. Biol. Chem. 11523-11529 (April 2006)). FIG. 3 is an amino acid sequence alignment of the anchor domain peptides of PpPIR1 (SEQ ID NO: 16) and PpPIR2 (SEQ ID NO: 18) with *S. cerevisiae* PIR1 (SEQ ID NO: 21), PIR2 (SEQ ID NO: 24), PIR3 (SEQ ID NO: 27), PIR4 (SEQ ID NO: 30), and PIR5 the repetitive sequence motif, the PpPIR1 and PpPIR2 anchor domains are only 50% identical to each other over the entire anchor domain sequence that extends from about residue 60 to residue 355 of PpPIR1 and from about residue 67 to residue 323 of PpPIR2. Moreover, the PpPIR1 anchor domain is 54%, 52%, 60%, 64%, and 66% identical over the entire anchor domain sequence of *S. cerevisiae* PIR4, PIR5, PIR3, PIR1, and PIR2. See, Table 3. The PpPIR2 anchor domain is 57%, 44%, 46%, 51%, and 49% identical over the entire anchor domain sequence of *S. cerevisiae* PIR4, PIR5, PIR3, PIR1, and PIR2. See, Table 3.

TABLE 3

Sequence Homology Values Among PIR Anchor Domains*

|        | PpPIR1 | PpPIR2 | ScPIR4 | ScPIR5 | ScPIR3 | ScPIR1 | ScPIR2 |
|--------|--------|--------|--------|--------|--------|--------|--------|
| PpPIR1 |        | 50     | 54     | 52     | 60     | 64     | 66     |
| PpPIR2 |        |        | 57     | 44     | 46     | 51     | 49     |
| ScPIR4 |        |        |        | 56     | 57     | 59     | 62     |
| ScPIR5 |        |        |        |        | 51     | 57     | 58     |
| ScPIR3 |        |        |        |        |        | 72     | 73     |
| ScPIR1 |        |        |        |        |        |        | 83     |
| ScPIR2 |        |        |        |        |        |        |        |

*Values are the percentage of identical residues among all ungapped positions between the pairs using AlignX (Clustal W-based) using blosum62mt2 matrix with gap-opening penalty of 10 and gap-extension penalty of 0.1.

Operably linking the sequence encoding the PpPIR1 secretion signal peptide to a sequence encoding a heterologous polypeptide as provided by the instant invention results in secretion of the expressed polypeptide from a transformed host cell into the culture medium. Operably linking the full-length PpPIR1 containing the secretion signal peptide and anchor domain peptide sequences to a sequence encoding a heterologous polypeptide as provided by the instant invention results in display of the expressed polypeptide on the surface of a transformed host cell. Operably linking the full-length PpPIR2 containing the putative secretion signal peptide and anchor domain peptide sequences to a sequence encoding a heterologous polypeptide as provided by the instant invention results in display of the expressed polypeptide on the surface a transformed host cell.

The PpPIR1 and PpPIR2 secretion signal peptide and/or anchor domain regions may be operably linked to a sequence encoding a heterologous polypeptide to provide for efficient secretion and/or cell surface display of the heterologous protein in yeast including but not limited to *Pichia*. For example, the PpPIR1 secretion signal peptide sequence provided herein is an alternative to vectors using the native secretion signal sequence of the protein of interest, the secretion signal sequence of *P. pastoris* acid phosphatase (PHO1) or the secretion signal sequence of *S. cerevisiae* α-mating factor (α-MF) for the secretion of heterologous proteins. Additionally, the full-length PpPIR1 and PpPIR2 sequences and anchor domain sequences derived therefrom that are provided herein are alternatives for the expression of heterologous polypeptides for cell surface display in yeast. Accordingly, the PpPIR1 and PpPIR2 secretion signal peptide and/or anchor domain sequences provided herein can be used for yeast expression systems wherein the heterologous protein is transferred from the intracellular environment of the host cell to either the culture media or to the cell surface.

PpPIR1 Secretion Signal Peptide Recombinant Nucleic Acid Constructs

One aspect of the invention is a recombinant nucleic acid construct having a nucleic acid sequence encoding a secretion signal peptide that is operably linked to both a heterologous expression control sequence and a heterologous nucleic acid sequence comprising a site for operable insertion of a nucleic acid sequence encoding a polypeptide. The nucleic acid sequence encoding a secretion signal peptide has at least about 70% sequence identity to the amino acid sequence of SEQ ID NO: 15 and is operably linked to both a heterologous expression control sequence and a heterologous nucleic acid sequence comprising a site for operable insertion of a nucleic acid sequence encoding a polypeptide. In other aspects, the nucleic acid sequence encoding a secretion signal peptide has at least about 80%, 90%, 95%, 98%, or 99% sequence identity to the amino acid sequence of SEQ ID NO: 15. The recombinant nucleic acid construct may be DNA or RNA.

In certain embodiments, the recombinant nucleic acid construct may have a nucleic acid sequence encoding a heterologous polypeptide inserted into the site for operable insertion. The nucleic acid sequence encoding a heterologous polypeptide may encode any heterologous gene of interest. Examples of heterologous polypeptides encoded by the nucleic acid sequence include, but are not limited to, EGFP, human serum albumin, antibodies, tumor necrosis factor, bovine lysozyme, human lysozyme, and other polypeptides of interest. When inserted into the site for operable insertion, the sequence encoding the heterologous polypeptide is operably linked to the nucleic acid sequence encoding a secretion signal peptide. The linkage is made so that the first translational initiation codon contained in the 5' untranslated sequence associated with the sequence encoding a secretion signal peptide is linked such that the resulting translation product is in frame with the translational open reading frame that encodes the protein desired. Thus, the resulting expression product is oriented such that the C-terminus of the secretion signal is operably linked to the N-terminus of the heterologous polypeptide.

Additionally, multiple expression copies may be introduced into a recombinant nucleic acid construct to construct a multiple expression cassette copy recombinant nucleic acid construct. For example, the heterologous gene is inserted into the recombinant nucleic acid construct at the site for operable insertion of a nucleic acid sequence encoding a polypeptide. The resulting single cassette vector containing, for example, a promoter, a PpPIR1 secretion signal peptide sequence, a heterologous gene, and additional sequences, is then digested with restriction endonucleases to excise the single cassette expression vector. The single cassette expression vector is then reinserted into a second recombinant nucleic acid construct containing one or more expression cassette(s) to create tandem repeats of the expression cassette. The reinsertion process may be repeated to generate a series of recombinant nucleic acid constructs containing increasing numbers of expression cassettes.

In certain embodiments, the heterologous expression control sequence may be a promoter. The promoter may be a constitutive promoter. A "constitutive" promoter is a promoter that is active under most environmental and developmental conditions. Alternatively, the promoter may be an inducible promoter. An "inducible" promoter is a promoter that is active under environmental or developmental regulation. Promoters useful for controlling gene expression may be, for example, Alcohol Oxidase I (AOX1) promoter, Alcohol Oxidase II (AOX2) promoter, GAP promoter, FLD1 promoter, YTP1 promoter, and PEX8 promoter. The AOX1 and AOX2 promoters are inducible promoters that may be induced by addition of methanol into the culture medium. The GAP and YTP1 promoters are constitutive promoters. The FLD1 promoter is an inducible promoter that may be induced by the addition of methanol or methylamine into the culture medium. The PEX8 promoter is an inducible promoter that may be induced by the addition of methanol or oleate into the culture medium.

The site for operable insertion can comprise any sequence that provides for operable insertion of the heterologous sequence in the recombinant nucleic acid. In certain embodiments, the heterologous sequence comprising a site for operable insertion of a sequence that encodes a heterologous polypeptide comprises at least one restriction endonuclease recognition sequence. Restriction endonucleases and their recognition sequences are routinely used in the art to combine nucleic acid sequences to form recombinant nucleic acid constructs wherein joined sequences are operably linked. Further, it is understood that the restriction endonucleases and their recognition sequences disclosed herein are non-limiting examples and that other such restriction endonucleases and their recognition sequences not explicitly cited herein may be employed in the practice of the current invention. In still other embodiments, the site for operable insertion of the heterologous sequence can comprise a site for integration by homologous recombination. In still other embodiments, the site for operable insertion of the heterologous sequence can comprise a site-specific recombination recognition sequence. Examples of site-specific recombination recognition sequences include, but are not limited to, lox sites recognized by a bacteriophage P1 Cre recombinase, or FRT sites recognized by a yeast FLP recombinase. In still other embodiments, the site for operable insertion can comprise a Ligation Independent Cloning site that provides for DNA topoisomerase I mediated integration of the heterologous coding sequence. Various methods for operable insertion of heterologous sequences into specified sites in U.S. Pat. No. 7,109,178, which is incorporated herein by reference with respect to its disclosure of Ligation Independent Cloning and directional cloning.

The recombinant nucleic acid constructs may have additional operably linked sequences. Examples of additional operably linked sequences include, a polyadenylation sequence, regulatory elements, enhancers, restriction enzyme sites, selection markers such as a biosynthetic gene marker (for example, HIS4, ARG4, ADE1, URA3, and URA5), and/or a drug-resistance marker (for example, Kan$^R$, Zeo$^R$, Bsd$^R$, FLD1).

Isolation of Nucleic Acids Comprising A PpPIR1Secretion Signal Peptide

Another aspect of the invention is an isolated nucleic acid comprising a nucleotide sequence encoding a secretion signal peptide that has at least 70% identity to SEQ ID NO: 14. The isolated nucleic acid encoding the PpPIR1 secretion signal peptide that has at least 70% identity to SEQ ID NO: 14 may be operably linked to a nucleic acid sequence encoding a heterologous polypeptide.

Transformed Cells

Another aspect of the invention is a transformed cell having a nucleotide sequence encoding a secretion signal peptide that has at least 70% identity to SEQ ID NO: 14 that is operably linked to a nucleic acid sequence encoding a heterologous polypeptide. The transformed cell may be a yeast cell or a bacterial cell. Examples of bacterial cells include, but are not limited to, *E. coli* or *Salmonella* sp. cells. Examples of yeast cells that may be transformed include, a *Pichia* cell, a *Saccharomyces* cell, a *Kluyveromyces* cell, a *Candida* cell, a *Torulopsis* cell, a *Hansenula* cell, and a *Yarrowia* cell. The transformed cell may have a single or multiple copies of the recombinant nucleic acid construct or constructs containing multiple expression cassette copies.

A cell is transformed by introducing the recombinant nucleic acid construct into the cell. Recombinant nucleic acid constructs may be introduced into the cell using a variety of standard methods. For example, cells may be transformed by methods that include, but are not limited to, chemical transfection, liposome-mediated transfection, microprojectile-mediated delivery, and electroporation.

Methods for Obtaining Heterologous Polypeptides

A further aspect of the invention is a method for obtaining a heterologous polypeptide. In one embodiment, the method comprises culturing a cell transformed with a recombinant nucleic acid construct having a heterologous expression control sequence, a sequence encoding a secretion signal peptide that has at least about 70% sequence identity to the amino acid sequence of SEQ ID NO: 15, and a sequence encoding a heterologous polypeptide. The heterologous expression control sequence, the sequence encoding a secretion signal peptide, and the sequence encoding a heterologous polypeptide are operably linked. In other embodiments, the sequence encoding the heterologous peptide may be operably linked to a sequence encoding an epitope tag, a polyhistidine tag, or other peptide sequence that provides for detection and/or purification of the heterologous peptide. The heterologous polypeptide may be recovered from the cell or a culture medium.

The heterologous polypeptide may be used with or without further purification from the culture medium. If further purification from the culture medium is desired, the heterologous polypeptide may be recovered from the culture medium according to a variety of standard methods for protein purification. Examples of protein purification include affinity chromatography, precipitation, chromatography, extraction, ultrafiltration, and electrophoresis. Although the presence of the secretion signal sequence should result in secretion of the heterologous polypeptide into the culture medium, some of the heterologous polypeptide may remain within the cell. Recovery of the heterologous polypeptide from the cell may be accomplished using standard methods for protein purification.

Kits

The invention also contemplates kits for producing a recombinant nucleic acid constructs or transformed host cells for obtaining heterologous proteins secreted into the culture medium. In one aspect, a kit has a recombinant nucleic acid construct and instructions for the use thereof. The recombinant nucleic acid construct of the kit has a nucleic acid sequence encoding a secretion signal peptide that has at least about 70% sequence identity to the amino acid sequence of SEQ ID NO: 15 and is operably linked to both a heterologous expression control sequence and a heterologous nucleic acid sequence having a site for operable insertion of a nucleic acid sequence encoding a polypeptide. The instructions of the kit may describe how to use the recombinant nucleic acid construct contained within the kit. The instructions may be provided, for example, within the packaging of the kit, on the packaging, and on a website.

Full-length Recombinant Nucleic Aid Constructs For Surface Display

Full-length PpPIR1 Recombinant Nucleic Aid Constructs

Another aspect of the invention is a recombinant nucleic acid construct comprising a nucleic acid sequence encoding an anchor domain peptide that is operably linked to both a heterologous expression control sequence and a heterologous nucleic acid sequence comprising a site for operable insertion of a nucleic acid sequence encoding a polypeptide. Also in the nucleic acid sequence is a secretion signal sequence that directs the translated protein to the secretory pathway. The secretion signal peptide sequence include, but are not limited to, the native secretion signal sequence of a protein of interest, a *P. pastoris* acid phosphatase (PHO1) secretion signal sequence, a *S. cerevisiae* α-mating factor (α-MF) secretion signal sequence, a *P. pastoris* PIR secretion signal sequence, a *S. cerevisiae* PIR secretion signal sequence, a *P. acaciae* killer toxin secretion signal sequence, and other secretion signal sequences useful for the secretion of heterologous proteins. In one embodiment, the sequence encoding an anchor domain peptide has at least about 70% sequence identity to the amino acid sequence of SEQ ID NO: 2 and is operably linked to both a heterologous expression control sequence and a heterologous nucleic acid sequence comprising a site for operable insertion of a nucleic acid sequence encoding a polypeptide. In other embodiments, the nucleic acid sequence encoding the anchor domain peptide encodes a protein having at least about 80%, about 90%, about 95%, about 98% or about 99% sequence identity to the amino acid sequence of SEQ ID NO: 2. The recombinant nucleic acid construct may be DNA or RNA.

In certain embodiments, the recombinant nucleic acid construct may have a nucleic acid sequence encoding a heterologous polypeptide inserted into the site for operable insertion. The nucleic acid sequence encoding a heterologous polypeptide may encode any heterologous gene of interest. Examples of heterologous polypeptides encoded by the nucleic acid sequence may include, but are not limited to, EGFP, human serum albumin, antibodies, tumor necrosis factor, bovine lysozyme, human lysozyme, and other polypeptides. When inserted into the site for operable insertion, the sequence encoding the heterologous polypeptide is operably linked to the nucleic acid sequence encoding a anchor domain peptide. Thus, the resulting expression product may be oriented such that the C-terminus of the PpPIR1 anchor domain peptide is operably linked to the N-terminus of the heterologous polypeptide. In certain embodiments, the C-terminus of the PpPIR1 anchor domain peptide is operably linked to the N-terminus of the heterologous polypeptide.

Additionally, multiple expression copies may be introduced into a recombinant nucleic acid construct to construct a multiple expression cassette copy recombinant nucleic acid construct. For example, the heterologous gene is inserted into the recombinant nucleic acid construct at the site for operable insertion of a nucleic acid sequence encoding a polypeptide. The resulting single cassette vector containing, for example, a promoter, a PpPIR1 anchor domain peptide sequence, the heterologous gene, and additional sequences, is digested then with restriction endonucleases to excise the single cassette expression vector. The single cassette expression vector is then reinserted into a second recombinant nucleic acid construct containing a single copy expression cassette to create a tandem repeat of the cassette. The reinsertion process may be repeated to generate a series of recombinant nucleic acid constructs containing increasing numbers of expression cassettes.

In certain embodiments, the heterologous expression control sequence may be a promoter. The promoter may be a constitutive promoter. A "constitutive" promoter is a promoter that is active under most environmental and developmental conditions. Alternatively, the promoter may be an inducible promoter. An "inducible" promoter is a promoter that is active under environmental or developmental regulation. Promoters useful for controlling gene expression may be, for example, Alcohol Oxidase I (AOX1) promoter, Alcohol Oxidase II (AOX2) promoter, GAP promoter, FLD1 promoter, YTP1 promoter, and PEX8 promoter. The AOX1 and AOX2 promoters are inducible promoters that may be induced by addition of methanol into the culture medium. The GAP and YTP1 promoters are constitutive promoters. The FLD1 promoter is an inducible promoter that may be induced by the addition of methanol or methylamine into the culture medium. The PEX8 promoter is an inducible promoter that may be induced by the addition of methanol or oleate into the culture medium.

The site for operable insertion can comprise any sequence that provides for operable insertion of the heterologous sequence in the recombinant nucleic acid. In certain embodiments, the heterologous sequence comprising a site for operable insertion of a sequence that encodes a heterologous polypeptide comprises at least one restriction endonuclease recognition sequence. Restriction endonucleases and their recognition sequences are routinely used in the art to combine nucleic acid sequences to form recombinant nucleic acid constructs wherein joined sequences are operably linked. Further, it is understood that the restriction endonucleases and their recognition sequences disclosed herein are non-limiting examples and that other such restriction endonucleases and their recognition sequences not explicitly cited herein may be employed in the practice of the current invention. In still other embodiments, the site for operable insertion of the heterologous sequence can comprise a site for integration by homologous recombination. In still other embodiments, the site for operable insertion of the heterologous sequence can comprise a site-specific recombination recognition sequence. Examples of site-specific recombination recognition sequences include, but are not limited to, lox sites recognized by a bacteriophage P1 Cre recombinase, or FRT sites recognized by a yeast FLP recombinase. In still other embodiments, the site for operable insertion can comprise a Ligation Independent Cloning site that provides for DNA topoisomerase I mediated integration of the heterologous coding sequence. Various methods for operable insertion of heterologous sequences into specified sites in U.S. Pat. No. 7,109,178, which is incorporated herein by reference with respect to its disclosure of Ligation Independent Cloning and directional cloning.

The recombinant nucleic acid constructs may have additional sequences such as, for example, a polyadenylation sequence, regulatory elements, enhancers, restriction enzyme sites, selection markers such as a biosynthetic gene marker, for example, HIS4, ARG4, ADE1, URA3, and URA5, and/or a drug-resistance marker, for example, $Kan^R$, $Zeo^R$, $Bsd^R$, FLD1.

Isolation of Nucleic Acids Comprising a PpPIR1 Anchor Domain Peptide

Another aspect of the invention is an isolated nucleic acid comprising a nucleotide sequence encoding an anchor domain peptide that has at least 70% identity to SEQ ID NO: 1. The isolated nucleic acid encoding the anchor domain peptide that has at least 70% identity to SEQ ID NO: 1 may be operably linked to a nucleic acid sequence encoding a heterologous polypeptide. In other aspects, the nucleic acid sequence encoding the anchor domain peptide has at least about 80%, about 90%, about 95%, about 98% or about 99% sequence identity to SEQ ID NO: 1.

Transformed Cells

Another aspect of the invention is a transformed cell having a nucleotide sequence encoding an anchor domain peptide that has at least about 70% identity to the amino acid sequence of SEQ ID NO: 2 that is operably linked to a nucleic acid sequence encoding a heterologous polypeptide. The transformed cell may be a yeast cell or a bacterial cell. Examples of bacterial cells, include, but are not limited to, *E. coli* or *Salmonella* sp. cells. Yeast cells include, but are not limited to, a *Pichia* cell, a *Saccharomyces* cell, a *Kluyveromyces* cell, a *Candida* cell, a *Torulopsis* cell, a *Hansenula* cell, and a *Yarrowia* cell. The transformed cell may have a single or multiple copies of the recombinant nucleic acid construct of constructs containing multiple expression cassette copies.

A cell is transformed by introducing the recombinant nucleic acid construct into the cell. Recombinant nucleic acid constructs may be introduced into the cell using a variety of standard methods. For example, cells may be transformed by methods that include, but are not limited to, chemical transfection, liposome-mediated transfection, microprojectile-mediated delivery, and electroporation.

Methods for Surface Display of Heterologous Polypeptides Using PpPIR1

A further aspect of the invention is a method for surface display of a heterologous polypeptide. The method for expressing a heterologous polypeptide on a host cell comprises culturing a cell transformed with a recombinant nucleic acid construct having a heterologous expression control sequence, a sequence encoding an anchor domain peptide that has at least about 70% sequence identity to the amino acid sequence of SEQ ID NO: 2, and a sequence encoding a heterologous polypeptide. The heterologous expression control sequence, the sequence encoding an anchor domain peptide, and the sequence encoding a heterologous polypeptide are operably linked. The cell is cultured under conditions permitting expression of the heterologous polypeptide, thereby expressing the heterologous polypeptide on the host cell. The transformed cell displaying the heterologous polypeptide on the surface may, for example, be used for recovering the host cell displaying the heterologous polypeptide on the cell, screening antibody libraries, antibody-antigen disassociation kinetics, and cell sorting. Alternatively, the heterologous polypeptide displayed on the cell surface may be recovered from the host cell expressing the heterologous polypeptide on the host cell. The heterologous polypeptide may be removed from the host cell surface by standard methods. Examples of methods for removing the heterologous polypeptide displayed on the cell surface include, but are not limited to, SDS under reducing conditions, β-glucanases, and other methods. Recovery of the heterologous polypeptide may be accomplished using standard methods for protein purification. Examples of protein purification include affinity chromatography, precipitation, chromatography, extraction, ultrafiltration, and electrophoresis.

Full-Length PpPIR2Recombinant Nucleic Aid Constructs

In another embodiment, the anchor domain peptide has at least about 70% sequence identity to the amino acid sequence of SEQ ID NO: 4 and is operably linked to both a heterologous expression control sequence and a heterologous nucleic acid sequence comprising a site for operable insertion of a nucleic acid sequence encoding a polypeptide. In other aspects, the nucleic acid sequence encoding the anchor domain peptide has at least about 80%, about 90%, about 95%, about 98% or about 99% sequence identity to the amino acid sequence of SEQ ID NO: 4. The recombinant nucleic acid construct may be DNA or RNA.

In certain embodiments, the recombinant nucleic acid construct may have a nucleic acid sequence encoding a heterologous polypeptide inserted into the site for operable insertion. The nucleic acid sequence encoding a heterologous polypeptide may encode any heterologous gene of interest. Examples of heterologous polypeptides encoded by the nucleic acid sequence include, but are not limited to, EGFP, human serum albumin, antibodies, tumor necrosis factor, bovine lysozyme, human lysozyme, and other polypeptides. When inserted into the site for operable insertion, the sequence encoding the heterologous polypeptide is operably linked to the nucleic acid sequence encoding a secretion signal peptide. Thus, the resulting expression product is oriented such that the C-terminus of the PpPIR2 anchor domain peptide is operably linked to the N-terminus of the heterologous polypeptide.

Additionally, multiple expression copies may be introduced into a recombinant nucleic acid construct to construct a multiple expression cassette copy recombinant nucleic acid construct. For example, the heterologous gene is inserted into the recombinant nucleic acid construct at the site for operable insertion of a nucleic acid sequence encoding a polypeptide. The resulting single cassette vector containing, for example, a promoter, a PpPIR2 anchor domain peptide sequence, the heterologous gene, and additional sequences, is digested then with restriction endonucleases to excise the single cassette expression vector. The single cassette expression vector is then reinserted into a second recombinant nucleic acid construct containing a single copy expression cassette to create a tandem repeat of the cassette. The reinsertion process may be repeated to generate a series of recombinant nucleic acid constructs containing increasing numbers of expression cassettes.

In certain embodiments, the heterologous expression control sequence may be a promoter. The promoter may be a constitutive promoter. A "constitutive" promoter is a promoter that is active under most environmental and developmental conditions. Alternatively, the promoter may be an inducible promoter. An "inducible" promoter is a promoter that is active under environmental or developmental regulation. Promoters useful for controlling gene expression may be, for example, Alcohol Oxidase I (AOX1) promoter, Alcohol Oxidase II (AOX2) promoter, GAP promoter, FLD1 promoter, YTP1 promoter, and PEX8 promoter. The AOX1 and AOX2 promoters are inducible promoters that may be induced by addition of methanol into the culture medium. The GAP and YTP1 promoters are constitutive promoters. The FLD1 promoter is an inducible promoter that may be induced by the addition of methanol or methylamine into the culture medium. The PEX8 promoter is an inducible promoter that may be induced by the addition of methanol or oleate into the culture medium.

The site for operable insertion can comprise any sequence that provides for operable insertion of the heterologous sequence in the recombinant nucleic acid. In certain embodiments, the heterologous sequence comprising a site for operable insertion of a sequence that encodes a heterologous polypeptide comprises at least one restriction endonuclease recognition sequence. Restriction endonucleases and their recognition sequences are routinely used in the art to combine nucleic acid sequences to form recombinant nucleic acid constructs wherein joined sequences are operably linked. Further, it is understood that the restriction endonucleases and their recognition sequences disclosed herein are non-limiting examples and that other such restriction endonucleases and their recognition sequences not explicitly cited herein may be employed in the practice of the current invention. In still other embodiments, the site for operable insertion of the heterologous sequence can comprise a site for integration by homologous recombination. In still other embodiments, the site for operable insertion of the heterologous sequence can comprise a site-specific recombination recognition sequence. Examples of site-specific recombination recognition sequences include, but are not limited to, lox sites recognized by a bacteriophage P1 Cre recombinase, or FRT sites recognized by a yeast FLP recombinase. In still other embodiments, the site for operable insertion can comprise a Ligation Independent Cloning site that provides for DNA topoisomerase I mediated integration of the heterologous coding sequence. Various methods for operable insertion of heterologous sequences into specified sites in U.S. Pat. No. 7,109,178, which is incorporated herein by reference with respect to its disclosure of Ligation Independent Cloning and directional cloning.

The recombinant nucleic acid constructs may have additional sequences such as, for example, a polyadenylation sequence, regulatory elements, enhancers, restriction enzyme sites, selection markers such as a biosynthetic gene marker, for example, HIS4, ARG4, ADE1, URA3, and URA5, and/or a drug-resistance marker, for example, $Kan^R$, $Zeo^R$, $Bsd^R$, FLD1.

Isolation of Nucleic Acids Comprising A PpPIR2Anchor Domain Peptide

Another aspect of the invention is an isolated nucleic acid comprising a nucleotide sequence encoding an anchor domain peptide that has at least 70% identity to SEQ ID NO: 3. The isolated nucleic acid encoding the anchor domain peptide that has at least 70% identity to SEQ ID NO: 3 may be operably linked to a nucleic acid sequence encoding a heterologous polypeptide.

Transformed Cells

Another aspect of the invention is a transformed cell having a nucleotide sequence encoding an anchor domain peptide that has at least about 70% identity to the amino acid sequence of SEQ ID NO: 4 that is operably linked to a nucleic acid sequence encoding a heterologous polypeptide. The transformed cell is a yeast cell such as, for example, a *Pichia* cell, a *Saccharomyces* cell, a *Kluyveromyces* cell, a *Candida* cell, a *Torulopsis* cell, a *Hansenula* cell, or a *Yarrowia* cell. The transformed cell may have a single or multiple copies of the recombinant nucleic acid construct of constructs containing multiple expression cassette copies.

A cell is transformed by introducing the recombinant nucleic acid construct into the cell. Recombinant nucleic acid constructs may be introduced into the cell using a variety of standard methods. For example, cells may be transformed by methods that include, but are not limited to, chemical transfection, liposome-mediated transfection, microprojectile-mediated delivery, and electroporation.

Methods for Surface Display of Heterologous Polypeptides Using PpPIR2

A further aspect of the invention is a method for surface display of a heterologous polypeptide. The method for expressing a heterologous polypeptide on a host cell comprises culturing a cell transformed with a recombinant nucleic acid construct having a heterologous expression control sequence, a sequence encoding an anchor domain peptide that has at least about 70% sequence identity to the amino acid sequence of SEQ ID NO: 4 and a sequence encoding a heterologous polypeptide. The heterologous expression control sequence, the sequence encoding an anchor domain peptide, and the sequence encoding a heterologous polypeptide are operably linked. The cell is cultured under conditions permitting expression of the heterologous polypeptide, thereby expressing the heterologous polypeptide on the host cell. The transformed cell displaying the heterologous polypeptide on the surface may, for example, be used for recovering the host cell displaying the heterologous polypeptide on the surface, screening antibody libraries, antibody-antigen disassociation kinetics, and cell sorting. Alternatively, the heterologous polypeptide displayed on the host cell surface may be recovered from the host cell expressing the heterologous polypeptide on the cell. The heterologous polypeptide may be removed from the cell surface by standard methods. Examples of methods for removing the heterologous polypeptide displayed on the cell surface include, but are not limited to, SDS under reducing conditions, β-glucanases, and other methods. Recovery of the heterologous polypeptide may be accomplished using standard methods for protein purification. Examples of protein purification include affinity chromatography, precipitation, chromatography, extraction, ultrafiltration, and electrophoresis.

Kits

The invention also contemplates kits for producing a recombinant nucleic acid constructs or transformed host cells for expressing a heterologous polypeptide on a cell surface. In one aspect, the kit may contain a recombinant nucleic acid construct having a nucleic acid sequence encoding an anchor domain peptide that has at least about 70% sequence identity to the amino acid sequence of SEQ ID NO: 2. In another aspect, the kit may contain a recombinant nucleic acid construct having a nucleic acid sequence encoding an anchor domain peptide that has at least about 70% sequence identity to the amino acid sequence of SEQ ID NO: 4. The instructions of the kit may describe how to use the recombinant nucleic acid construct contained within the kit. The instructions may be provided, for example, within the packaging of the kit, on the packaging, and on a website.

EXAMPLES

The following examples describe embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

Example 1

Description of Chemicals, Enzymes, Strains, and Culture Media

Cultivation media constituents for *E. coli* and *Pichia pastoris* were purchased from Difco Laboratories (USA). All primers were synthesized by Integrated DNA Technologies (USA). All chemicals were of analytical grade. DIG labeling southern blot kit was purchased from Roche Applied Science (Indianapolis, Ind., USA). Western blot kit was purchased from Amersham Biosciences (Piscataway, N.J., USA). All PCR reactions were done with PfuTurbo hotstart DNA polymerase purchased from Stratagene (La Jolla, Calif., USA).

Zeocin was obtained from Invitrogen (Carlsbad, Calif.). All restriction enzymes were from New England Biolabs (Ipswich, Mass.).

TOP10 E. coli cells (F-mcrA Δ(mrr-hsdRMS-mcrBC) φ80lacZΔM15 ΔlacX74 recA1 araD139 Δ(ara-leu) 7697 galU galK rpsL (StrR) endA1 nupG) (Invitrogen, USA) or NEB Turbo Competent E. coli (New England Biolabs) were used for cloning and plasmid propagations with an appropriate antibiotic concentration. The P. pastoris KM71H strain and expression plasmids were obtained from Invitrogen. E. coli cells were grown in LB Lennox media. P. pastoris KM71 cells were grown in YPD medium containing 2% peptone, 1% yeast extract and 2% dextrose whereas YPDS plates were supplemented with 1.0 M sorbitol and 1.5% agar. BMGY contained 2% peptone, 1% yeast extract, 1% glycerol, 1.34% yeast nitrogen base with ammonium sulphate (without amino acids) 4×10-5% biotin and 100 mM phosphate buffer pH 7. BMMY media substituted 0.5% methanol for glycerol. LB Lennox media contained 1% tryptone, 0.5% yeast extract and 0.5% sodium chloride.

Primer Sequences for Plasmid Construction

Example 2

Isolation of the *Pichia pastoris* PIR1 Gene Sequence

The full length DNA sequence of the *Pichia pastoris* PIR1 ("PpPIR1") gene was isolated using PIR1F (SEQ ID NO: 5) and PIR1R (SEQ ID NO: 6) primers and a *P. pastoris* cDNA library as template for Polymerase Chain Reaction (PCR). The ~1.1 kb PCR product was ligated into pCR-Blunt II-TOPO vector using the Zero Blunt TOPO PCR Cloning Kit (Invitrogen, Carlsbad, Calif.). Sequencing of the pCR-Blunt II-TOPO/PpPIR1 plasmid confirmed that the PCR product contained a 1068 bp PpPIR1 gene open reading frame (SEQ ID NO: 1).

Example 3

Isolation of the *Pichia Pastoris* PIR2 Gene Sequence

The full length DNA sequence of the *Pichia pastoris* PIR2 ("PpPIR2") sequence was isolated using PIR2F (SEQ ID NO:

TABLE 4

Primer sequence list.

| Gene | Primer Name | Sequence | Purpose |
|---|---|---|---|
| PIR1 | PIR1F | ATGTACAGGAACTTAATAATTGCTAC SEQ ID NO: 5 | Forward primer for PIR1 secretion signal sequence and PIR1 full length sequence |
| PIR1 | PIR1R | TTAACACTCTATGAGGTCTAC SEQ ID NO: 6 | Reverse primer for full length PIR1 |
| PIR1 | PIR1LEcoR | GGGAATTCTCTCTTAATCTTGTCGGCATC SEQ ID NO: 7 | Reverse primer for PIR1 secretion signal sequence with EcoRI site |
| PIR1 | PIR1FSfu | TATTCGAAACGATGTACAGGAACTTAATAAT TGC SEQ ID NO: 8 | Forward primer for PIR1 with SfuI site |
| PIR1 | PIR1NOSTP | AAAGAATTCACACTCTATGAGGTCTACAATG SEQ ID NO: 9 | Reverse primer for Full length PIR1 sequence without Stop codon with EcoRI site |
| EGFP | EGFPFECORI | AAAGAATTCATGGTGAGCAAGGGCGAG SEQ ID NO: 36 | Forward primer for EGFP |
| EGFP | EGFPRNOTI | AAGCGGCCGCTTACTTGTACAGCTCGTCCA TG SEQ ID NO: 37 | Reverse primer for EGFP |
| PIR2 | PIR2F | CCATATCCAGAAGTATCAGATG SEQ ID NO: 10 | Forward primer for PIR2 |
| PIR2 | PIR2R | ACTGTGATTCGCCTTCAGG SEQ ID NO: 11 | Reverse primer for PIR2 |
| P1R2 | PIR2SfuI | TATTCGAAACGATGAAGCTCGCTGCACTCT C SEQ ID NO: 12 | Forward primer PIR2 with SfuI site |
| PIR2 | PIR2NOSTP | GGGAATTCACATGAAATGAGATCAACAG SEQ ID NO: 13 | Reverse primer for PIR2 without Stop codon with EcoRI site |
| PIR2 | PIR2LEcoR | GAGAATTCAACAACATGAGTCGTAGTAGC SEQ ID NO: 34 | Reverse primer for PIR2 secretion signal sequence with EcoR1 site |

10) and PIR2R (SEQ ID NO: 11) primers and a *P. pastoris* cDNA library as template for PCR. The ~1.25 kb fragment was ligated into pCR-Blunt II-TOPO vector using the Zero Blunt TOPO PCR Cloning Kit. Sequencing of the pCR-Blunt II-TOPO/PpPIR2 plasmid confirmed that the PCR product contained a 972 bp PpPIR2 open reading frame (SEQ ID NO: 3).

Example 4

Construction of AOX1-PpPIR1Secretion Signal-EGFP Recombinant Nucleic Acid Construct To construct a recombinant nucleic acid construct under the control of an inducible promoter (AOX1) for the expression and secretion of EGFP, the PpPIR1 secretion signal sequence was POR amplified from the plasmid (pCR-Blunt II-TOPO/PpPIR1) having complete the *P. pastoris* PIR1 gene using PIRSfu forward primer (SEQ ID NO: 8) and PIR1LEcoR reverse primer (SEQ ID NO: 7). The PCR product was digested with SfuI and EcoRI restriction enzymes and ligated into the pPICZA plasmid that was digested with same restriction enzymes. The pPICZA plasmid contains the AOX1 promoter. The resultant pPICZA-PIR1SIG vector was sequenced to confirm the accuracy of the PpPIR1 secretion signal sequence. The EGFP gene was PCR amplified from a pPICZA-EGFP plasmid having the gene encoding EGFP as template using EGFPFECORI (SEQ ID NO: 36) and EGFPRNOTI (SEQ ID NO: 37) primers. Sequencing confirmed that the pPICZA/EGFP plasmid contained the open reading frame for Enhanced Green Fluorescent Protein. The pPICZA/EGFP plasmid was digested with EcoRI and NotI restriction enzymes and ligated into the pPICZAPIR1 vector that was digested with the same restriction enzymes. The plasmid was named pPICZIPIR1L/EGFP (FIG. 4).

Example 5

Construction of GAP-PpPIR1Secretion Signal-EGFP Recombinant Nucleic Acid Construct To construct a recombinant nucleic acid construct under the control of a constitutive promoter for the expression and secretion of EGFP, the EGFP gene was cloned under the GAP promoter and operably linked to the PpPIR1 secretion signal sequence by ligating the SfuI/NotI fragment of pPICZ/PIR1L/EGFP to a pGAPZA vector digested with same restriction enzymes. The final vector was named pGAPZ/PIR1L/EGFP (FIG. 5).

Example 6

Construction of AOX1-PpPIR1 Anchor Domain Peptide-EGFP Recombinant Nucleic Acid Construct To construct a recombinant nucleic acid construct under the control of an inducible promoter (AOX1) for the expression of EGFP on the cell surface, the full-length PpPIR1 sequence was PCR amplified using the pCR-Blunt II-TOPO/PpPIR1 as template and PIR1FSfu forward primer (SEQ ID NO: 8) and PIR1NOSTP reverse primer (SEQ ID NO: 9). This PCR product contained the full-length PpPIR1 sequence without the stop codon (TAA) and introduced SfuI and EcoRI restriction sites 5' and 3' of the PpPIR1 gene sequence, respectively. The PCR product was digested with SfuI and ECoRI and ligated into pPICZA digested with same enzymes. The resultant plasmid was named pPICZ/PIR1NOSTP. The plasmid pCR-Blunt II-TOPO/EGFP was digested with EcoRI and NotI enzymes and the fragment containing EGFP gene was subcloned into pPICZ/PIR1NOSTP that was digested with EcoRI and NotI restriction enzymes. The final plasmid was named pPICZ/PIR1/EGFP and contained the sequence encoding the full-length PpPIR1 operably linked to the N-terminus of the sequence encoding the EGFP protein as single open reading frame (FIG. 6).

Example 7

Construction of GAP-PpPIR1 Anchor Domain Peptide-EGFP Recombinant Nucleic Acid Construct To construct a recombinant nucleic acid construct under the control of a constitutive promoter (GAP) for the expression of EGFP on the cell surface, the pPICZ/PIR1/EGFP plasmid was digested with SfuI and NotI. The resulting fragment containing the PpPIR1/EGFP fusion was gel purified and ligated into a pGAPZA vector that was digested with SfuI and NotI restriction enzymes. The resulting plasmid was named pGAPZ/PIR1/EGFP (FIG. 7).

Example 8

Construction of AOX1-PpPIR2Anchor Domain Peptide-EGFP Recombinant Nucleic Acid Construct A recombinant nucleic acid construct under the control of an inducible promoter for the expression of EGFP on the cell surface was constructed using the PpPIR2 sequence. PpPIR2 was PCR amplified from the pCR-Blunt II-TOPO/PIR2 as template using forward primer PIR2Sfu (SEQ ID NO: 12) and reverse primer PIR2NOSTP (SEQ ID NO: 13). The resultant PCR product contained the full-length PpPIR2 sequence without a stop codon (TGA) and introduced SfuI and EcoRI restriction sites 5' and 3' of the gene, respectively. The PCR product was digested with SfuI and EcoRI and ligated into pPICZA that was digested with the same enzymes. The resulting plasmid was named pPICZ/PIR2NOSTP. The EGFP gene was excised from the pPICZA/EGFP plasmid with EcoRI and NotI restriction enzymes and ligated into pPICZ/PIR2NOSTP that was digested with the same restriction enzymes. The resulting plasmid was named pPICZ/PIR2/EGFP (FIG. 8). This plasmid contained the sequence encoding the full-length PpPIR2 protein operably linked to the N-terminus of the sequence encoding EGFP protein as single open reading frame.

Example 9 construction of the GAP-PIR2Anchor Domain Peptide-EGFP Recombinant Nucleic Acid Construct A recombinant nucleic acid construct under the control of a constitutive promoter for the expression of EGFP on the cell surface was constructed using the PpPIR2 sequence. The pPICZ/PIR2/EGFP plasmid was digested with the SfuI and NotI restriction enzymes. The fragment containing the full-length PpPIR2/EGFP fusion was gel purified and ligated into a pGAPZA vector that was digested with the SfuI and NotI restriction enzymes. The resulting plasmid was named pGAPZ/PIR2/EGFP (FIG. 9). This plasmid contained the sequence encoding the full-length PpPIR2 protein operably linked to the N-terminus of the sequence encoding EGFP protein as single open reading frame and under the control of the GAP constitutive promoter.

Example 10

Transformation of P. pastoris Strain KM71H

Preparation of KM71H competent cells were prepared using the standard lithium acetate protocol according to Wu et al. (36 BioTechniques 152-154 (January 2004)). One microgram of the AOX1-based plasmid was linearized with SacI and PmeI restriction enzymes. One microgram of the GAP-based plasmid was linearized with AvrII restriction enzyme. Linearized plasmids were agarose gel purified and transformed into electro-competent KM71H cells (arg4 HIS4, aox1::ARG4) using the gene Pulser Electroporation system (Bio-Rad). Transformants were plated on variable concentration (50, 100, 500 and 1000 mg/L) YSDS Zeocin plates and maintained at 30° C. for 2-3 days until colonies appeared.

Example 11

Shake Flask Studies

For each transformation about ten colonies were picked from YSDS Zeocin plates to test for EGFP expression under the inducible AOX1 promoter. Cells transformed with the AOX-based plasmids (e.g., pPICZ/PIR1L/EGFP) were inoculated into YPD medium and grown overnight at 30° C. Overnight cultures were used to inoculate BMGY Medium to an OD600 of 0.1 and maintained at 30° C. until cells reached an OD600 of 6-8. To induce EGFP expression, cells were collected by centrifugation at 3000×g at 4° C. for 10 minutes and resuspended in BMMY Medium containing methanol at a final concentration of 1%. Every 24 hours, the culture was supplemented with Methanol to a final concentration of 1%. Samples were collected after every 12 hours of induction.

For each transformation about ten colonies were picked from YSDS Zeocin plates to test for EGFP expression under the constitutive GAP promoter. Cells transformed with the GAP-based plasmids (e.g., pGAPZ/PIR1L/EGFP) were inoculated into YPD medium and grown overnight at 30° C. Overnight cultures were used to inoculate YPD medium to an OD600 0.1 and maintained at 30° C. until cells reached an OD600 of 10-15. Cells were harvested after 24 hours.

Example 12

Fluorescence Measurements for EGFP Expression

EGFP was used to test the ability of the expression system to secrete proteins into the culture medium. EGFP fluorescence in the culture medium was measured in arbitrary units using a TD-700 fluorometer (Turner Designs) equipped with a 490 nm excitation filter and a 505 nm emission filter. Culture supernatants from cells transformed with the pPICZPIR1L/EGFP vector were collected at 24, 48, and 72 hours post-induction. Background auto-fluorescence was measured from KM71 host supernatant and subtracted from raw fluorescence units. Results are summarized in Table 5. Culture supernatants of clones expressing EGFP extracellularly (e.g., Clone IDs E-1 to E-5) show dramatically higher fluorescence than culture supernatants of clones expressing EGFP intracellularly (e.g., Clone IDs I-3 and I-8).

TABLE 5

| Arbitrary Fluorescent Unit of culture supernatant | | | |
|---|---|---|---|
| Clone ID | 24 (h) | 48 (h) | 72 (h) |
| KM71H (Host) | 0 | 0 | 0 |
| I-3 (pPICZ/EGFP) (Intra) | 4 | 4 | 17 |
| I-8 (pPICZ/EGFP) (Intra) | 5 | 14 | 20 |
| E-1 (pPICZ/PIR1I/EGFP) Extra | 237 | 270 | 288 |
| E-2 (pPICZ/PIR1I/EGFP) Extra | 265 | 330 | 347 |
| E-3 (pPICZ/PIR1I/EGFP) Extra | 233 | 307 | 327 |
| E-4 (pPICZ/PIR1I/EGFP) Extra | 223 | 283 | 306 |
| E-5 (pPICZ/PIR1I/EGFP) Extra | 200 | 236 | 251 |

Example 13

SDS-PAGE and Western Blot Analysis

Equal volumes of culture supernatants (10 µl) were electrophoresed using 10% Bis-Tris, NuPAGE gels (Novex Precast gel, Invitrogen) under reducing conditions. Following electrophoresis, proteins were electrophoretically transferred to a PVDF membrane (Sigma, USA) for 30 minutes at 25 volt using the wet transfer protocol and Semi dry transfer cell (Bio-Rad, USA). After complete transfer, the membrane was blocked overnight with 5% nonfat milk in TBS buffer pH 7. After washing three times with TBS buffer for 10 minutes, the membrane was incubated with 1:5000 (dilution) of anti-EGFP rabbit polyclonal primary antibody (Abcam Inc., Cambridge, Mass., USA)) for 1 hour. After washing the membrane three times with TBS buffer, the membrane was incubated with 1:10,000 dilution of Goat anti-Rabbit-HRP secondary antibody for 1 h. After three washings, the Western blot was developed on X-ray film using ECL plus detection reagent from Amersham Biosciences (Piscataway, N.J.).

FIG. 10 shows SDS-PAGE analysis of EGFP expression by cells transformed with the PpPIR1 secretion sequence (pPICZ/PIR1L/EGFP construct) under control of the AOX1 promoter. Lanes 8-12 represent culture supernatants from cells transformed with the PpPIR1 secretion sequence (pPICZ/PIR L/EGFP construct) under the control of the AOX1 promoter. Lanes 2-6 represent culture supernatants from cells transformed with EGFP under the control of the AOX1 promoter, but without a secretion signal sequence.

FIG. 11 A is a Western blot of cells transformed with the PpPIR1 secretion sequence under the control of the GAP promoter (lanes 2-10) and cells transformed with the PpPIR1 secretion sequence under the control of the AOX1 promoter (lanes 12). EGFP was detected in the supernatants collected from cells transformed with the plasmids containing the PpPIR1 secretion sequences under the control of either the GAP or AOX1 promoters. FIG. 11 B is a Western blot of cells transformed with the putative PpPIR2 secretion sequence (SEQ ID NO: 17) to determine whether the putative PpPIR2 secretion signal sequence can direct secretion of expressed EGFP. Cells were transformed with the GAP-putative PpPIR2 secretion signal sequence-EGFP construct (see, FIG. 18). Results of a Western analysis of culture supernatants from cells transformed with the GAP-putative PpPIR2 secretion signal sequence-EGFP construct showed that EGFP was not secreted into the media (FIG. 11 B, lanes 2-6 and 8-12). Cells transformed with the AOX1-PpPIR1 secretion signal sequence-EGFP construct were used as a positive control (lane 7). These results showed that cells transformed with the PpPIR1 secretion signal sequence secrete expressed EGFP into the culture medium. Cells transformed with the putative PpPIR2 secretion signal sequence (SEQ ID NO: 17), on the other hand, did secrete EGFP into the culture medium. The putative PpPIR2 secretion signal sequence lacks the KEX2 cleavage site (i.e., KR) that is located at the C-terminus of PpPIR1 (SEQ ID NO: 15) and *S. cerevisiae* PIR1 (SEQ ID NO: 20), PIR2 (SEQ ID NO: 23), PIR3 (SEQ ID NO: 26), PIR4 (SEQ ID NO: 29), and PIR5 (SEQ ID NO: 32). See, FIG. 2. Without being bound to a particular theory, the PpPIR2 secretion signal sequence may contain a cleavage site for another protease.

Example 14

Cell Surface Expression

Single colonies of *P. pastoris* (pPICZ/PIR1/EGFP) and *P. pastoris* (pPICZ/PIR2/EGFP) were used to inoculate 1 mL of BMMY medium in 2.0 mL Eppendorf LidBac tubes with a membrane lid. Cells were grown for 24 hours at 30° C. with shaking using an Eppendorf Thermomixer. Single colonies of *P. pastoris* (pGAP/PIR1/EGFP) and *P. pastoris* (pGAP/PIR2/EGFP) were used to inoculate 1 mL of YPD medium in 2.0 mL Eppendorf LidBac tubes with a membrane lid. Cells were grown for 24 hours at 30° C. with shaking using an Eppendorf Thermomixer. Cells were collected and washed with phosphate-buffered saline (PBS). Cells were resuspended in 1 mL of rabbit anti-GFP IgG Alexa Fluor 647 conjugate (1:200 dilution) and incubated for 1 hour. Cells were washed twice with PBS and resuspended in 1 mL of PBS. A 50 µl aliquot of cells were visualized by confocal laser scanning microscopy (Olympus IX 81).

As shown in FIGS. 12 and 13, *P. pastoris* cells transformed with PpPIR1 under the control of the AOX1 promoter displayed EGFP on the surface. As shown in FIG. 14, *P. pastoris* cells transformed with PpPIR2 under the control of the AOX1 promoter displayed EGFP on the surface. As shown in FIG. 15, *P. pastoris* cells transformed with PpPIR1 under the control of the GAP promoter displayed EGFP on the surface. As shown in FIG. 16, *P. pastoris* cells transformed with PpPIR2 under the control of the GAP promoter displayed EGFP on the surface.

Example 15

Construction of AOX1-PpPIR2Secretion Signal-EGFP Recombinant Nucleic Acid Construct To construct a recombinant nucleic acid construct under the control of an inducible promoter (AOX1) for the expression and secretion of EGFP, the putative PpPIR2 secretion signal sequence was PCR amplified from the plasmid (pCR-Blunt II-TOPO/PpPIR2) having complete the *P. pastoris* PIR2 gene using PIR2SfuI forward primer (SEQ ID NO: 12) and PIR2LEcoR reverse primer (SEQ ID NO: 34). The PCR product was digested with SfuI and EcoRI restriction enzymes and ligated into the pPICZA plasmid that was digested with same restriction enzymes. The pPICZA plasmid contains the AOX1 promoter. The resultant pPICZA/PIR2SIG vector was sequenced to confirm the accuracy of the PpPIR2 secretion signal sequence. The EGFP gene was PCR amplified from a pPICZA-EGFP plasmid having the gene encoding EGFP as template using EGFPFEco and EGFPRNot primers. Sequencing confirmed that the pPICZA/EGFP plasmid contained the open reading frame for Enhanced Green Fluorescent Protein. The pPICZA/EGFP plasmid was digested with EcoRI and NotI restriction enzymes and ligated into the pPICZAPIR2 vector that was digested with the same restriction enzymes. The plasmid was named pPICZ/PIR2L/EGFP (FIG. 17).

Example 16

Construction of GAP-PpPIR2Secretion Signal-EGFP Recombinant Nucleic Acid Construct To construct a recombinant nucleic acid construct under the control of a constitutive promoter for the expression and secretion of EGFP, the EGFP gene was cloned under the GAP promoter and operably linked to the putative PpPIR2 secretion signal sequence by ligating the SfuI/NotI fragment of pPICZ/PIR2L/EGFP to a pGAPZA vector digested with same restriction enzymes. The final vector was named pGAPZ/PIR2L/EGFP (FIG. 18).

Example 17

Construction of PpPIR2Secretion Signal-EGFP Recombinant Nucleic Acid Constructs Containing a KEX2 Cleavage Site The PpPIR2 secretion signal sequence may be engineered to introduce a KEX2 cleavage site (i.e., KR). Site directed mutagenesis may be used to introduce KR at the C-terminal end of the putative PpPIR2 secretion signal peptide (SEQ ID NO: 17). Sequencing would be used to confirm the presence of the KEX2 cleavage site at the C-terminus of the PpPIR2 secretion signal peptide sequence. A recombinant nucleic acid construct containing the engineered PpPIR2 secretion signal sequence-KEX2 sequence could then be operably linked to both a promoter and a nucleic acid sequence encoding a heterologous polypeptide. To determine whether the insertion of the KEX2 cleavage site results in secretion of the heterologous polypeptide, cells would be transformed and the culture medium and cells would be monitored for the presence of the heterologous polypeptide. Identification of the heterologous polypeptide in the medium would indicate that the PpPIR2 secretion signal sequence engineered to have a KEX2 cleavage site resulted in secretion of the heterologous polypeptide.

The discussion of the references herein is intended merely to summarize the assertions made by their authors and no admission is made that any reference constitutes prior art. Applicant reserves the right to challenge the accuracy and pertinence of the cited references.

In view of the above, it will be seen that the several advantages of the invention are achieved and other advantageous results attained. As various changes could be made in the above methods and compositions without departing from the scope of the invention, it is intended that all matter contained in the above description and shown in the accompanying drawings shall be interpreted as illustrative and not limiting in a limiting sense. Thus, the breadth and scope of the present invention should not be limited by any of the above-described exemplary embodiments, but should be defined only in accordance with the following claims appended hereto and their equivalents.

What is claimed is:

1. A recombinant nucleic acid construct comprising a nucleic acid sequence encoding a membrane anchor domain peptide, wherein said membrane anchor domain peptide has at least 95% sequence identity to residues 60 to 355 of the amino acid sequence of SEQ ID NO: 2 and wherein said nucleic acid sequence encoding said membrane anchor domain peptide is operably linked to a heterologous expression control sequence and operably linked to a heterologous nucleic acid sequence comprising a site for operable insertion of a nucleic acid sequence encoding a polypeptide wherein said nucleic acid sequence encoding a polypeptide can be inserted in the same frame with said nucleic acid sequence encoding said membrane anchor domain peptide.

2. The recombinant nucleic acid construct of claim 1, wherein said recombinant nucleic acid construct further comprises a nucleic acid sequence encoding a heterologous polypeptide inserted into said site for operable insertion, wherein said nucleic acid sequence encoding a heterologous polypeptide is operably linked to said nucleic acid encoding said membrane anchor domain peptide.

3. The recombinant nucleic acid construct of claim 1, wherein said nucleic acid sequence encoding said membrane anchor domain peptide comprises residues 178 to 1065 of the nucleic acid sequence of SEQ ID NO: 1.

4. The recombinant nucleic acid of claim 1, wherein said heterologous expression control sequence is a promoter.

5. The recombinant nucleic acid of claim 1, wherein said construct further comprises a nucleic acid encoding a secretion signal sequence that is operably linked to said nucleic acid sequence encoding said membrane anchor domain peptide and operably linked to said site for operable insertion.

6. The recombinant nucleic acid of claim 5, wherein said secretion signal peptide is a native secretion signal sequence of a protein of interest, a P. pastoris acid phosphatase (PHO1) secretion signal sequence, a S. cerevisiae α-mating factor (α-MF) secretion signal sequence, a P. pastoris PIR secretion signal sequence, a S. cerevisiae PIR secretion signal sequence, or a P. acaciae killer toxin secretion signal sequence.

7. An isolated transformed cell comprising a nucleic acid sequence comprising a heterologous expression control sequence, a nucleic acid sequence encoding a secretion signal sequence, a nucleic acid sequence encoding a membrane anchor domain peptide that has at least 95% sequence identity to residues 60 to 355 of SEQ ID NO: 2 and a nucleic acid sequence encoding a heterologous polypeptide, wherein said heterologous expression control sequence and said nucleic acid sequences encoding said secretion signal sequence, said membrane anchor domain peptide, and said nucleic acid sequence encoding said membrane anchor domain peptide are operably linked to provide a transcript wherein sequences encoding said secretion signal sequence, said membrane anchor domain, and said heterologous polypeptide are in the same frame.

8. A method for expressing a heterologous polypeptide on a host cell comprising:
culturing a eukaryotic cell transformed with a recombinant nucleic acid construct, said recombinant nucleic acid construct comprising a heterologous expression control sequence, a nucleic acid sequence encoding a secretion signal sequence, a nucleic acid sequence encoding a membrane anchor domain peptide that has at least 95% sequence identity to residues 60 to 355 of the amino acid sequence of SEQ ID NO: 2, and a nucleic acid sequence encoding a heterologous polypeptide, wherein said heterologous expression control sequence, said sequence encoding a secretion signal sequence, said sequence encoding a membrane anchor domain peptide, and said sequence encoding a heterologous polypeptide are operably linked to provide a transcript wherein said sequences encoding said secretion signal sequence, said membrane anchor domain, and said heterologous polypeptide are in the same frame, and wherein said eukaryotic cell is cultured under conditions permitting expression of said heterologous polypeptide, thereby expressing said heterologous polypeptide on said host cell.

9. The method of claim 8, wherein said secretion signal peptide is a native secretion signal sequence of a protein of interest, a P. pastoris acid phosphatase (PHO1) secretion signal sequence, a S. cerevisiae α-mating factor (α-MF) secretion signal sequence, a P. pastoris PIR secretion signal sequence, a S. cerevisiae PIR secretion signal sequence, or a P. acaciae killer toxin secretion signal sequence.

* * * * *